(12) United States Patent
Wagoner et al.

(10) Patent No.: US 11,559,045 B2
(45) Date of Patent: Jan. 24, 2023

(54) SYNERGISTIC MIXTURE FOR INDUCING HYGIENIC BEHAVIOR IN HONEY BEES, AND RELATED COMPOSITIONS AND METHODS

(71) Applicant: University of North Carolina at Greensboro, Greensboro, NC (US)

(72) Inventors: Kaira Wagoner, Greensboro, NC (US); Olav Rueppell, Greensboro, NC (US)

(73) Assignee: University of North Carolina at Greensboro, Greensboro, NC (US)

( * ) Notice: Subject to any disclaimer, the term of this patent is extended or adjusted under 35 U.S.C. 154(b) by 0 days.

(21) Appl. No.: 17/498,741

(22) Filed: Oct. 11, 2021

(65) Prior Publication Data

US 2022/0022430 A1    Jan. 27, 2022

Related U.S. Application Data

(63) Continuation of application No. PCT/US2020/027564, filed on Apr. 9, 2020.
(60) Provisional application No. 62/831,277, filed on Apr. 9, 2019.

(51) Int. Cl.
| | | |
|---|---|---|
| *A01K 51/00* | (2006.01) | |
| *A01N 25/00* | (2006.01) | |
| *C07C 1/00* | (2006.01) | |
| *C07C 11/00* | (2006.01) | |
| *C07C 11/02* | (2006.01) | |

(52) U.S. Cl.
CPC .............. *A01K 51/00* (2013.01); *A01N 25/00* (2013.01); *C07C 1/00* (2013.01); *C07C 11/00* (2013.01); *C07C 11/02* (2013.01)

(58) Field of Classification Search
CPC ...................................................... A01K 51/00
See application file for complete search history.

(56) References Cited

U.S. PATENT DOCUMENTS

| | | | |
|---|---|---|---|
| 7,049,373 | B2 | 5/2006 | Matyjaszewski et al. |
| 7,666,057 | B2 | 2/2010 | Junqueira de Souza et al. |
| 7,816,441 | B2 | 10/2010 | Elizalde et al. |
| 7,922,559 | B2 | 4/2011 | Cook |
| 2002/0182977 | A1 | 12/2002 | Page, Jr. et al. |
| 2005/0048093 | A1 | 3/2005 | Milani et al. |
| 2007/0026765 | A1 | 2/2007 | Renn |
| 2009/0036551 | A1 | 2/2009 | Venkatesh et al. |

(Continued)

FOREIGN PATENT DOCUMENTS

| | | |
|---|---|---|
| CN | 103875549 A | 6/2014 |
| DE | 102005010137 A1 | 9/2006 |

(Continued)

OTHER PUBLICATIONS

Nazzi, Francesco, Giorgio Della Vedova, and Mauro d'Agaro. "A semiochemical from brood cells infested by Varroa destructor triggers hygienic behaviour in Apis mellifera." Apidologie 35.1 (2004): 65-70.*

(Continued)

*Primary Examiner* — Benjamin J Packard
(74) *Attorney, Agent, or Firm* — Julia A. Kim; In Vivo Patent Law

(57) ABSTRACT

The presently disclosed subject matter provides synergistic mixtures for inducing hygienic behavior in honey bees and related compositions and methods.

24 Claims, 16 Drawing Sheets

(56) References Cited

U.S. PATENT DOCUMENTS

| | | |
|---|---|---|
| 2009/0104288 A1 | 4/2009 | Probasco |
| 2009/0169893 A1 | 7/2009 | Ikegami et al. |
| 2009/0275681 A1 | 11/2009 | Venkatesh |
| 2010/0069597 A1 | 3/2010 | Venkatesh et al. |
| 2010/0234506 A1 | 3/2010 | Venkatesh et al. |

FOREIGN PATENT DOCUMENTS

| | | |
|---|---|---|
| DE | 102012022345 A1 | 5/2014 |
| FR | 2668332 A1 | 4/1992 |
| GR | 1004165 B | 2/2003 |
| KR | 2012129044 A | 11/2012 |
| RO | 116148 B | 11/2000 |
| RS | 83504 A | 2/2007 |
| RU | 2534586 C2 | 11/2014 |
| WO | 2005018313 A1 | 3/2005 |
| WO | 2011097749 A1 | 8/2011 |

OTHER PUBLICATIONS

Salvy, M., et al. "Modifications of the cuticular hydrocarbon profile of *Apis mellifera* worker bees in the presence of the ectoparasitic mite *Varroa jacobsoni* in brood cells." Parasitology 122.2 (2001): 145-159.*

Ibrahim, Abdullah, and Marla Spivak. "The relationship between hygienic behavior and suppression of mite reproduction as honey bee (*Apis mellifera*) mechanisms of resistance to Varroa destructor." Apidologie 37.1 (2006): 31-40.*

Del Piccolo, F., et al. "Selection of Apis mellifera workers by the parasitic mite *Varroa destructor* using host cuticular hydrocarbons." Parasitology 137.6 (2010): 967-973.*

Mzen, M.A., et al., Long-Term Global Trends in Crop Yield and Production Reveal No Current Pollination Shortage But Increasing Pollinator Dependency, Current Biology, Oct. 28, 2008, pp. 1572-1575, vol. 18.

Annoscia, D., et al., How does the mite Varroa destructor kill the honeybee Apis mellifera? Alteration of cuticular hydrcarbons and water loss in infested honeybees, Journal of Insect Physiology, 2012, pp. 1548-1555, vol. 58.

Aumeier, P., et al., Cuticular volatiles, attractivity of worker larvae and invasion of brood cells by Varroa mites. A comparison of Africanized and European honey bees, Chemoecology, 2002, pp. 65-75, vol. 12.

Bloomquist, G.J., et al., Introduction: history and overview of insect hydrocarbons, Cambridge University Press, 2010, p. 3.

Dani, F.R et al., Deciphering the recognition signature within the cuticular chemical profile of paper wasps Animal Behaviour, 2001, pp. 165-171, vol. 62.

Danka, R.G., et al., Varying congruence of hygienic responses to Varroa destructor and freeze-killed brood among Tifferent types of honeybees, Apidologie, 2013, pp. 447-457, vol. 44.

De Miranda, J.R., et al., Deformed Wing Virus, Journal of Invertebrate Pathology, 2010, pp. S48-S61, vol. 103.

Del Piccolo, F., et al., Selection of Apis mellifera workers by the parasitic mite Varroa destructor using host cuticular hydrocarbons, Parasitology, 2010, pp. 967-973, vol. 137.

Francis, B.R., et al., Extractable surface hydrocarbons of workers and drones of the genus Apis, Journal of Apicultural Research, 1985, pp. 13-26, vol. 24, Issue 1.

Gilliam, M., et al., Hygienic behavior of honey bees in relation to chalkbrood disease, Apidologie, 1983, pp. 29-39, vol. 14, Issue 1.

Gisder, S., et al., Deformed wing virus: replication and viral load in mites (Varroa destructor), Journal of General Virology, 2009, pp. 463-467, vol. 90.

Gramacho, K.P., et al., Differences in olfactory sensitivity and behavioral responses among honey bees bred for hygienic behavior, Behavioral Ecology and Sociobiology, 2003, pp. 472-479, vol. 54.

Haarmann, T., et al., Effects of fluvalinate and coumaphos on queen honey bees (Hymenoptera: Apidae) in two commercial queen rearing operations, Journal of Economic Entomology, 2002, pp. 28-35, vol. 95.

Hefelz, A., The evolution of hydrocarbon pheromone parsimony in ants (Hymenoptera: Formicidae)—interplay of colony odor uniformity and odor idiosyncrasy, Myrmecological News, Sep. 2007, pp. 59-68, vol. 10.

Highfield, A.C., et al., Deformed wing virus implicated in overwintering honeybee colony losses, Applied and Environmental Microbiology, 2009, pp. 7212-7220, vol. 75, No. 22.

Howard, R.W., et al., Ecological, behavioral, and biochemical aspects of insect hydrocarbons, Annu Rev Entomol, 2005, pp. 371-393, vol. 50.

Brahim, A., et al., Field trial of honey bee colonies bred for mechanisms of resistance against Varroa destructor, Apidologie, 2007, pp. 67-76, vol. 38.

Larsson, K., et al., Antimicrobial effect of simple lipids with different branches at the methyl end group, Antimicrobial Agents and Chemotherapy, 1975, pp. 742-750, vol. 8.

Le Conte, Y., et al., Varroa destructor changes its cuticular hydrocarbons to mimic new hosts, Biology Letters, 2015, pp. 1-4, vol. 11:20150233.

Martin, C., et al., Variations in chemical mimicry by the ectoparasitic mite Varroa jacobsoni according to the developmental stage of the host honey-bee Apis mellifera, Insect Biochemistry and Molecular Biology, 2001, pp. 365-379, vol. 31.

Mockel, N., et al., Horizontal transmission of deformed wing virus: pathological consequences in adult bees (Apis mellifera) depend on the transmission route, Journal of General Virology, 2011, pp. 370-373//, vol. 92.

Monde I F., et al., Antennae hold a key to Varroa-sensitive hygiene behaviour in honey bees, Scientific Reports 5, 2015, pp. 1-12.

Nascimento, D.L., et al. Acceptance threshold hypothesis is supported by chemical similarity of cuticular hydrocarbons in a stingless bee, Melipona asilvai, Journal of Chemical Ecology, 2012, pp. 1432-1440, vol. 38.

Nation, J.L., et al., Cuticular hydrocarbons from Varroa jacobsoni, Experimental & Applied Acarology, 1992, pp. 331-344, vol. 16.

Nazzi, F., et al., (Z)-8-Heptadecene from infested cells reduces the reproduction of Varroa destructor under laboratory conditions. Journal of Chemical Ecology, 2002, pp. 2181-2190, vol. 28.

Pei I Is, U.S., et al., Fluvalinate treatment of queen and worker honey bees (Apis mellifera L) and effects on subsequent mortality, queen acceptance and supersedure, Apidologie, 1991, pp. 1-7, vol. 22.

Soroker, V., et al., Hydrocarbon site of synthesis and circulation in the desert ant Cataglyphis niger, Journal of nsect Physiology, 2000, pp. 1097-1102, vol. 46.

Villa, J.D., et al., Simplified methods of evaluating colonies for levels of Varroa Sensitive Hygiene (VSH), Journal of Apicultural Research, 2009, pp. 162-167, vol. 48.

Kang, X., et al., Effects of parasitization by Varroa destructor on survivorship and physiological traits of Apis mellifera n correlation with viral incidence and microbial challenge, 2007, Parasitology, pp. 405-412, vol. 134.

Francis, B.R., et al., Hydrocarbons of the cuticle and hemolymph of the adult honey bee Hymenoptera: Apidae), Annals of the Entomological Society of America, 1989, pp. 486-494, vol. 82, No. 4.

Dliveira, C.C., et al., Variations on a theme: diversification of cuticular hydrocarbons in a clade of cactophilic Drosophila, BMC Evolutionary Biology, 2011, pp. 1-19, vol. 11, No. 179.

Trapnell, Cole et al., "Differential gene and transcript expression analysis of RNA-seq experiments with TopHat and Cufflinks," Nature Protocols, vol. 7, Issue 3, Mar. 1, 2012, Nature America, Inc, pp. 1-39.

Trapnell, Cole et al., "TopHat: discovering splice junctions with RNA-Seq," Bioinformatics, vol. 25, Issue 9, May 1, 2009, The Author(s), doi:10.1093/bioinformatics/btp120, pp. 1105-1111.

Trapnell, Cole et al., "Transcript assembly and abundance estimation from RNA-Seq reveals thousands of new transcripts and switching among isoforms," Nature Biotechnology, vol. 28, Issue 5, May 2010, Nature Publishing Group, pp. 1-20.

(56) References Cited

OTHER PUBLICATIONS

Tsigouri, Angeliki et al., "Study of tau-fluvalinate persistence in honey," Pest Management Science, vol. 57, 2001, Society of Chemical Industry, pp. 467-471.

Tsuruda, Jennifer M et al., "High-Resolution Linkage Analyses to Identify Genes That Influence Varroa Sensitive Hygiene Behavior in Honey Bees," Plos One, vol. 7, Issue 11, Nov. 2, 2012, www.plosone.org, pp. 1-8.

University of Maryland, "U.S. beekeepers lost 40 percent of bees in 2014-15," Science Daily, May 13, 2015, vww.sciencedaily.com/releases/2015/05/150513093605.htm, ScienceDaily, 5 pages.

Van Dooremalen, Coby et al., "Winter Survival of Individual Honey Bees and Honey Bee Colonies Depends on Level of Varroa destructor Infestation," PLoS ONE, vol. 7, Issue 4, Apr. 27, 2012, www.plosone.org, pp. 1-8.

Vanengelsdorp, Dennis et al., "A historical review of managed honey bee populations in Europe and the United States and the factors that may affect them," Journal of Invertebrate Pathology, vol. 103, Nov. 11, 2009, Elsevier Inc., pages S80-S95.

Vanengelsdorp, Dennis et al., "A national survey of managed honey bee 2010-11 winter colony losses in the USA: results from the Bee Informed Partnership," Journal of Apicultural Research, vol. 51, Issue 1, Apr. 2, 2015, BRA, pp. 115-124.

Vanengelsdorp, Dennis et al., "A Survey of Honey Bee Colony Losses in the U.S., Fall 2007 to Spring 2008," PLoS ONE, vol. 3, Issue 12, Dec. 2008, www.plosone.org, pp. 1-6.

Vanengelsdorp, Dennis et al., "Colony Collapse Disorder: A Descriptive Study," PLoS ONE, vol. 4, Issue 8, Aug. 3, 2009, www plosone org, pp. 1-17.

Mncenti, Marco et al., "Determination of Double Bond Position in Diunsaturated Compounds by Mass Spectrometry of Dimethyl Disulfide Derivatives," Analytical Chemistry, vol. 59, Issue 5,1987, pp. 694-699.

Nallner, Klaus, "Varroacides and their residues in bee products," Apidologie, vol. 30, Issue 2-3, 1999, INRA/DIB/AGIB/EIsevier, Paris, pp. 235-248.

Nang, Ying et al., "Nurse bee behaviour manipulates worker honeybee (Apis mellifera L.) reproductive development," Animal Behaviour, vol. 92,2014, The Association for the Study of Animal Behaviour. Published by Elsevier Ltd., pp. 253-261.

Nantuch, Holly A et al., "Removal of Drone Brood From Apis mellifera (Hymenoptera: Apidae) Colonies to Control Varroa destructor (Acari: Varroidae) and Retain Adult Drones," Journal of Economic Entomology, vol. 102, Bsue 6, Dec. 2009, Entomological Society of America, pp. 2033-2040.

Ward, Kenneth et al., "Comparative Performance of Two Mite-Resistant Stocks of Honey Bees (Hymenoptera Apidae) in Alabama Beekeeping Operations," Journal of Economic Entomology, vol. 101, Issue 3, Jun. 2008, Entomological Society of America, pp. 654-659.

Whitfield, Charles W et al., "Thrice Out of Africa: Ancient and Recent Expansions of the Honey Bee, Apis mellifera," Science, vol. 314, Oct. 27, 2006, American Association for the Advancement of Science (AAAS), pp. 642-645.

Williams, Geoffrey R et al., "Standard methods for maintaining adult Apis mellifera in cages under in vitro aboratory conditions," Journal of Apicultural Research, vol. 52, Issue 1, 2013, IBRA, pp. 1-36.

Williamson, Sally M et al., "Exposure to multiple cholinergic pesticides impairs olfactory learning and memory in honeybees," The Journal of Experimental Biology, vol. 216, Issue 10,2013, The Company of Biologists Ltd., pp. 1799-1807.

Wilson-Rich, Noah et al., "Genetic, Individual, and Group Facilitation of Disease Resistance in Insect Societies," Annual Review of Entomology, vol. 54, 2009, Annual Reviews, pp. 405-423.

Wu, Judy Y et al., "Sub-Lethal Effects of Pesticide Residues in Brood Comb on Worker Honey Bee (Apis mellifera) Development and Longevity," PLoS ONE, vol. 6, Issue 2, Feb. 23, 2011, www.plosone.org, pp. 1-11.

Kang, Xiaolong et al., "Impact of an ectoparasite on the immunity and pathology of an invertebrate: Evidence for host immunosuppression and viral amplification," Proceedings of the National Academy of Sciences (PNAS), vol. 102, Issue 21, May 24, 2005, The National Academy of Sciences of the USA, pp. 7470-7475.

Youngsteadt, Elsa et al., "Seed odor mediates an obligate ant-plant mutualism in Amazonian rainforests," Proceedings of the National Academy of Sciences (PNAS), vol. 105, Issue 12, Mar. 25, 2008, The National Academy of Sciences of the USA, pp. 4571-4575.

International Search Report and Written Opinion for International Patent Application No. PCT/US2016/040993, dated Oct. 18, 2016, 8 pages.

Huang, Alice S. et al., "Defective Viral Particles and Viral Disease Processes," Nature, vol. 226, Apr. 25, 1970, Nature Publishing Group, pp. 325-327.

Hunter, Wayne et al., "Large-Scale Field Application of RNAi Technology Reducing Israeli Acute Paralysis Virus Disease in Honey Bees (Apis mellifera, Hymenoptera: Apidae)," PLoS Pathogens, vol. 6, Issue 12, Dec. 23, 2010, https://doi.org/10.1371/journal.ppat.1001160, pp. 1-10.

Hurd, Hilary, "Manipulation of Medically Important Insect Vectors by Their Parasites," Annual Review of Entomology, vol. 48, 2003, Annual Reviews, pp. 141-161.

Brahim, Abdullah et al., "Field trial of honey bee colonies bred for mechanisms of resistance against Varroa iestructor," Apidologie, vol. 38, Issue 1, January-Feb. 2007, Inra/Dib-Agib/ Edp Sciences, pp. 67-76.

Brahim, Abdullah et al., "The relationship between hygienic behavior and suppression of mite reproduction as honey bee (Apis mellifera) mechanisms of resistance to Varroa destructor," Apidologie, vol. 37, Issue 1, January-Feb. 2006, Inra/Dib-Agib/ Edp Sciences, pp. 31-40.

Fantidis, Michael, D., "Ontogenesis of the Mite Varroa Jacobsoni in Worker and Drone Honeybee Brood Cells," Journal of Apicultural Research, vol. 22, Issue 3, 1983, IBRA, pp. 200-206.

Fantidis, Michael, D., Some Aspects of the Process of Varroa Jacobsoni Mite Entrance Into Honey Bee (Apis Mellifera) Brood Cells, Apidologie, vol. 19, Issue 4, 1988, Springer International Publishing AG, pp. 387-396.

Mdorf, Anton et al., "Alternative strategy in central Europe for the control of Varroa destructor in honey bee colonies," Apiacta, vol. 38,2003, International Federation of Beekeepers' Associations "Apimondia," pp. 258-285.

Johnson, Reed M et al., "Changes in transcript abundance relating to colony collapse disorder in honey bees (Apis mellifera)," Proceedings of the National Academy of Sciences (PNAS), vol. 106, Issue 35, Sep. 1, 2009, National Academy of Sciences, p. 14790-14795.

Johnson, Reed M., "Honey Bee Toxicology," Annual Review of Entomology, vol. 60, Oct. 10, 2014, Annual Reviews, p. 22 1 - 22.20.

Johnson, Reed M et al., "Pesticides and honey bee toxicity—USA," Apidologie, vol. 41, Issue 3, May-Jun. 2010, INRA/DIB-AGIB/ EDP Sciences, pp. 1-20.

Johnson, Reed M. et al., "Synergistic Interactions Between In-Hive Miticides in Apis mellifera," Journal of Economic Entomology, vol. 102, Issue 2, Apr. 2009, Entomological Society of America, pp. 474-479.

Kanbar, G. et al., "Ultrastructure and bacterial infection of wounds in honey bee (Apis mellifera) pupae punctured by Varroa mites," Parasitology Research, vol. 90, Issue 5, Aug. 2003, Springer International Publishing AG, pp. 349-354.

Kanga, Lambert et al., "Susceptibility of the small hive beetle, Aethina tumida (Coleoptera: Nitidulidae), to nsecticides and insect growth regulators," Apidologie, vol. 43, Issue 1, 2012, Inra, Dib and Springer-Veriag, pp. 95-102.

Katzav-Gozansky et al., "Plasticity of Caste-Specific Dufour's Gland Secretion in the Honey Bee (Apis mellifera L.)," Naturwissenschaften, vol. 84, 1997, Springer-Veriag, pp. 238-241.

Kimura, Taichi et al., "Synthesis of All the Stereoisomers of 13,17-Dimethyl-1-tritriacontene and 13,17-Dimethyl-1-pentatriacontene, the Contact Sex Pheromone Components of the

(56) References Cited

OTHER PUBLICATIONS

Female Tsetse Fly, Glossina austeni,"European Journal of Organic Chemistry, Pheromone synthesis, Part 211, 2001, WILEY-VCH VerlagGmbH, pp. 3385-3390.

Kirrane, Maria J. et al., "Asynchronous Development of Honey Bee Host and Varroa destructor (Mesostigmata Varroidae) Influences Reproductive Potential of Mites," Journal of Economic Entomology, vol. 104, Issue 4, Aug. 2011, Entomological Society of America, pp. 1146-1152.

Kochansky, Jan et al., "Screening alternative antibiotics against oxytetracycline-susceptible and -resistant Paenibacillus larvae," Apidologie, vol. 32, Issue 3, 2001, INRA/DIB-AGIB/EDP Sciences, pp. 215-222.

Kraus, Bernhard et al., "Effect of Varroa jacobsoni (Mesostigmata: Varroidae) on Feral Apis mellifera Hymenoptera: Apidae) in California," Environmental Entomology, vol. 24, Issue 6, Dec. 1995, Entomological Society of America, pp. 1473-1480.

Kuster, Ryan D. et al., "Immunogene and viral transcript dynamics during parasitic Varroa destructor mite infection of developing honey bee (Apis mellifera) pupae," The Journal of Experimental Biology, vol. 217, Issue 10,2014, The Company of Biologists Ltd., pp. 1710-1718.

Langmead, Ben et al., "Fast gapped-read alignment with Bowtie 2," Nature Methods, vol. 9, Issue 4, 2012, Nature America, Inc., pp. 1-8.

Le Conte, Yves et al., "Honey bee colonies that have survived Varroa destructor," Apidologie, vol. 38, Issue 6, November-Dec. 2007, Inra, Edp Sciences, pp. 566-572.

Le Conte, Yves et al., "Identification of a Brood Pheromone in Honeybees," Naturwissenschaften, vol. 77, Issue 7, 1990, Springer-Veriag, pp. 334-336.

Le Conte, Yves et al., "Primer Pheromones in Social Hymenoptera," Annual Review of Entomology, vol. 53, 2008, Annual Reviews, pp. 523-542.

Le Conte, Yves et al., "Varroa mites and honey bee health: can Varroa explain part of the colony losses?," Apidologie, vol. 41, Issue 3, Jan. 1, 2010, Springer Verlag, pp. 353-363.

Lee, Kathleen V. et al., "A national survey of managed honey bee 2013-2014 annual colony losses in the USA," Apidologie, vol. 46, Issue 3, May 2015, Springer Paris, pp. 292-305.

Li, Dongsheng et al., "Defective Interfering Viral Particles in Acute Dengue Infections," PLoS ONE, vol. 6, Issue 1, Apr. 2011, www plosone org, pp. 1-12.

Locke, Barbara et al., "Characteristics of honey bee colonies (Apis mellifera) in Sweden surviving Varroa Iestructor infestation," Apidologie, vol. 42, Issue 4, Aug. 2011, Inra, Dib-Agib and Springer Science+ Business Media B.V., pp. 533-542.

Locke, Barbara et al., "Host adaptations reduce the reproductive success of Varroa destructor in two distinct European honey bee populations," Ecology and Evolution, vol. 2, Issue 6, Feb. 29, 2012, Blackwell Publishing Ltd., pp. 1144-1150.

Locke, Barbara et al., "Increased Tolerance and Resistance to Virus Infections: A Possible Factor in the Survival of Varroa destructor-Resistant Honey Bees (Apis mellifera)," Plos One, vol. 9, Issue 6, Jun. 2014, www. plosone.org, pp. 1-7.

Mant, Jim et al., "Cuticular Hydrocarbons as Sex Pheromone of the Bee Colletes cunicularius and the Key to Its Mimicry by the Sexually Deceptive Orchid, Ophrys exaltata," Journal of Chemical Ecology, vol. 31, Issue 8, Aug. 2005, Springer Science + Business Media, Inc., p. 1765-1787.

Maori, E. et al., "IAPV, a bee-affecting virus associated with Colony Collapse Disorder can be silenced by dsRNA ngestion," Insect Molecular Biology, vol. 18, Issue 1, 2009, The Royal Entomological Society, pp. 55-60.

Martel, Anne-Claire et al., "Acaricide residues in honey and wax after treatment of honey bee colonies with Apvar® or Asuntol® 50," Apidologie, vol. 38, Issue 6, Nov. 2007, INRA, EDP Sciences, pp. 534-544.

Martin, Stephen, "A population model for the ectoparasitic mite Varroa jacobsoni in honey bee (Apis mellifera) colonies," Ecological Modelling, vol. 109, Issue 3, 1998, Elsevier Science B V., pp. 267-281.

Martin, Stephen J., "Global honey bee viral landscape altered by a parasitic mite," Science, vol. 336, Jun. 8, 2012, American Association for the Advancement of Science, pp. 1304-1306.

Martin, Stephen J., "Ontogenesis of the mite Varroa jacobsoni Oud. in worker brood of the honeybee Apis mellifera L. under natural conditions," Experimental & Applied Acarology, vol. 18, Issue 2, 1994, Science and Technology Letters, pp. 87-100.

Martin, Stephen J., "The role of Varroa and viral pathogens in the collapse of honeybee colonies: a modelling approach," Journal of AppliedEcology, vol. 38, Issue 5, 2001, British Ecological Society, pp. 1082-1093.

Masterman, R. et al., "Olfactory and behavioral response thresholds to odors of diseased brood differ between hygienic and non-hygienic honey bees (Apis mellifera L.)," Journal of Comparative Physiology A, vol. 187, Issue 6, Jul. 11, 2001, Springer-Veriag, pp. 441-452.

McMenamin, Alexander et al., "Honey bee (Apis mellifera) colony losses and associated viruses," Current Dpinion in Insect Science, vol. 8, 2015, Elsevier Ltd., pp. 1-9.

Millar, Jocelyn G., "Chapter 8: Chemical synthesis of insect cuticular hydrocarbons," Insect Hydrocarbons Biology, Biochemistry, and Chemical Ecology (book), Part I—Chemistry, Biochemistry, and Physiology, 2010, Cambridge University Press, pp. 163-186.

Mondet, Fanny et al., "On the Front Line: Quantitative Virus Dynamics in Honeybee (Apis mellifera L.) Colonies along a New Expansion Front of the Parasite Varroa destructor," PLOS Pathogens, vol. 10, Issue 8, Aug. 2014, vww.plospathogens.org, pp. 1-15.

Mondet, Fanny et al., "Specific Cues Associated With Honey Bee Social Defence against Varroa destructor Infested Brood," Scientific Reports, vol. 6, May 3, 2016, www.nature.com/scientificreports, pp. 1-9.

Morse, Roger A. et al., "The Value of Honey Bees As Pollinators of U.S. Crops in 2000," Bee Culture Magazine, vol. 128, Issue 3, 2000, pp. 1-15.

Mortazavi, Ali et al., "Mapping and quantifying mammalian transcriptomes by RNA-Seq," Nature Methods, vol. 5, Issue 7, Jul. 2008, Nature Publishing Group, pp. 621-628.

Mullin, Christopher A. et al., "High Levels of Miticides and Agrochemicals in North American Apiaries Implications for Honey Bee Health," PLoS ONE, vol. 5, Issue 3, Mar. 19, 2010, www.plosone.org, pp. 1-19.

National Research Council, "Status of Pollinators in North America," Board on Life Sciences Board on Agriculture and Natural Resources Division on Earth and Life Studies, 2007, Washington, DC, National Academy of Sciences, 327 pages.

Nault, Brian A. et al., "Limitations of Using Regression and Mean Separation Analyses for Describing the Response of Crop Yield to Defoliation: A Case Study of the Colorado Potato Beetle (Coleoptera: Chrysomelidae) on Potato," Journal of Economic Entomology, vol. 91, Issue 1, Feb. 1, 1998, Entomological Society of America, pp. 7-20.

Nazzi, Francesco et al., "A semiochemical from brood cells infested by Varroa destructor triggers hygienic behaviour in Apis mellifera," Apidologie, vol. 35, Issue 1, 2004, Springer Verlag, pp. 65-70.

Nazzi, Francesco et al., "Synergistic Parasite-Pathogen Interactions Mediated by Host Immunity Can Drive the Collapse of Honeybee Colonies," PLoS Pathogens, vol. 8, Issue 6, Jun. 2012, www.plospathogens.org, pp. 1-16.

Neumann, Peter et al., "Varroa invasion and virus adaptation," Trends in Parasitology, vol. 28, Issue 9, Sep. 2012, Elsevier Ltd., pp. 353-354.

Nojima, Satoshi et al., "A Simple, Convenient, and Efficient Preparative GC System that Uses a Short Megabore Capillary col. as a Trap," Journal of Chemical Ecology, vol. 34, Issue 3, Mar. 2008, Springer, pp. 418-428.

Nojima, Satoshi et al., "Identification of the Sex Pheromone of the German Cockroach, Blattella germanica," Science, vol. 307, Issue 5712, Feb. 18, 2005, American Association for the Advancement of Science, pp. 1104-1106.

(56) References Cited

OTHER PUBLICATIONS

Oldroyd, Benjamin p et al., "Genetic diversity promotes homeostasis in insect colonies," TRENDS in Ecology and Evolution, vol. 22, Issue 8, Jun. 18, 2007, Elsevier Ltd., pp. 408-413.

Otvos, Laszlo Jr et al., "Interaction between Heat Shock Proteins and Antimicrobial Peptides," Biochemistry, vol. 39, Issue 46, Nov. 21, 2000, American Chemical Society, pp. 14150-14159.

Oxley, Pe I Er R et al., "Six quantitative trait loci influence task thresholds for hygienic behaviour in honeybees (Apis mellifera)," Molecular Ecology, vol. 19, Issue 7, Apr. 2010, Blackwell Publishing Ltd., pp. 1452-1461.

Parker, Robert et al., "Correlation of proteome-wide changes with social immunity behaviors provides insight into Yesistance to the parasitic mite, Varroa destructor, in the honey bee (Apis mellifera)," Genome Biology, vol. 13, Bsue 9, Sep. 28, 2012, BioMed Central Ltd., 46 pages.

Peng, Ying-Shen et al., "The Resistance Mechanism of the Asian Honey Bee, Apis cerana Fabr., to an Ectoparasitic Mite, Varroa jacobsoni Oudemans," Journal of Invertebrate Pathology, vol. 49, Issue 1, 1987, Academic Press, Inc., pp. 54-60.

Pepke, Shirley et al., "Computation for ChIP-seq and RNA-seq studies," Nature Methods, vol. 6, Issue 11s, Nov. 2009, Nature Publishing Group, pp. 1-25.

Pernal, Si Ephen F et al., "Breeding for hygienic behaviour in honeybees (Apis mellifera) using free-mated nucleus colonies," Apidologie, vol. 43, Issue 4, Jul. 2012, Inra, Dib and Springer-Verlag, pp. 403-416.

Pettis, Jeffery S et al., "Effects of coumaphos on queen rearing in the honey bee, Apis mellifera," Apidologie, vol. 35, Issue 6, Nov. 2004, Inra/Dib-Agib/ Edp Sciences, pp. 605-610.

Pettis, Jeffery S et al., "Pesticide exposure in honey bees results in increased levels of the gut pathogen Nosema," Naturwissenschaften, vol. 99, Issue 2, Jan. 13, 2012, Springerlink, pp. 153-158.

Podgwaite, J. D. et al., "Latency of Insect Viruses," Advances in Virus Research, vol. 31, 1986, Academic Press, Inc., pp. 293-320.

Potts, Simon G. et al., "Global pollinator declines: trends, impacts and drivers," Trends in Ecology and Evolution, vol. 25, Issue 6, Feb. 24, 2010, Elsevier Ltd., pp. 345-353.

Principal De D'aubeterre, Judith et al., "A scientific note of an application of isotope ratio mass spectrometry to feeding by the mite, Varroa jacobsoni Oudemans, on the honeybee, Apis mellifera L.," Apidologie, vol. 30, Issue 1, 1999, Springer Verlag, pp. 351-352.

Rademacher, Eva et al., "Oxalic acid for the control of varroosis in honey bee colonies - a review," Apidologie, vol. 37, Issue 1, 2006, Inra/Dib-Agib/ Edp Sciences, pp. 98-120.

Richard, F-J et al., "Modulation of social interactions by immune stimulation in honey bee, Apis mellifera, workers," BMC Biology, vol. 6, Issue 1, Nov. 17, 2008, BioMed Central Ltd., pp. 1-13.

Rinderer, Thomas E. et al., "Breeding for resistance to Varroa destructor in North America," Apidologie, vol. 11, Issue 3, May 2010, INRA/DIB-AGIB/EDP Sciences, pp. 409-424.

Rosenkranz, Peter et al., "Biology and control of Varroa destructor," Journal of Invertebrate Pathology, vol. 103, Nov. 11, 2009, Elsevier Inc., pages S96-S119.

Rosenkranz, Peter et al., "Differential hygienic behavior towards Varroa jacobsoni in capped worker brood of Apis cerana depends on alien scent adhering to the mites," Journal of Apicultural Research, vol. 32, Issue 2, 1993, BRA, pp. 89-93.

Rothenbuhler, Walter C., "Behavior Genetics of Nest Cleaning in Honey Bees. IV. Responses of F1 and Backcross Generations to Disease-Killed Brood," American Zoologist, vol. 4, Issue 2, May 1964, Oxford University Press, pp. 111-123.

Runckel, Charles et al., "Temporal Analysis of the Honey Bee Microbiome Reveals Four Novel Viruses and Seasonal Prevalence of Known Viruses, Nosema, and Crithidia," PLoS ONE, vol. 6, Issue 6, Jun. 7, 2011, www. plosone.org, pp. 1-18.

Rueppel, O. et al., "Altruistic self-removal of health-compromised honey bee workers from their hive," Journal of Evolutionary Biology, vol. 23, Issue 7, Jul. 2010, European Society for Evolutionary Biology, pp. 1538-1546.

Ryabov, Eugene V. et al., "A Virulent Strain of Deformed Wing Virus (DWV) of Honeybees (Apis mellifera) Prevails after Varroa destructor-Mediated, or In Vitro, Transmission," PLOS Pathogens, vol. 10, Issue 6, Jun. 26, 2014, vww.plospathogens.org, pp. 1-21.

Salvy, M. et al., "Modifications of the cuticular hydrocarbon profile of Apis mellifera worker bees in the presence of the ectoparasitic mite Varroa jacobsoni in brood cells," Parasitology, vol. 122, Issue 2, Feb. 2001, Cambridge University Press, pp. 145-159.

Sammataro, Diana et al., "Parasitic Mites of Honey Bees: Life History, Implications, and Impact," Annual Review of Entomology, vol. 45, 2000, Annual Reviews, pp. 519-548.

Sammataro, Diana et al.," I he Resistance of Varroa Mites (Acari: Varroidae) to Acaricides and the Presence of Esterase," International Journal of Acarology, vol. 31, Issue 1, 2005, Taylor & Francis, pp. 67-74.

Schoning, Caspar et al., "Evidence for damage-dependent hygienic behaviour towards Varroa destructorparasitised brood in the western honey bee, Apis mellifera," The Journal of Experimental Biology, vol. 215, Issue 2, 2012, The Company of Biologists Ltd., pp. 264-271.

Seeley, Thomas D. et al., "Honey bees of the Arnot Forest: a population of feral colonies persisting with Varroa iestructor in the northeastern United States," Apidologie, vol. 38, Issue 1, 2007, EDP Sciences, pp. 19-29.

Seeley, Thomas D. et al., "Queen promiscuity lowers disease within honeybee colonies," Proceedings of the Royal Society B, vol. 274, Issue 1606, Sep. 26, 2006, The Royal Society, pp. 67-72.

Severson, D.W. et al., "Heat stress induced enhancement of heat shock protein gene activity in the honey bee (Apis mellifera)," Experientia, vol. 46, Issue 7, Jul. 1990, Birkhauser Verlag Basel, pp. 737-739.

Shelton, Daniel R. et al., "Isolation and Characterization of Coumaphos-Metabolizing Bacteria from Cattle Dip," Applied and Environmental Microbiology, vol. 54, Issue 10, Oct. 1988, American Society for Microbiology, pp. 2566-2571.

Singh, Rajwinder et al., "RNA Viruses in Hymenopteran Pollinators: Evidence of Inter-Taxa Virus Transmission via Pollen and Potential Impact on Non-Apis Hymenopteran Species," PLoS ONE, vol. 5, Issue 12, Dec. 22, 2010, www.plosone.org, pp. 1-16.

Slessor, Keith N. et al., "Pheromone Communication in the Honeybee," Journal of Chemical Ecology, vol. 31, Bsue 11, Nov. 2005, Springer Science + Business Media, Inc., pp. 2731-2745.

Smet, Lina De et al., "BeeDoctor, a Versatile MLPA-Based Diagnostic Tool for Screening Bee Viruses," Plos One, vol. 7, Issue 10, Oct. 2012, www plosone org, pp. 1-8.

Sonnet, P.E. et al., "Sex Pheromone of the Stable Fly: Identification, Synthesis, and Evaluation of Alkenes from Female Stable Flies," Journal of Chemical Ecology, vol. 5, Issue 3, May 1979, Springer US, pp. 353-361.

Spivak, Marla et al., "Field Assays for Hygienic Behavior in Honey Bees (Hymenoptera: Apidae)," Journal of Economic Entomology, vol. 91, Issue 1, Feb. 1, 1998, EntomologicalSociety of America, pp. 64-70.

Spivak, Marla, "Honey bee hygienic behavior and defense against Varroa jacobsoni," Apidologie, vol. 27, Issue 1, Aug. 14, 1996, Springer Verlag, pp. 245-260.

Spivak, Marla et al., "Hygienic Behavior in the Honey Bee (Apis mellifera L.) and the Modulatory Role of Dctopamine," Developmental Neurobiology, vol. 55, Issue 3, Jun. 2003, Wiley Periodicals, Inc., pp. 341-354.

Spivak, Marla et al., "Hygienic behaviour of honey bees and its application for control of brood diseases and arroa," Bee World, vol. 79, Issue 4, 1998, IBRA, pp. 169-186.

Spivak, Marla et al., "New Direction for the Minnesota Hygienic Line of Bees," American Bee Journal, vol. 148, Bsue 12, Dec. 2008, pp. 1085-1086.

Spivak, Marla et al., "Performance of hygienic honey bee colonies in a commercial apiary," Apidologie, vol. 29, Bsue 3, 1998, Springer Verlag, pp. 291-302.

(56) References Cited

OTHER PUBLICATIONS

Spivak, Marla et al., "The Plight of the Bees," Environmental Science & Technology, vol. 45, Issue 1, Sep. 14, 2010, American Chemical Society, pp. 34-38.
Spivak, Marla et al., "Resistance to American foulbrood disease by honey bee colonies Apis mellifera bred for hygienic behavior," Apidologie, vol. 32, Issue 6, November-Dec. 2001, INRA/DIB-AGIB/EDP Sciences, pp. 555-565.
Spivak, Marla et al., "Varroa destructor Infestation in Untreated Honey Bee (Hymenoptera: Apidae) Colonies Selected for Hygienic Behavior," Journal of Economic Entomology, vol. 94, Issue 2, Apr. 2001, Entomological Society of America, pp. 326-331.
Spleen, Angela M. et al., "A national survey of managed honey bee 2011-12 winter colony losses in the United States: results from the Bee Informed Partnership," Journal of Apicultural Research, vol. 52, Issue 2, 2013, IBRA, pp. 44-53.
Spotter, A et al., "Development of a 44K Snp assay focussing on the analysis of a varroa-specific defence behaviour in honey bees (Apis mellifera camica)," Molecular Ecology Resources, vol. 12, Issue 2, Mar. 2012, Blackwell Publishing Ltd., pp. 323-332.
Steinhauer, N. A. et al., "A national survey of managed honey bee 2012-2013 annual colony losses in the USA Yesults from the Bee Informed Partnership," Journal of Apicultural Research, vol. 53, Issue 1, Feb. 2014, BRA, pp. 1-18.
Swanson, Jodi A. I et al., Odorants that Induce Hygienic Behavior in Honeybees: Identification of Volatile Compounds in Chalkbrood-Infected Honeybee Larvae, Journal of Chemical Ecology, vol. 35, Issue 9, Sep. 3, 2009, Springer Science + Business Media, LLC., pp. 1108-1116.
Sylvester, H. Allen et al., "Varroa in the Mating Yard: II. The Effects of Varroa and Fluvalinate on Drone Mating Competitiveness," American Bee Journal, vol. 139, Issue 2, Mar. 1999, American Bee Journal, pp. 225-227.
Torto, Baldwyn et al., "Standard methods for chemical ecology research in Apis mellifera," Journal of Apicultural Research, vol. 52, Issue 4, 2013, IBRA, pp. 1-35.
Aboshi, Takako et al., "Biosynthesis of linoleic acid in Tyrophagus mites (Acarina: Acaridae)," Insect Biochemistry and Molecular Biology, vol. 43, Issue 11, 2013, Elsevier Ltd., pp. 991-996.
Aizen, Marcelo A. et al., "The Global Stock of Domesticated Honey Bees Is Growing Slower Than Agricultural Demand for Pollination," Current Biology, vol. 19, Issue 11, Jun. 9, 2009, Elsevier Ltd, pp. 915-918.
Alaux, Cedric et al., "Nutrigenomics in honey bees: digital gene expression analysis of pollen's nutritive effects on healthy and varroa-parasitized bees," BMC Genomics, vol. 12, Issue 496, Oct. 10, 2011, BioMed Central, fittp://www.biomedcentral.com/1471-2164/12/496, pp. 1-13.
Amdam, Gro V. et al., "Altered Physiology in Worker Honey Bees (Hymenoptera: Apidae) Infested with the Mite Varroa destructor (Acari: Varroidae): A Factor in Colony Loss During Overwintering?" Journal of Economic Entomology, vol. 97, Issue 3, Jun. 2004, Entomological Society of America, pp. 741-747.
Anders, Simon et al., HTSeq—a Python framework to work with high-throughput sequencing data, Bioinformatics, vol. 31, Issue 2, 2015, Oxford University Press, pp. 166-169.
Andersen, Claus Lindbjerg et al., "Normalization of Real-Time Quantitative Reverse Transcription-PCR Data: A Model-Based Variance Estimation Approach to Identify Genes Suited for Normalization, Applied to Bladder and Colon Dancer Data Sets," Cancer Research, vol. 64, Issue 15, Aug. 1, 2004, American Association for Cancer Research, pp. 5245-5250.
Anderson, D.L et al., "Varroa jacobsoni (Acari: Varroidae) is more than one species," Experimental and Applied Acarology, vol. 24, Issue 3, Jan. 6, 2000, Kluwer Academic Publishers, pp. 165-189.
Arrese, Estela L. et al., "Insect Fat Body: Energy, Metabolism, and Regulation," Annual Review of Entomology, vol. 55, 2010, Annual Reviews, pp. 207-225.
Author Unknown, "Bee Healthy Roadmap: Improving Honey Bee Health," Honey Bee Health Coalition, Oct. 2014, http://honeybeehealthcoalition.org/wp-contentuploads/2014/12Bee-Healthy-Roadmap-Oct. 2014.pdf, www. tioneybeehealthcoalition.org, 6 pages.
Aumeier, Pia et al., "Scent or movement of Varroa destructor mites does not elicit hygienic behaviour by Africanized and Carniolan honey bees," Apidologie, vol. 32, Issue 3, May-Jun. 2001, INRA/DIB-AGIB/EDP Sciences, pp. 253-263.
Azzami, Klara et al., "Infection of honey bees with acute bee paralysis virus does not trigger humoral or cellular mmune responses," Archives of Virology, vol. 157, Issue 4, Jan. 19, 2012, Springer, pp. 689-702.
Baracchi, David et al., "Evidence for antiseptic behaviour towards sick adult bees in honey bee colonies," Journal of Insect Physiology, vol. 58, Issue 12, Dec. 2012, Elsevier Ltd., pp. 1589-1596.
Behrens, Dieter et al., "Three QTL in the honey bee Apis mellifera L. suppress reproduction of the parasitic mite Varroa destructor," Ecology and Evolution, vol. 1, Issue 4, Dec. 2011, Blackwell Publishing Ltd., pp. 151-458.
Bello, Jan E et al., "Isolation and determination of absolute configurations of insect-produced methyl-branched hydrocarbons," Proceedings of the National Academy of Sciences, vol. 112, Issue 4, Jan. 27, 2015, PNAS, pp. 1077-1082.
Benoit, Joshua B et al., "Mycoflora and fungal vector capacity of the parasitic mite Varroa destructor Mesostigmata: Varroidae) in honey bee (Hymenoptera: Apidae) colonies," International Journal of Acarology, vol. 30, Issue 2, 2004, Taylor & Francis, pp. 103-106.
Berry, Jennifer, "Pesticides, Bees And Wax: An unhealthy, untidy mix," Bee Culture, Jan. 2009, vol. 137, Bee Culture, pp. 33-35.
Biesmeijer, J. C. et al., "Parallel Declines in Pollinators and Insect-Pollinated Plants in Britain and the Netherlands," Science, vol. 313, Issue 5785, Jul. 21, 2006, American Association for the Advancement of Science (AAAS), pp. 351-354.
Bogdanov, Stefan, "Contaminants of bee products," Apidologie, vol. 37, Issue 1, January-Feb. 2006, Nra/Dib-Agib/ Edp Sciences, pp. 1-18.
Boecking, Otto et al., "Behavioral defenses of honey bees against Varroa jacobsoni Oud.," Apidologie, vol. 30, Bsue 2-3,1999, Elsevier, pp. 141-158.
Boecking, Otto et al., "Heritability of the Varroa-speci@c hygienic behaviour in honey bees (Hymenoptera Apidae)," Journal of Animal Breeding and Genetics, vol. 117, Issue 6, Dec. 2000, Blackwell Wissenschafts-Verlag, Berlin, pp. 417-424.
Boecking, Otto et al., "The pore in the hard conical Apis cerana drone capping results from a spinning process," Apidologie, vol. 30, Issue 6, 1999, INRA/EDP Sciences/DIB-AGIB, pp. 513-519.
Boecking, O. et al., "The removal response of Apis mellifera L. colonies to brood in wax and plastic cells after artificial and natural infestation with Varroa jacobsoni Oud. and to freeze-killed brood," Experimental & Applied Acarology, vol. 16, Issue 4, Dec. 1992, Elsevier Science Publishers B.V., pp. 321-329.
Boecking, O. et al., "Varroosis - the Ongoing Crisis in Bee Keeping," Journal fur Verbraucherschutz und Lebensmittelsicherheit, vol. 3, Issue 2, May 2008, SP Birkhauser Verlag Basel, pp. 221-228.
Boncristiani, Humberto, et al., "Direct effect of acaricides on pathogen loads and gene expression levels in honey bees Apis mellifera," Journal of Insect Physiology, vol. 58, Issue 5, May 2012, Elsevier Ltd., pp. 1-8.
Boncristiani, Humberto F et al., "In Vitro Infection of Pupae with Israeli Acute Paralysis Virus Suggests Disturbance of Transcriptional Homeostasis in Honey Bees (Apis mellifera)," Plos One, vol. 8, Issue 9, Sep. 2013, www.plosone.org, pp. 1-11.
Boroczky, Katalin et al., "Insects groom their antennae to enhance olfactory acuity," Proceedings of the National Academy of Sciences (PNAS), vol. 110, Issue 9, Feb. 26, 2013, www.pnas.org/cgi/doi/10.1073/onas. 1212466110, National Academy of Sciences, pp. 3615-3620.
Bourgeois, A. Lelania et al., "Genetic Characterization of Russian Honey Bee Stock Selected for Improved Resistance to Varroa destructor," Journal of Economic Entomology, vol. 102, Issue 3, Jun. 2009, pp. 1233-1238.
Bowen-Walker, p. L et al., "The Transmission of Deformed Wing Virus between Honeybees (Apis mellifera L.) by the Ectoparasitic Mite Varroa jacobsoni Oud," Journal of Invertebrate Pathology, vol. 73, Issue 1, Jan. 1999, Academic Press, pp. 101-106.

(56) References Cited

OTHER PUBLICATIONS

Burley, Lisa M et al., "Survival of Honey Bee (Hymenoptera: Apidae) Spermatozoa Incubated at Room Temperature from Drones Exposed to Miticides," Journal of Economic Entomology, vol. 101, Issue 4, Aug. 1, 2008, Entomological Society of America, pp. 1081-1087.

Calderon, Rafael A et al., "Behavior of varroa mites in worker brood cells of Africanized honey bees," Experimental and Applied Acarology, vol. 49, Issue 4, Dec. 2009, Springer Science+Business Media B.V, pp. 329-338.

Calderone, Nicholas W., "Evaluation of Formic Acid and a Thymol-Based Blend of Natural Products for the Fall Control of Varroa jacobsoni (Acari: Varroidae) in Colonies of Apis mellifera (Hymenoptera: Apidae)," Journal of Economic Entomology, vol. 92, Issue 2, Apr. 1, 1999, Entomological Society of America, pp. 253-260.

Calderone, Nicholas W., "Insect Pollinated Crops, Insect Pollinators and US Agriculture: Trend Analysis of Aggregate Data for the Period 1992-2009," PLoS ONE, vol. 7, Issue 5, May 22, 2012, www.plosone.org, pp. 1-27.

Carlson, D.A. et al., "Polyunsaturated Hydrocarbons in the Stable Fly," Journal of Chemical Ecology, vol. 11, Issue 11, Nov. 1985, Springer, pp. 1485-1496.

Carreck, Norman L. et al., "Honey bee colony collapse and changes in viral prevalence associated with Varroa iestructor," Journal of Apicultural Research, vol. 49, Issue 1, 2010, IBRA, pp. 93-94.

Carreck, Norman, "Varroa - still a problem in the 21st century?" Jan. 2011, International Bee Research Association, 2 pages.

Caulkins, Peter, "Environmental Protection Agency: Tau-fluvalinate; Reregistration Eligibility Decision for Low Risk Pesticide; Notice of Availability," Agency No. OPP-2005-0230, Docket No. FRL-7742-7, Nov. 7, 2005, in Federal Register: A Notice by the Environmental Protection Agency, vol. 70, Issue 220, Nov. 16, 2005, Office of the Federal Register, p. 69555-69557.

Charlier, Cathy et al., "Oocyte-somatic cells interactions, lessons from evolution," BMC Genomics, vol. 13, Oct. 2012, BioMed Central Ltd., pp. 1-18.

Chen, Yan Ping et al., "Chapter 2: Honey Bee Viruses," Advances in Virus Research (book), vol. 70,2007, New fork, New York, Academic Press, pp. 33-80.

Chen, Yanping et al., "Multiple virus infections in the honey bee and genome divergence of honey bee viruses," Journal of Invertebrate Pathology, vol. 87, Issue 2-3, October-Nov. 2004, Elsevier Inc., pp. 84-93.

Chen, Yanping et al., "Transmission of Kashmir bee virus by the ectoparasitic mite Varroa destructor," Apidologie, vol. 35, Issue 4, July-Aug. 2004, Springer Verlag, pp. 441-448.

Claudianos, C. et al., "A deficit of detoxification enzymes: pesticide sensitivity and environmental response in the honeybee," Insect Molecular Biology, vol. 15, Issue 5, Oct. 2006, The Royal Entomological Society, pp. 315-636.

Coelho, Joseph R., "Heat Transfer and Body Temperature in Honey Bee (Hymenoptera: Apidae) Drones and Workers," Environmental Entomology, vol. 20, Issue 6, Dec. 1991, Entomological Society of America, pp. 1627-1635.

Collins, Anita, M. et al., "Performance of honey bee (Apis mellifera) queens reared in beeswax cells impregnated with coumaphos," Journal of Apicultural Research, vol. 43, Issue 3, Jul. 1, 2004, IBRA, pp. 128-134.

Cornman, Robert Scott et al., "Pathogen Webs in Collapsing Honey Bee Colonies," PloS One, vol. 7, Issue 3, Aug. 2012, www.plosone.org, pp. 1-15.

Cornman, Robert Scott et al., "Population-genomic variation within RNA viruses of the Western honey bee, Apis mellifera, inferred from deep sequencing," BMC Genomics, vol. 14, Issue 154, 2013, BioMed Central, http://Aww.biomedcentral.com/1471-2164/14/154, pp. 1-14.

Dox-Foster, Diana L. et al., "A Metagenomic Survey of Microbes in Honey Bee Colony Collapse Disorder," Science, vol. 318, Issue 283, Oct. 12, 2007, American Association for the Advancement of Science (AAAS), pp. 283-287.

Dahlgren, Lizette et al., "Comparative Toxicity of Acaricides to Honey Bee (Hymenoptera: Apidae) Workers and Queens," Journal of Economic Entomology, vol. 105, Issue 6, 2012, Entomological Society of America, pp. 1895-1902.

Dainat, Benjamin et al., "Predictive Markers of Honey Bee Colony Collapse," PLoS ONE, vol. 7, Issue 2, Feb. 23, 2012, www.plosone.org, pp. 1-9.

De Guzman, Lilia I. et al., "Hygienic Behavior by Honey Bees From Far-eastern Russia," American Bee Journal, vol. 142, Issue 1, Jan. 2002, pp. 58-60.

De Jong, D. et al., "Weight loss and other damage to developing worker honeybees from infestation with Varroa Jacobsoni," Journal of Apicultural Research, vol. 21, Issue 3,1982, Taylor & Francis, pp. 165-167.

Dekeyser, Mark A. et al., "Biochemical and Physiological Targets for Miticides," Pesticide Science, vol. 40, Bsue 2, 1994, SCI, pp. 85-101.

Delaplane, Keith S. et al., "Standard methods for estimating strength parameters of Apis mellifera colonies," Journal of Apicultural Research, vol. 52, Issue 1, Oct. 22, 2012, IBRA, pp. 1-12.

De Miranda, Joachim R. et al., "Standard methods for virus research in Apis mellifera," Journal of Apicultural Research, vol. 52, Issue 4, 2013, IBRA, pp. 1-55.

Desai, S. D. et al., "Reduction in deformed wing virus infection in larval and adult honey bees (Apis mellifera L.) by Jouble-stranded RNA ingestion," Insect Molecular Biology, vol. 21, Issue 4, Jun. 12, 2012, The Royal Entomological Society, pp. 446-455.

Desneux, Nicolas et al., "The Sublethal Effects of Pesticides on Beneficial Arthropods," Annual Review of Entomology, vol. 52, 2007, Annual Reviews, pp. 81-106.

Dietemann, Vincent et al., "Standard methods for varroa research," Journal of Apicultural Research, vol. 52, Issue 1, Nov. 14, 2012, IBRA, pp. 1-54.

Dietemann, Vincent et al., "Varroa destructor: research avenues towards sustainable control," Journal of Apicultural Research, vol. 51, Issue 1, Dec. 20, 2011, IBRA, pp. 125-132.

Di Prisco, Gennaro et al., "Dynamics of Persistent and Acute Deformed Wing Virus Infections in Honey Bees, Apis mellifera," Viruses, vol. 3, Issue 12, Dec. 14, 2011, http://www.mdpi.com/journal/viruses, pp. 2425-2441.

Di Prisco, Gennaro et al., "Varroa destructor is an effective vector of Israeli acute paralysis virus in the honeybee, Apis mellifera," Journal of General Virology, vol. 92, 2011, Microbiology Society, pp. 151-155.

Dunkelblum, E. et al., "Double-bond Location in Monounsaturated Fatty Acids by Dimethyl Disulfide Derivatization and Mass Spectrometry: Application to Analysis of Fatty Acids in Pheromone Glands of Four Lepidoptera," Journal of Chemical Ecology, vol. 11, Issue 3, 1985, Plenum Publishing Corporation, pp. 265-277.

Eliyahu, Dorit et al., "Unusual macrocyclic lactone sex pheromone of Parcoblatta lata, a primary food source of the endangered red-cockaded woodpecker," Proceedings of the National Academy of Sciences (PNAS), vol. 109, Bsue 8, Feb. 2012, National Academy of Sciences, pages E490-E496.

Elsik, Christine G et al., "Finding the missing honey bee genes: lessons learned from a genome upgrade," BMC Genomics, vol. 15, Issue 86, 2014, BioMed Central, http://www.biomedcentral.com/1471-2164/15/86, pp. 1-29.

Espinosa-Montano, Laura G et al. "Comparative study of three assays to evaluate hygienic behavior in honey bee (Apis meiiifera L.) colonies," Veterinaria Mexico, vol. 39, Issue 1, Mar. 2008, Universidad Nacional Autonoma de Mexico, pp. 39-53.

Evans, Jay D., "Beepath: An ordered quantitative-PCR array for exploring honey bee immunity and disease," Journal of Invertebrate Pathology, vol. 93, Issue 2, Oct. 2006, Elsevier Inc., pp. 135-139.

Evans, Jay D., "Diverse origins of tetracycline resistance in the honey bee bacterial pathogen Paenibacillus larvae," Journal of Invertebrate Pathology, vol. 83, Issue 1, May 2003, Elsevier Science, pp. 46-50.

Evans, J.D et al., "Immune pathways and defence mechanisms in honey bees Apis mellifera," Insect Molecular Biology, vol. 15, Issue 5, Oct. 2006, The Royal Entomological Society, pp. 645-656.

(56) References Cited

OTHER PUBLICATIONS

Fakhimzadeh, Kamran, "Effectiveness of confectioner sugar dusting to knock down Varroa destructor from adult honey bees in laboratory trials," Apidologie, vol. 32, Issue 2, March-Apr. 2001, INRA/DIB-AGIB/EDP Sciences, pp. 139-148.

Ferreira-Caliman, M.J et al., "Analysis of Insect Cuticular Compounds by Non-lethal Solid Phase Micro Extraction with Styrene-Divinylbenzene Copolymers," Journal of Chemical Ecology, vol. 38, Issue 4, Apr. 2012, Springer Science+Business Media, LLC, pp. 418-426.

Flenniken, Michelle L et al., "Non-Specific dsRNA-Mediated Antiviral Response in the Honey Bee," PLoS ONE, vol. 8, Issue 10, Oct. 10, 2013, www plosone.org, pp. 1-16.

Forkpah, Cordelia et al., "Xenobiotic Effects on Intestinal Stem Cell Proliferation in Adult Honey Bee (Apis mellifera L) Workers," PLoS ONE, vol. 9, Issue 3, Mar. 7, 2014, www.plosone org, 9 pages.

Frazier, Maryann et al., "What Have Pesticides Got to Do with It?" American Bee Journal, vol. 148, Issue 6, Jun. 2008, American Bee Journal, pp. 1-5.

Frey, Eva et al., "Activation and interruption of the reproduction of Varroa destructor is triggered by host signals (Apis mellifera)," Journal of Invertebrate Pathology, vol. 113, Issue 1, May 2013, Elsevier Inc., pp. 56-62.

Furman, David et al., "Cytomegalovirus infection improves immune responses to influenza," Science Translational Medicine, vol. 7, Issue 281, Apr. 1, 2015, American Association for the Advancement of Science, pp. 1-22.

Galbraith, David A et al., "Parallel Epigenomic and Transcriptomic Responses to Viral Infection in Honey Bees Apis mellifera)," PLOS Pathogens, vol. 11, Issue 3, Mar. 26, 2015, https://www.ncbi.nlm.nih.gov/pmc/articles/PMC4374888/, pp. 1-24.

Garbian, Yael et al., "Bidirectional Transfer of RNAi between Honey Bee and Varroa destructor: Varroa Gene Silencing Reduces Varroa Population," PLOS Pathogens, vol. 8, Issue 12, Dec. 2012, www.plospathogens. org, pp. 1-9.

3Aredew, Assegid et al., "The energy and nutritional demand of the parasitic life of the mite Varroa destructor," Apidologie, vol. 35, Issue 4, July-Aug. 2004, Inra/Dib-Agib/ Edp Sciences, pp. 419-430.

3Enersch, Elke et al., "Emerging and re-emerging viruses of the honey bee (Apis mellifera L.)," Veterinary Research, vol. 41, Issue 6, 2010, EDP Sciences, pp. 1-20.

3Enersch, Elke, "Honey bee pathology: current threats to honey bees and beekeeping," Applied Microbiology and Biotechnology, vol. 87, Issue 1, Apr. 17, 2010, Springer-Verlag, pp. 87-97.

3Illespie, Jeremy p et al., "Biological Mediators of Insect Immunity," Annual Review of Entomology, vol. 42, Bsue 1, 1997, Annual Reviews, pp. 611-643.

Genersch, Elke et al., "The German bee monitoring project: a long term study to understand periodically high winter losses of honey bee colonies," Apidologie, vol. 41, Issue 3, May-Jun. 2010, INRA/DIB-AGIB/EDP Sciences, pp. 1-21.

Ginzel, Matthew D et al., "(Z)-9-Nonacosene-Major Component of the Contact Sex Pheromone of the Beetle Megacyllene caryae," Journal of Chemical Ecology, vol. 32, Issue 2, Feb. 2006, Springer Science + Business Media, Inc., pp. 435-451.

Goode, Katarzyna et al., "Hygienic behavior of the honey bee (Apis mellifera) is independent of sucrose Yesponsiveness and foraging ontogeny," Hormones and Behavior, vol. 49, Issue 3, Mar. 2006, Elsevier Inc., pp. 391-397.

Goulson, Dave et al., "Bee declines driven by combined stress from parasites, pesticides, and lack of flowers," Science, vol. 347, Issue 6229, Mar. 27, 2015, American Association for the Advancement of Science (AAAS), 11 pages.

Goulson, Dave et al., "Combined stress from parasites, pesticides and lack of flowers drives bee declines," Science, vol. 347, Issue 6229, Feb. 2015, American Association for the Advancement of Science, pp. 1-30.

Granberg, Fredrik et al., "Metagenomic Detection of Viral Pathogens in Spanish Honeybees: Co-lnfection by Aphid Lethal Paralysis, Israel Acute Paralysis and Lake Sinai Viruses," Plos One, vol. 8, Issue 2, Feb. 2013, vww.plosone.org, pp. 1-8.

Gregorc, Ales et al., "Gene expression in honey bee (Apis mellifera) larvae exposed to pesticides and Varroa mites (Varroa destructor)," Journal of Insect Physiology, vol. 58, Issue 8, 2012, Elsevier Ltd., pp. 1042-1049.

Gregory, Pamela G et al., "Conditional immune-gene suppression of honeybees parasitized by Varroa mites," Journal of Insect Science, vol. 5, Issue 7, Mar. 25, 2005, Oxford University Press, insectscience.org/5.7, pp. 1-5.

Haarmann, Timothy et al., "Effects of Fluvalinate and Coumaphos on Queen Honey Bees (Hymenoptera: Apidae) n Two Commercial Queen Rearing Operations," Journal of Economic Entomology, vol. 95, Issue 1, Feb. 2002, Entomological Society of America, pp. 28-35.

Harbo, John R. et al., "Resistance to Varroa destructor (Mesostigmata: Varroidae) When Mite-Resistant Queen Honey Bees (Hymenoptera: Apidae) Were Free-Mated with Unselected Drones," Journal of Economic Entomology, vol. 94, Issue 6, Dec. 2001, Entomological Society of America, pp. 1319-1323.

Harbo, John R. et al., "Responses to Varroa by honey bees with different levels of Varroa Sensitive Hygiene," Journal of Apicultural Research and Bee World, vol. 48, Issue 3, 2009, IBRA, pp. 156-161.

Harbo, John R. et al., "Suppressed mite reproduction explained by the behaviour of adult bees," Journal of Apicultural Research, vol. 44, Issue 1, 2005, IBRA, pp. 21-23.

Harris, Jeffrey W., "Bees with Varroa Sensitive Hygiene preferentially remove mite infested pupae aged < five Tays post capping," Journal of Apicultural Research, vol. 46, Issue 3,2007, IBRA, pp. 134-139.

Harris, Jeffrey W. et al., "Changes in Infestation, Cell Cap Condition, and Reproductive Status of Varroa Iestructor (Mesostigmata: Varroidae) in Brood Exposed to Honey Bees with Varroa Sensitive Hygiene," Annals of the Entomological Society of America, vol. 105, Issue 3, May 2012, Entomological Society of America, pp. 512-518.

Harris, Jeffrey W., "Effect of Brood Type on Varroa-Sensitive Hygiene by Worker Honey Bees (Hymenoptera Apidae)," Annals of the Entomological Society of America, vol. 101, Issue 6, 2008, pp. 1137-1144.

Harris, Jeffery et al., "Selecting for Varroa Sensitive Hygiene," Bee Health, Nov. 12, 2010, http://articles. 2xtension.org/pages/30984/selecting-for-varroa-sensitive-hygiene, extension, 4 pages.

Harris, Jeffrey et al., "Varroa Sensitive Hygiene and Mite Reproduction," Bee Health, Dec. 13, 2013, http://articles.extension.org/pages/30361/varroa-sensitive-hygiene-and-mite-reproduction, 5 pages.

Hawthorne, David J. et al., "Killing Them with Kindness? In-Hive Medications May Inhibit Xenobiotic Efflux Transporters and Endanger Honey Bees," PLoS ONE, vol. 6, Issue 11, Nov. 2, 2011, www.plosone.org, pp. 1-6.

Herrmann, Matthias et al., "Survival of honey bee (Apis mellifera) pupae after trypan blue staining of wounds caused by Varroa destructor mites or arlificial perforation," Apidologie, vol. 36, Issue 1, Mar. 16, 2005, Inra/Dib-Agib/ Edp Sciences, pp. 107-111.

Higes, Mariano et al., "How natural infection by Nosema ceranae causes honeybee colony collapse," Environmental Microbiology, vol. 10, Issue 10, 2008, Society for Applied Microbiology and Blackwell Publishing _td., pp. 2659-2669.

USPTO, Non-Final Rejection in U.S. Appl. No. 15/742,072 dated May 17, 2019.

* cited by examiner

SYNERGISTIC MIXTURE FOR INDUCING HYGIENIC BEHAVIOR IN HONEY BEES, AND RELATED COMPOSITIONS AND METHODS

CROSS REFERENCE TO RELATED APPLICATIONS

This application is a continuation application of Patent Cooperation Treaty Application No. PCT/US2020/027564 filed Apr. 9, 2020, which claims priority to U.S. Provisional Patent Application No. 62/831,277 filed on Apr. 9, 2019. The contents of each are hereby incorporated by references in their entirety.

STATEMENT REGARDING FEDERALLY SPONSORED RESEARCH OR DEVELOPMENT

This invention was made with government support under Grant No. 2017-68004-26321 awarded by the National Institute of Food and Agriculture, an agency within the United States Department of Agriculture. The government has certain rights in the invention.

FIELD

The inventions relate to the fields of agriculture, apiculture and hygienic behavior in honey bees.

BACKGROUND

Honey bees are the most important commercial pollinator world-wide for agricultural production and food security. Agriculture depends on animal pollination for over 100 different crops that provide >30% of the human diet and also supply fiber, fuel, and drugs. Honey bees are responsible for 80% of managed insect pollination and their economic impact on U.S. food crops in the year 2000 has been estimated to be $14.6 billion. However, honey bees and other insect pollinators suffer from a combination of factors, including habitat loss, pesticide exposure, pathogens, and stress due to active management. Recently, honey bee health has been marked with sharp declines and losses of colonies, with reports of "colony collapse disorder." The failure to identify a single factor as the cause of colony collapse disorder indicates that the global honey bee health crisis is complex and heterogeneous: Multiple stressors may act synergistically to lead to symptomatic health declines and colony failure and the causes may vary in time and between locations.

While no single factor has been identified as the cause of colony collapse disorder, the introduction and spread of parasites and associated pathogens and pesticide exposure have a central role in the health decline of honey bees. Disease control in the honey bee is crucial because it remains the most important commercial pollinator worldwide and its pollination services are irreplaceable in many agricultural systems. Moreover, honey bees are significant pollinators in natural ecosystems and are potential vectors of diseases that threaten native pollinator communities.

The ectoparasitic mite *Varroa destructor* in particular is a threat to honey bee health and apiculture today. *Varroa* are obligate honey bee parasites, requiring honey bee colonies for their own reproductive success. Mature, fertilized *Varroa* females enter a brood cell to lay eggs, and both the *Varroa* female and its offspring feed on the brood. *Varroa* causes physical and physiological damage when feeding on the brood. *Varroa* is a vector of viruses and has been associated with viral amplification and honey bee disease susceptibility. Pesticides are problematic because of toxicity to honey bees, beekeepers, and crops; general ecosystem pollution; and resistance development in *Varroa*.

*Varroa* is conventionally treated with synthetic acaricides, most notably coumaphos, tau-fluvalinate, flumethrin, and amitraz. These substances are toxic and persistent and may accumulate in the hive, consequently harming honey bee health. For example, miticides fluvalinate and coumaphos, have been found to have lethal and sublethal effects on honey bee queens, workers, and drones. Moreover, resistance build-up in resident *Varroa* populations decreases the efficacy of chemical control. Synergistic effects of fluvalinate and coumaphos have been measured, where the toxicity of each chemical is significantly increased in bees previously exposed to the other. Furthermore, immunosuppression caused by chemical exposure makes honey bees more susceptible to parasites like *Varroa*, as well as to the pathogens they vector. In addition to affecting honey bee health, miticides compromise beekeeper health, enter bee products including those consumed by humans and contribute to general ecosystem pollution.

Other control strategies such as physical mite removal and use of organic acids and essential oils have been proposed as alternatives, but have many limitations that compromise efficacy, such as the labor-intensive application, temperature-sensitivity, and potential side-effects on honey bees. Despite substantial evidence of the need, no adequate solution for control of *Varroa* has been developed.

Traditional efforts to keep honey bees healthy have focused on management techniques and treatments (primarily chemotherapies). These treatments may lead to a loss of honey, are expensive and labor-intensive, and pose human health risks. Moreover, their long-term efficacy is questionable: None of the honey bee diseases have been eradicated due to past management. On the contrary, a steady emergence of novel pests and pathogens can be observed.

Beekeepers have selectively bred honey bees for hygienic behavior as an alternative. The mechanism for hygienic behavior is not completely understood, but the trait can be measured, for instance, by frequency of certain behaviors in honey bees. Minnesota Hygienic (HYG) is a breed of honey bees based on the high frequency of honey bee removal of freeze-killed brood (FKB). A circle of brood is frozen with liquid nitrogen and percent removal of the killed brood is recorded, thus assessing the effectiveness of the general detection and removal of dead brood. However, the olfactory trigger for hygienic removal of mite-infested and other live brood may be significantly lower than that of dead brood. HYG breeding relies on olfactory triggers of dead brood and results in bred honey bees that may lack sufficient sensitivity to living diseased brood. Another example is *Varroa* Sensitive Hygienic (VSH), which is a breed of honey bees based on measured changes in mite removal and/or mite reproduction. VSH breeding is based on a more narrowly defined goal but hygienic behavior may just be one mechanism for these bees to suppress mite reproduction. It has been unclear whether VSH bees are truly distinct or whether suppression of mite reproduction is due to the interruption of the mite reproductive cycle by hygienic removal of infested brood. While the HYG and VSH hygienic honey bee colonies exhibit reduced mite and disease loads compared to unselected hives, the selective breeding programs are not widely adopted by beekeepers due to lack of specificity, difficulty and expense of current selection assays. Also, hygienic lines do not yet serve as complete alternatives to chemical *Varroa* control, as chemical treatments are sometimes required to control severe mite infestations in hygienic hives.

Moreover, despite the presence of natural honey bee social immune mechanisms like hygienic behavior, honey bee health is currently being severely threatened. Following global pollinator population trends, managed honey bee colonies in the United States have declined steadily for over six decades, from 5.9 million colonies in 1947 to 2.4 million colonies in 2005. Total annual colony losses in the United States have exceeded 33% in four of the last five years, exceeding 45% between April 2012 and April 2013. Honey bee losses are largely attributed to introduction and spread of new parasites and associated pathogens, and to lethal and sublethal effects of agrochemical exposure.

The long-term sustainability of apiculture depends on the balance between the benefit of honey bee keeping to the individual and the costs of honey bee management and losses. There remains a need for improving selection of honey bees for hygienic behavior and use of hygienic behavior by honey bees to prevent or treat a diseased honey bee colony to ensure adequate supplies of managed pollinators for agriculture. U.S. Pat. Nos. 10,512,251 and 10,524,455 disclose tritriacontene compositions and methods for inducing hygienic behavior. However, there remains a need for further improvement.

SUMMARY OF THE INVENTION

The presently disclosed subject matter describes synergistic mixtures for inducing hygienic behavior in honey bees, compositions for inducing hygienic behavior in honey bees, and methods of inducing hygienic behavior in honey bees.

In an embodiment, a synergistic mixture for inducing hygienic behavior in honey bees comprises from about 0.1 to about 1% by weight of Compound (I) having the structure:

from about 0.1 to about 1% by weight of Compound (II) having the structure:

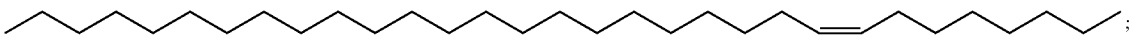 [SMILES: CCCCCCC/C=C\CCCCCCCCCCCCCCCCCCCCCC]

from about 0.1 to about 1% by weight of Compound (III) having the structure:

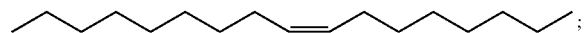 [SMILES: CCCCCCC/C=C\CCCCCCCC]

and from about 0.1 to about 1% by weight of Compound (IV) having the structure:

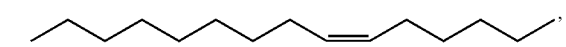

or agriculturally acceptable derivatives thereof.

In an embodiment, a composition for inducing hygienic behavior in honey bees comprises the synergistic mixture and an agriculturally acceptable diluent or carrier. In an embodiment, a method of inducing hygienic behavior in honey bees comprises contacting hive cells with the composition. In an embodiment, the hygienic behavior comprises eating diseased brood, eating diseased honey bees, removing diseased brood from hive cells, removing diseased honey bees from hive cells, removing pests or parasites, uncapping hive cells, or uncapping and recapping hive cells. In an embodiment, the hygienic behavior comprises uncapping the contacted hive cells and removing pests or parasites. In an embodiment, the hygienic behavior results in suppression of mite reproduction, decreased mite survival, or suppression of a mite infestation. In an embodiment, the hive cells are capped hive cells or uncapped hive cells. In an embodiment, the diseased brood or diseased honey bees are infested with pests or parasites; infected with a pathogen; or damaged.

In an embodiment, a synergistic mixture for inducing hygienic behavior in honey bees consists essentially of:

Compound (I) having the structure:

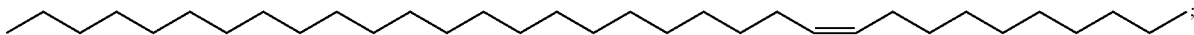 [SMILES: CCCCCCCCC/C=C\CCCCCCCCCCCCCCCCCCCCCC]

Compound (II) having the structure:

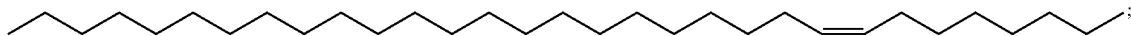 [SMILES: CCCCCCC/C=C\CCCCCCCCCCCCCCCCCCCCCC]

Compound (III) having the structure:

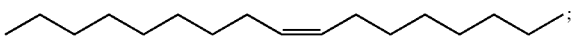 [SMILES: CCCCCCC/C=C\CCCCCCCC]

and
Compound (IV) having the structure:

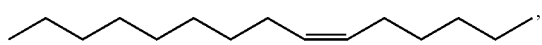

or agriculturally acceptable derivatives thereof.

In an embodiment, a composition for inducing hygienic behavior in honey bees comprises the synergistic mixture and an agriculturally acceptable diluent or carrier. In an embodiment, a method of inducing hygienic behavior in honey bees comprises contacting hive cells with the composition. In an embodiment, the hygienic behavior comprises eating diseased brood, eating diseased honey bees, removing diseased brood from hive cells, removing diseased honey bees from hive cells, removing pests or parasites, uncapping hive cells, or uncapping and recapping hive cells. In an embodiment, the hygienic behavior comprises uncapping the contacted hive cells and removing pests or parasites. In an embodiment, the hygienic behavior results in suppression of mite reproduction, decreased mite survival, or suppression of a mite infestation. In an embodiment, the hive cells are capped hive cells or uncapped hive cells. In an embodiment, the diseased brood or diseased honey bees are infested with pests or parasites; infected with a pathogen; or damaged.

In an embodiment, a synergistic mixture for inducing hygienic behavior in honey bees consists of:
Compound (I) having the structure:

Compound (II) having the structure:

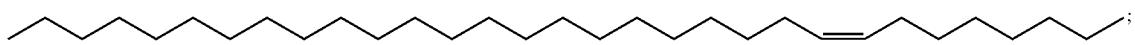 [SMILES: CCCCCCC/C=C\CCCCCCCCCCCCCCCCCCCCCC]

Compound (III) having the structure:

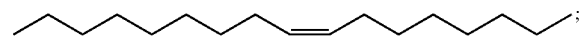 [SMILES: CCCCCCC/C=C\CCCCCCCC]

Compound (IV) having the structure:

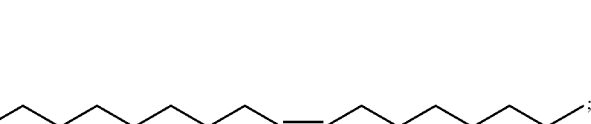

or agriculturally acceptable derivatives thereof.

In an embodiment, a composition for inducing hygienic behavior in honey bees comprises the synergistic mixture and an agriculturally acceptable diluent or carrier. In an embodiment, a method of inducing hygienic behavior in honey bees comprises contacting hive cells with the composition. In an embodiment, the hygienic behavior comprises eating diseased brood, eating diseased honey bees, removing diseased brood from hive cells, removing diseased honey bees from hive cells, removing pests or parasites, uncapping hive cells, or uncapping and recapping hive cells. In an embodiment, the hygienic behavior comprises uncapping the contacted hive cells and removing pests or parasites. In an embodiment, the hygienic behavior results in suppression of mite reproduction, decreased mite survival, or suppression of a mite infestation. In an embodiment, the hive cells are capped hive cells or uncapped hive cells. In an embodiment, the diseased brood or diseased honey bees are infested with pests or parasites; infected with a pathogen; or damaged.

BRIEF DESCRIPTION OF THE FIGURES

Reference will now be made to the accompanying Figures, which are not necessarily drawn to scale, and wherein.

DETAILED DESCRIPTION

Figure 1:
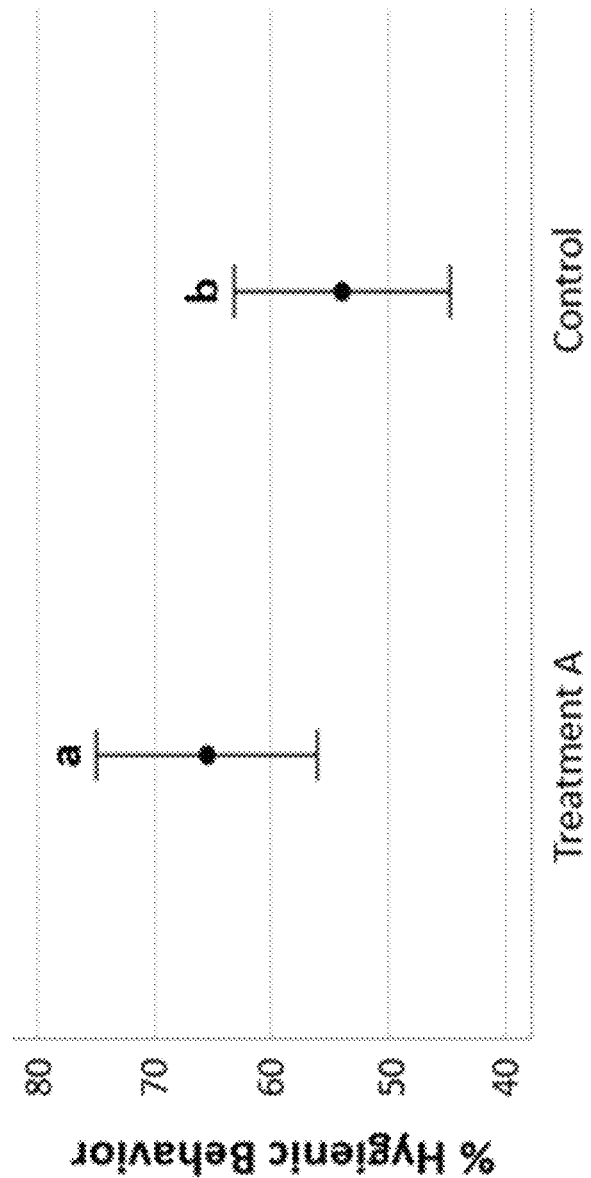
FIG. 1 is a graph representing results from an induced hygienic behavior assay, and in particular, the percent hygienic behavior, as shown by 2-hour uncapping, removal, or uncapping and removal, resulting from application of Treatment A and the Control (comprising a mixture of structurally-similar chemicals) to cell caps. Treatment (A): A solution comprising 0.50% concentration of each of the following compounds in hexane: Compound (I), Compound (II), Compound (III), and Compound (IV). A control solution was prepared comprising 0.50% concentration of each of the following compounds in hexane: Compound (V), Compound (VI), Compound (VII), Compound (VIII). Chemicals used for the control assay were similar in structure to those compounds in Treatment (I).

The presently disclosed subject matter now will be described more fully hereinafter with reference to the accompanying Figures, in which some, but not all embodiments of the presently disclosed subject matter are shown. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

Unless defined otherwise, all technical and scientific terms used herein have the same meanings as commonly understood by one of ordinary skill in the art to which this disclosure belongs. Preferred methods, devices, and materials are described, although any methods and materials similar or equivalent to those described herein can be used in the practice or testing of the present disclosure.

Throughout the present specification, numerical ranges are provided for certain quantities. It is to be understood that these ranges comprise all subranges therein. Thus, the range "from 50 to 80" includes all possible ranges therein (e.g., 51-79, 52-78, 53-77, 54-76, 55-75, 60-70, etc.). Furthermore, all values within a given range may be an endpoint for the range encompassed thereby (e.g., the range 50-80 includes the ranges with endpoints such as 55-80, 50-75, etc.).

The presently disclosed subject matter describes synergistic mixtures for inducing hygienic behavior in honey bees, compositions for inducing hygienic behavior in honey bees, and methods of inducing hygienic behavior in honey bees. The range encompassed by the term "about" is informed by the context of the specification and claims, which both describe the range of specific activity covered by the term "about," i.e. inducing hygienic behavior in honey bees.

The mixture of Compounds (I)-(IV), in any one of the embodiments described herein, displays a synergistic effect when applied in combination; that is, the compounds are more effective in combination than when applied individually. The synergistic mixture of Compounds (I)-(IV) is capable of triggering honey bees to exhibit hygienic behavior when the mixture is in contact with hive cells.

Compounds (I)-(IV) are cuticular hydrocarbons of honeybee brood. (Z)-10-tritriacontene has previously been shown to induce hygienic behavior in honey bees. See U.S. Patent Application Publication No. US 2018/0177160. (Z)-6-pentadecene has previously been shown to induce hygienic behavior in honey bee. See Francesco Nazzi, Giorgio Della Vedova, Mauro D'Agaro. A semiochemical from brood cells infested by *Varroa destructor* triggers hygienic behaviour in *Apis mellifera*. Apidologie, Springer Verlag, 2004, 35 (1), pp. 65-70. However, honey bee extracts are not likely to have Compounds (I)-(IV) present in synergistic amounts, or in amounts that represent original relative quantities as present on the honey bee. There is a current lack of methodology to identify natural CHC profiles that are representative of original relative quantities as present on the honey bee. Known extraction methods efficiently collect only either non-volatile/larger hydrocarbons or volatile/small hydrocarbons. For example, Compounds (III) and (IV) are relatively small hydrocarbons and, even if extracted initially, are quite volatile. In the process of concentrating the samples for analysis, these two chemicals volatilize, and are no longer present for quantification at their original concentrations when the sample is run through the GCMS. Thus, honey bee extracts would not have each of Compounds (I)-(V) in active or synergistically effective amounts. In Nazzi et al. Journal of Chemical Ecology, Vol. 28, No. 11, November 2002, trace amounts of C15 were found, and Compound C17 was only 0.15% of the total (see table 3). Moreover, this extract was processed with at least one evaporation step under nitrogen, and so the relative quantity of small chemicals to big chemicals in the extract is not an accurate representation of their quantities on the honey bee. In Nazzi et al. (2002) and Nazzi et al. (Apidologie, Springer Verlag, 2004, 35 (1), pp. 65-70.), SPME was also used. While SPME analysis provides a better method for collecting volatiles, it is not useful for collecting larger chemicals such as Compounds (I) and (II). For example, the 100 m, polydimethylsiloxane SPME fiber used by Nazzi in both the 2002 and 2004 papers is only designed for molecular weights between 60 and 275 (and the molecular weights of C15, C17, C31 and C33 monoalkenes are roughly 210, 239, 434, and 463 g/mol, respectively). In DelPiccolo et al. (Parasitology (2010), 137, 967-973.), C17 was found in the hexane extracts, but these were from adult bees, so presumably the amount there to begin with was larger (and still what they were able to detect was only 0.001-0.011% of the extractable surface hydrocarbons—see Table 2). However, even though they found it, the amount is not comparable to the larger hydrocarbons because of the step "The extract was then reduced under nitrogen to 10 ml" (see Extraction of honeybee cuticular hydrocarbons in the methods section). The "reduced under nitrogen" step is an evaporative step, which means volatiles like C17 are lost in the process.

In an embodiment, a synergistic mixture for inducing hygienic behavior in honey bees comprises from about 0.1 to about 1% by weight of Compound (I) having the structure:

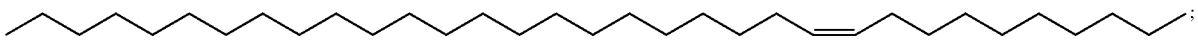 [SMILES: CCCCCCCCC/C=C\CCCCCCCCCCCCCCCCCCCCCC]

from about 0.1 to about 1% by weight of Compound (II) having the structure:

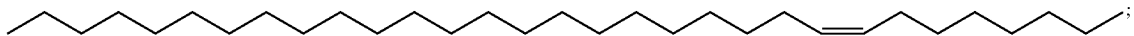 [SMILES: CCCCCCC/C=C\CCCCCCCCCCCCCCCCCCCCCC]

from about 0.1 to about 1% by weight of Compound (III) having the structure:

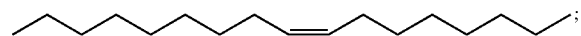

and from about 0.1 to about 1% by weight of Compound (IV) having the structure:

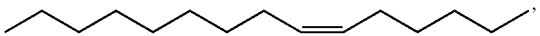

or agriculturally acceptable derivatives thereof.

In an embodiment, a synergistic mixture for inducing hygienic behavior in honey bees comprises from about 0.1% to about 1% by weight of Compound (I) having the structure:

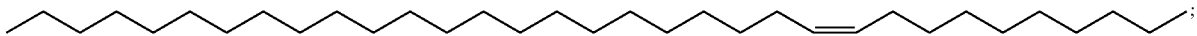

from about 0.1 to about 1% by weight of Compound (II) having the structure:

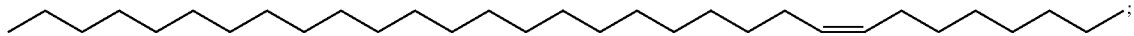 [SMILES: CCCCCCC/C=C\CCCCCCCCCCCCCCCCCCCCCC]

from about 0.1% to about 2% by weight of Compound (III) having the structure:

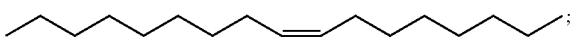 [SMILES: CCCCCCC/C=C\CCCCCCCC]

and from about 0.1% to about 2% by weight of Compound (IV) having the structure:

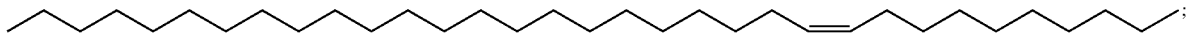 [SMILES: CCCCCCCCC/C=C\CCCCCCCCCCCCCCCCCCCCCC]

or agriculturally acceptable derivatives thereof.

In an embodiment, a synergistic mixture for inducing hygienic behavior in honey bees comprises from about 0.01% to about 1% by weight of Compound (I) having the structure:

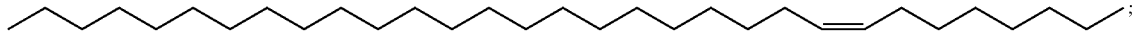 [SMILES: CCCCCCC/C=C\CCCCCCCCCCCCCCCCCCCCCC]

from about 0.1 to about 1% by weight of Compound (II) having the structure:

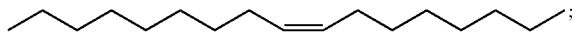

from about 0.1% to about 2% by weight of Compound (III) having the structure:

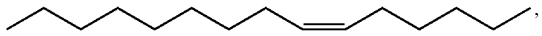

and from about 0.1 to about 1% by weight of Compound (IV) having the structure:

or agriculturally acceptable derivatives thereof.

In an embodiment, a synergistic mixture for inducing hygienic behavior in honey bees.

comprises from about 0.01% to about 1% by weight of Compound (I) having the structure:

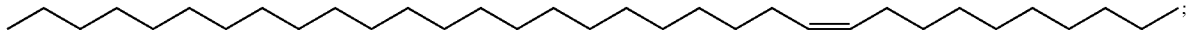

from about 0.01% to about 1% by weight of Compound (II) having the structure:

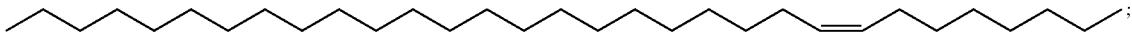

from about 0.1% to about 2% by weight of Compound (III) having the structure:

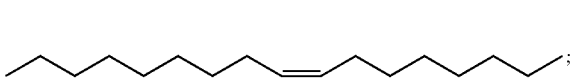 [SMILES: CCCCCCC/C=C\CCCCCCCC]

and
from about 0.1% to about 2% by weight of Compound (IV) having the structure:

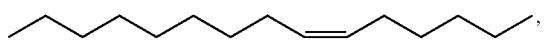

or agriculturally acceptable derivatives thereof.

In an embodiment, a composition for inducing hygienic behavior in honey bees comprises any one of the synergistic mixtures and an agriculturally acceptable diluent or carrier. In an embodiment, a method of inducing hygienic behavior in honey bees comprises contacting hive cells with the composition. In an embodiment, the hygienic behavior comprises eating diseased brood, eating diseased honey bees, removing diseased brood from hive cells, removing diseased honey bees from hive cells, removing pests or parasites, uncapping hive cells, or uncapping and recapping hive cells. In an embodiment, the hygienic behavior comprises uncapping the contacted hive cells and removing pests or parasites. In an embodiment, the hygienic behavior results in suppression of mite reproduction, decreased mite survival, or suppression of a mite infestation. In an embodiment, the hive cells are capped hive cells or uncapped hive cells. In an embodiment, the diseased brood or diseased honey bees are infested with pests or parasites; infected with a pathogen; or damaged.

In an embodiment, a synergistic mixture for inducing hygienic behavior in honey bees consists essentially of:
Compound (I) having the structure:

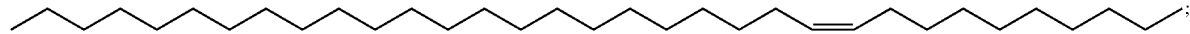

Compound (II) having the structure:

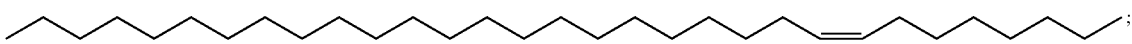

Compound (III) having the structure:

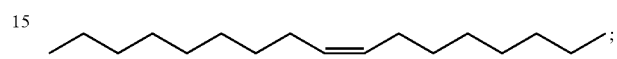

and
Compound (IV) having the structure:

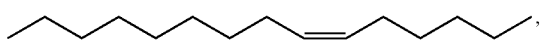

or agriculturally acceptable derivatives thereof.

The synergistic mixture is limited to the recited compounds and other component(s) or ingredient(s) that do not materially affect the basic and novel characteristics of the synergistic mixture. The basic and novel characteristics include the synergistic effect when Compounds (I)-(IV) are applied in combination. The compounds are more effective in combination than when applied individually. For example, the addition of another hydrocarbon to the mixture would materially affect the basic and novel characteristic of the synergistic mixture if the mixture of Compounds (I)-(IV) plus another hydrocarbon is no longer more effective in combination than when Compounds (I), (II), (III), or (IV) are applied individually. In an embodiment, a composition for inducing hygienic behavior in honey bees comprises the synergistic mixture and an agriculturally acceptable diluent or carrier. In an embodiment, a method of inducing hygienic behavior in honey bees comprises contacting hive cells with the composition. In an embodiment, the hygienic behavior comprises eating diseased brood, eating diseased honey bees, removing diseased brood from hive cells, removing diseased honey bees from hive cells, removing pests or parasites, uncapping hive cells, or uncapping and recapping hive cells. In an embodiment, the hygienic behavior comprises uncapping the contacted hive cells and removing pests or parasites. In an embodiment, the hygienic behavior results in suppression of mite reproduction, decreased mite survival, or suppression of a mite infestation. In an embodiment, the hive cells are capped hive cells or uncapped hive cells. In an embodiment, the diseased brood or diseased honey bees are infested with pests or parasites; infected with a pathogen; or damaged.

In an embodiment, a synergistic mixture for inducing hygienic behavior in honey bees consists of:
Compound (I) having the structure:

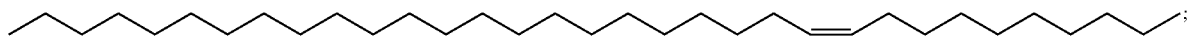

Compound (II) having the structure:

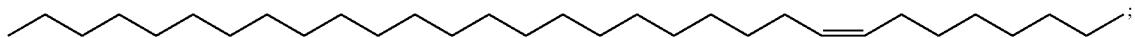

Compound (III) having the structure:

and
Compound (IV) having the structure:

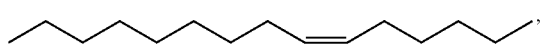

or agriculturally acceptable derivatives thereof.

In an embodiment, a composition for inducing hygienic behavior in honey bees comprises the synergistic mixture and an agriculturally acceptable diluent or carrier. In an embodiment, a method of inducing hygienic behavior in honey bees comprises contacting hive cells with the composition. In an embodiment, the hygienic behavior comprises eating diseased brood, eating diseased honey bees, removing diseased brood from hive cells, removing diseased honey bees from hive cells, removing pests or parasites, uncapping hive cells, or uncapping and recapping hive cells. In an embodiment, the hygienic behavior comprises uncapping the contacted hive cells and removing pests or parasites. In an embodiment, the hygienic behavior results in suppression of mite reproduction, decreased mite survival, or suppression of a mite infestation. In an embodiment, the hive cells are capped hive cells or uncapped hive cells. In an embodiment, the diseased brood or diseased honey bees are infested with pests or parasites; infected with a pathogen; or damaged.

In one embodiment, a mixture comprises 0.50% concentration of each of Compounds (I)-(IV). In one embodiment, the amount of the total active ingredients applied to hive cells is generally within the range of about 0.10 mg to about 0.30 mg per hive cell. In one embodiment, a mixture comprising Compounds (I)-(IV) comprises about 0.10 mg to about 0.30 mg of total active ingredients per hive cell to be treated. In one embodiment, the amount of each of the Compounds (I)-(IV) applied to hive cells is generally within the range of about 26,000 ng to about 76,500 ng per hive cell. In one embodiment, a mixture comprising Compounds (I)-(IV) comprises about 26,000 ng to about 76,500 ng of each of the Compounds (I)-(IV) per hive cell to be treated.

In one embodiment, a mixture comprises 0.167% concentration of each of Compounds (I)-(IV). In one embodiment, the amount of the total active ingredients applied to hive cells is generally within the range of about 0.02 mg to about 0.09 mg per hive cell. In one embodiment, a mixture comprising Compounds (I)-(IV) comprises about 0.02 mg to about 0.09 mg of total active ingredients per hive cell to be treated. In one embodiment, the amount of each of the Compounds (I)-(IV) applied to hive cells is generally within the range of about 4,500 ng to about 25,500 ng per hive cell. In one embodiment, a mixture comprising Compounds (I)-(IV) comprises about 4,500 ng to about 25,500 ng of each of the Compounds (I)-(IV) per hive cell to be treated.

In one embodiment, a mixture comprises 1.5% concentration of each of Compounds (I)-(IV). In one embodiment, the amount of the total active ingredients applied to hive cells is generally within the range of about 0.40 mg to about 0.60 mg per hive cell. In one embodiment, a mixture comprising Compounds (I)-(IV) comprises about 0.40 mg to about 0.60 mg of total active ingredients per hive cell to be treated. In one embodiment, the amount of each of the Compounds (I)-(IV) applied to hive cells is generally within the range of about 77,000 ng to about 229,500 ng per hive cell. In one embodiment, a mixture comprising Compounds (I)-(IV) comprises about 77,000 ng to about 229,500 ng of each of the Compounds (I)-(IV) per hive cell to be treated.

The exact amount of each of Compounds (I)-(IV) in the mixture and the rate at which the mixture or composition is applied can be dependent on several factors including, but not limited to, the particular action desired; the pathogen, disease, or pest to be controlled or treated against; the stage of growth thereof; the number of honey bees to be induced; the particular honey bee species; the particular honey bee breed; thresholds to avoid toxicity to the brood or hive generally; the type of formulation employed; and the method of application including, for example, dilution and rate of application and equipment employed; and/or climate conditions. The components of the synergistic mixture of the present invention can be applied either separately or as part of a multipart system.

The particular ratio of Compound (I):Compound (II):Compound (III):Compound (IV) and the corresponding amounts of each of Compounds (I)-(IV) can readily be determined by those skilled in the art. One skilled in the art could test a weight or concentration ratio of Compound (I):Compound (II):Compound (III):Compound (IV) and the corresponding amounts of each of Compounds (I)-(IV) individually against a control and reasonably ascertain whether the mixture demonstrates a synergistic effect for inducing hygienic behavior in honey bees when applied in combination (i.e. the compounds are more effective in combination than when applied individually). Moreover, because honey bees exhibit hygienic behavior in nature, testing against a control informs one skilled in the art about whether the synergistic mixture is actually inducing honey bee hygienic behavior.

One type of control would be a no treatment control. For example, comparison of hygienic removal rates between an area of capped brood treated with a composition comprising the synergistic mixture and an untreated area of capped brood can be used to differentiate between the effect of the applied amount of the synergistic mixture and the natural rate of hygienic behavior within a colony. A further control would be treatment with only a diluent or carrier. For example, any effect on hygienic removal of the agriculturally acceptable diluent or carrier for the synergistic mixture can be differentiated by a comparison of hygienic removal rates between an area of capped brood treated with the composition, and an area of capped brood treated with the diluent alone.

In one embodiment, one or more of the Compounds (I)-(IV) identified in the chart above is a stereoisomer, racemic mixture or optically active mixture. The various stereoisomers include geometric isomers/diastereomers (e.g. cis-isomers and trans-isomers, Z-isomers and E-isomers) and enantiomers; and refers to isomers that differ only in the way the atoms are arranged in space. It will be appreciated by those skilled in the art that one stereoisomer may be more active than the others. Individual stereoisomers and optically active mixtures may be obtained by selective synthetic procedures, by conventional synthetic procedures using resolved starting materials, or by conventional resolution procedures.

As used herein, in relation to the synergistic mixture of Compounds (I), (II), (III), (IV) disclosed herein, the term "an effective amount for inducing hygienic behavior in honey bees," has a plain and ordinary meaning, i.e. capable of triggering honey bees to exhibit hygienic behavior. The utility of the synergistic mixture is as a synthesized signal, and the term "hygienic behavior" provides context for what the response to that signal is.

As social insects, honey bees complement individual immunity with mechanisms of social immunity for defense against pathogens and parasites. Honey bees are able to reduce parasite and pathogen loads through age-specific sanitary activities such as hygienic behavior. The complete mechanism for hygienic behavior is not completely understood, but can be measured, for instance, by frequency of certain behaviors in honey bees, such as eating diseased brood or diseased honey bees, removing diseased brood or diseased honey bees from hive cells, removing pests or parasites, uncapping hive cells, or uncapping and recapping hive cells. See for example. [8, 9, 11] Hygienic behavior has been described by some as the detection, uncapping and/or removal of diseased brood from the hive. [182] As used herein, the term "hygienic behavior" includes those described herein and known in the art; for example, without limiting the foregoing, as described in Spivak, M., (1996) Honey bee hygienic behavior and defense against Varroa jacobsoni. Apidologie 27: 245-260.

In one embodiment, the hygienic behavior comprises eating diseased brood or diseased honey bees, removing diseased brood or diseased honey bees from hive cells, removing pests or parasites, uncapping hive cells, or uncapping and recapping hive cells. In another embodiment, the hygienic behavior comprises uncapping a hive cell, removing pests or parasites, and recapping the hive cell. In a further embodiment, the diseased brood or diseased honey bees are infested with a pest or parasite; infected with a pathogen; or damaged. In yet another embodiment the diseased brood are eggs, larvae, or pupae.

As used herein, the term "agriculturally acceptable derivative" refers to any agriculturally acceptable salt, ester, or salt of such ester, of such compound, or any other adduct or derivative which, upon administration, is capable of providing (directly or indirectly) a compound as otherwise described herein, or residue thereof. Materials and methods for derivatizing parent compounds are known and may be adapted to the present invention.

As used herein, the term "agriculturally acceptable salt," refers to salts of a free acid or a free base which are not biologically undesirable and are generally prepared by reacting the free base with a suitable organic or inorganic acid or by reacting the acid with a suitable organic or inorganic base. Agriculturally acceptable salts include salts, the cations or anions of which are known in the art for the formation of salts for agricultural or apicultural use. In some embodiments the salts are water-soluble. Suitable cations include the ions of the alkali metals (such as lithium, sodium and potassium), alkaline earth metals (such as calcium, magnesium and barium) and transition metals (such as manganese, copper, zinc and iron), and amines. Suitable anions of acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, such as formate, acetate, propionate and butyrate. The term "agriculturally acceptable ester" refers to those that are or can by hydrolyzed, oxidized, metabolized, or otherwise converted, e.g., in plants, water, or soil, to the corresponding carboxylic acid which, depending on the pH, may be in the dissociated or un-dissociated form. Exemplary esters include those derived from $C_1$-$C_{12}$ alkyl, $C_3$-$C_{12}$ alkenyl, $C_3$-$C_{12}$ alkynyl or $C_7$-$C_{10}$ aryl-substituted alkyl alcohols. Esters can be prepared by coupling of the acid with the alcohol using any number of suitable activating agents such as those used for peptide couplings such as dicyclohexylcarbodiimide (DCC) or carbonyl diimidazole (CDI); by reacting the acid with alkylating agents such as alkylhalides or alkylsulfonates in the presence of a base such as triethylamine or lithium carbonate; by reacting the corresponding acid chloride of an acid with an appropriate alcohol; by reacting the corresponding acid with an appropriate alcohol in the presence of an acid catalyst or by transesterification.

As used herein, the term "agriculturally acceptable diluent or carrier," refers to organic or inorganic material, natural or synthetic, that facilitates application and is agriculturally or apiculturally acceptable on the application surface; such as, adjuvants, mixers, enhancers, or combinations thereof suitable for application of the composition. Examples of suitable liquid agriculturally acceptable carriers include hexane, pentane, water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, and glycerine. Exemplary solid agriculturally acceptable carriers include talc, pyrophyllite clay, silica, attapulgus clay, kieselguhr, chalk, diatomaceous earth, lime, calcium carbonate, bentonite clay, Fuller's earth, cotton seed hulls, wheat flour, soybean flour, pumice, wood flour, walnut shell flour, and lignin. Additional adjuvants include antifoam agents, neutralizing agents, buffers, dispersing agents, thickening agents, sequestering agents, and so on.

The presently disclosed subject matter contemplates all vehicles by which the composition of the presently disclosed subject matter can be formulated for delivery and use as solutions, suspensions, emulsions, wettable powders and water dispersible granules, dry flowables, emulsifiable concentrates, granules, dusts, fumigants, gels, microencapsulations, and the like. The compositions can be manufactured in a manner known in the art; for example, without limiting the foregoing, by means of conventional mixing, dissolving, granulating, or emulsifying processes.

Formulations for application to hive cells may be applied following dilution of the concentrated formulation with water as aqueous solutions, suspensions or emulsions, or combinations thereof. Such solutions, suspensions or emulsions are produced from water-soluble, water-suspended or water-suspendable, water-emulsified or water-emulsifiable formulations or combinations thereof which are solids, including wettable powders or water dispersible granules; or liquids including emulsifiable concentrates, aqueous suspensions or suspension concentrates, and aqueous emulsions or emulsions in water, or mixtures thereof such as suspension-emulsions.

Wettable powders, which may be compacted to form water dispersible granules, comprise a mixture of the active ingredient, an inert carrier, and surfactants. The concentration of the active ingredient in the wettable powder is usually from about 10 percent to about 90 percent by weight based on the total weight of the wettable powder, more preferably about 25 weight percent to about 75 weight percent. In the preparation of wettable powder formulations, the active ingredients can be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the active ingredient comprise a concentration, such as from about 10 weight percent to about 50 weight percent of the active ingredient, in a suitable liquid, based on the total weight of the concentrate. The active ingredients are dissolved in an inert carrier, which is either a water miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, such as, for example, terpenic solvents, including rosin derivatives, aliphatic ketones, such as cyclohexanone, and complex alcohols, such as 2-ethoxyethanol.

Emulsifiers which can be advantageously employed herein can be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters esterified with the polyol or polyoxyalkylene. Cationic emulsifiers include quaternary ammonium compounds and fatty amine salts. Anionic emulsifiers include the oil-soluble salts (e.g., calcium) of alkylaryl sulfonic acids, oil-soluble salts of sulfated polyglycol ethers and appropriate salts of phosphated polyglycol ether.

Representative organic liquids which can be employed in preparing emulsifiable concentrates are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides; and glycol ethers such as the n-butyl ether, ethyl ether or methyl ether of diethylene glycol, and the methyl ether of triethylene glycol and the like. Mixtures of two or more organic liquids may also be employed in the preparation of the emulsifiable concentrate. Surface-active emulsifying agents are typically employed in liquid formulations and in an amount of from 0.1 to 20 percent by weight based on the combined weight of the emulsifying agents.

Aqueous suspensions comprise suspensions of one or more water-insoluble active ingredients dispersed in an aqueous vehicle at a concentration in the range from about 5 to about 50 weight percent, e.g., about 0.1 weight percent, and intermediate ranges, based on the total weight of the aqueous suspension. Suspensions are prepared by finely grinding one or more of the active ingredients, and vigorously mixing the ground material into a vehicle comprised of water and surfactants chosen from the same types discussed above. Other components, such as inorganic salts and synthetic or natural gums, may also be added to increase the density and viscosity of the aqueous vehicle. It is often most effective to grind and mix at the same time by preparing the aqueous mixture and homogenizing it in an implement such as a sand mill, ball mill, or piston-type homogenizer.

Aqueous emulsions comprise emulsions of one or more water-insoluble active ingredients emulsified in an aqueous vehicle at a concentration typically in the range from about 5 to about 50 weight percent, based on the total weight of the aqueous emulsion. If the active ingredient is a solid it must be dissolved in a suitable water-immiscible solvent prior to the preparation of the aqueous emulsion. Emulsions are prepared by emulsifying the liquid active ingredient or water-immiscible solution thereof into an aqueous medium typically with inclusion of surfactants that aid in the formation and stabilization of the emulsion as described above. This is often accomplished with the aid of vigorous mixing provided by high shear mixers or homogenizers.

Granular formulations usually contain from about 0.5 to about 10 weight percent, based on the total weight of the granular formulation of the active ingredient(s), dispersed in an inert carrier which consists entirely or in large part of coarsely divided inert material such as attapulgite, bentonite, diatomite, clay or a similar inexpensive substance. Such formulations are usually prepared by dissolving the active ingredients in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts can be prepared by intimately mixing one or more of the active ingredients in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting and penetration of the active ingredients onto the target site such as a crop or organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent.

Suitable adjuvant surfactants include, but are not limited to ethoxylated nonyl phenols, ethoxylated synthetic or natural alcohols, salts of the esters of sulfosuccinic acids, ethoxylated organosilicones, ethoxylated fatty amines and blends of surfactants with mineral or vegetable oils.

The formulations may optionally include combinations that contain one or more fungicides or pesticidal compounds. Pesticidal compounds may be insecticides, nematicides, miticides, arthropodicides, bactericides or combinations thereof that are compatible or synergistic with the compounds of the presently disclosed subject matter in the medium selected for application, and not antagonistic to the activity of the mixture of Compounds (I)-(IV) or toxic to honey bees.

The compositions of the presently disclosed subject matter herein may have broad ranges of uses to treat a hive or control against pests, diseases, pathogens, or infestations harmful to honey bees. The compositions of the presently disclosed subject matter herein may have broad ranges of uses as a prophylactic treatment of a hive; particularly, wherein the hygienic behavior results in inspection of the hive. In one embodiment, the prophylactic treatment is to reduce the likelihood of colony collapse disorder or severe *Varroa* mite infestation. In another embodiment, the hygienic behavior comprises eating diseased brood or diseased honey bees, removing diseased brood or diseased honey bees from hive cells, removing pests or parasites, uncapping hive cells, or uncapping and recapping hive cells. In a further embodiment, the hygienic behavior results in survival of a honey bee colony. In another embodiment, the hygienic behavior results in suppression of mite reproduction, decreased mite survival, or suppression of a mite infestation.

Generally, when the compositions disclosed herein are used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, anti-foam agents, cleaning agents, rheology agents, stabilizers, dispersing agents and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulphate; sodium dioctyl sulphosuccinate; alkyl phenol ethoxylates; and aliphatic alcohol ethoxylates.

A dispersing agent is a substance which adsorbs onto the surface of particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulphonates. For suspension concentrates, very good adsorption and stabilization are obtained using polyelectrolytes, such as sodium naphthalene sulphonate formaldehyde condensates. Tristyrylphenol ethoxylate phosphate esters are also used. Non-ionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulphonates; sodium naphthalene sulphonate formaldehyde condensates; tristyrylphenol ethoxylate phosphate esters; aliphatic alcohol ethoxylates; alky ethoxylates; EO-PO block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with 12 or more ethylene oxide units and the oil-soluble calcium salt of dodecylbenzene sulphonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilize water-insoluble materials inside the hydrophobic part of the micelle. The types of surfactants usually used for solubilization are non-ionics: sorbitan monooleates; sorbitan monooleate ethoxylates; and methyl oleate esters.

Surfactants are sometimes used, either alone or with other additives such as mineral or vegetable oils as adjuvants to spray-tank mixes to improve the biological performance of the composition on the target. The types of surfactants used for bioenhancement depend generally on the nature and mode of action of the composition. However, they are often non-ionics such as: alky ethoxylates; linear aliphatic alcohol ethoxylates; aliphatic amine ethoxylates.

Organic solvents are used mainly in the formulation of emulsifiable concentrates, ULV formulations, and to a lesser extent granular formulations. Sometimes mixtures of solvents are used. The first main groups of solvents are aliphatic paraffinic oils such as kerosene or refined paraffins. The second main group and the most common comprises the aromatic solvents such as xylene and higher molecular weight fractions of C9 and C10 aromatic solvents. Chlorinated hydrocarbons are useful as cosolvents to prevent crystallization of the compositions when the formulation is emulsified into water. Alcohols are sometimes used as cosolvents to increase solvent power.

Thickeners or gelling agents are used mainly in the formulation of suspension concentrates, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are limited to, montmorillonite, e.g. bentonite; magnesium aluminum silicate; and attapulgite. Water-soluble polysaccharides have been used as thickening-gelling agents for many years. The types of polysaccharides most commonly used are natural extracts of seeds and seaweeds are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol and polyethylene oxide. Another good anti-settling agent is xanthan gum.

Microorganisms cause spoilage of formulated products. Therefore preservation agents are used to eliminate or reduce their effect. Examples of such agents include, but are not limited to: propionic acid and its sodium salt; sorbic acid and its sodium or potassium salts; benzoic acid and its sodium salt; p-hydroxy benzoic acid sodium salt; methyl p-hydroxy benzoate; and 1,2-benzisothiazalin-3-one (BIT).

The presence of surfactants, which lower interfacial tension, often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane while the non-silicone anti-foam agents are water-insoluble oils, such as octanol and nonanol, or silica. In both cases, the function of the anti-foam agent is to displace the surfactant from the air-water interface.

In other embodiments, the presently disclosed subject matter is directed to a method of inducing hygienic behavior in honey bees, the method comprising contacting hive cells with a composition comprising the synergistic mixture of Compound (I), Compound (II), Compound (III), and Compound (IV), or agriculturally acceptable derivatives thereof; and an agriculturally acceptable diluent or carrier, wherein the weight ratio of Compound (I):Compound (II):Compound (III):Compound (IV) is not the weight ratio of Compound (I):Compound (II):Compound (III):Compound (IV) in honey bee extracts. The synergistic mixture is in an effective amount for inducing hygienic behavior in honey bees.

The methods of the presently disclosed subject matter may have broad ranges of uses to treat a hive or control against pests, diseases, pathogens, or infestations harmful to honey bees. In another embodiment, the hygienic behavior results in suppression of mite reproduction, decreased mite survival, or suppression of a mite infestation. In another embodiment, the hygienic behavior results in survival of a honey bee colony. In another embodiment, the hive cells are capped hive cells or uncapped hive cells. In another embodiment, the hive cells are worker-brood cells, drone-brood cells, or queen bee cells. In a further embodiment, the honey bees are of the species *Apis mellifera* or *Apis cerana*.

In one embodiment, the hygienic behavior comprises eating diseased brood or diseased honey bees, removing diseased brood or diseased honey bees from hive cells, removing pests or parasites, uncapping hive cells, or uncapping and recapping hive cells. In another embodiment, the hygienic behavior comprises uncapping a hive cell, removing pests or parasites, and recapping the hive cell. In a further embodiment, the diseased brood or diseased honey bees are infested with a pest or parasite; infected with a pathogen; or damaged. In yet another embodiment the diseased brood are eggs, larvae, or pupae.

In a further embodiment, the pests or parasites are mites, wax moth, small hive beetle, or *Nosema*. In a further embodiment, the mites are mites of the genus *Varroa*; particularly wherein the mites are mites of the species *Varroa destructor* or *Varroa jacobsoni*. In a further embodiment, the mites are mites of the genus *Acarapis*; particularly wherein the mites are mites of the species *Acarapis woodi* (also known as tracheal mite). In another embodiment, the mites are mites of the genus *Tropilaelaps*.

*Varroa destructor* is an obligate, ectoparasitic honey bee mite, arguably the most important threat to honey bee health and apiculture today. [31-32] During their reproductive stage, female foundress mites enter honey brood cells just before capping and bury themselves in the brood food at the base of the cell. After about six hours when the food has been consumed by the bee brood, the mite emerges and establishes a feeding site on the brood, from which it sucks hemolymph. [198] Approximately 70 hours after cell capping the foundress mite begins to lay eggs, the first of which is haploid and develops into a male. Diploid eggs are then laid at approximately 30-hour intervals. These develop into females which mate with the waiting male such that by the end of honey bee development up to four (worker cell) or five (drone cell) fertilized female *Varroa* may emerge with the emerging honey bee to repeat the cycle. [31]*Varroa* act as a physical burden to the bee, reducing body weight and protein levels primarily through the sucking of hemolymph. [44, 199, 200, 201, 202]

While the physical burden of *Varroa* is problematic to honey bee health, it is merely one of many honey bee threats associated with *Varroa*. *Varroa* transmit diseases to honey bees [60, 135, 159, 161] and have been associated with both viral amplification and honey bee disease susceptibility. [51, 60] *Varroa* mites enter honey bee colonies as adults, presumably with returning foragers or drifting workers from other colonies. Inside the nest, the mature, fertilized *Varroa* females enter a brood cell that contains a worker or drone larvae that is about to be closed with a wax cap. After the cell is sealed, the mite emerges from hiding and establishes a feeding site that it will share with its offspring. [35] While the host is undergoing its final molt from the $5^{th}$ larval instar to pupae, the *Varroa* foundress initiates egg-laying, first producing an unfertilized male egg and then subsequently fertilized female eggs every 30 hours. These offspring develop and sib-mate before leaving the cell when the adult honey bee opens the wax capping to emerge. [36, 37]

*Varroa* mites only reproduce on drone brood in *A. cerana* honey bee hosts but are able to utilize worker and drone brood to complete their life cycle in *A. mellifera* honey bees. This difference in host utilization is presumably due to longer development and less hygienic behavior of *A. mellifera* honey bees. [38, 39] *Varroa* directly impairs colony function in *A. mellifera* honey bees, while only curtailing the drone production of *A. cerana* honey bees. Moreover, the persistent worker brood production allows for the build-up of higher *Varroa* population densities in *A. mellifera* colonies. [40]

Varroatosis is caused by the mite parasitizing honey bees, e.g. drones and queen bees, larvae and pupae. Although *Varroa* causes physical and physiological damage when feeding on the honey bee hemolymph [44], its most serious impact on honey bee health is caused by enabling viral diseases. [45] Varroatosis produces great damage in apiculture due to the acute debilitation and high mortality of the members of the honey bee colony. Also, *Varroa* is an effective vector of viruses [30, 31] and possibly other microorgansms. [43] *V. destructor* increases the virulence of viruses [46] and may lead to fatal outbreaks. [47, 48] Specifically, more virulent, strains of viruses are selectively favored. [49] *Varroa* feeding may also activate latent viruses. [31, 50]

Small hive beetle reproduces in a hive and is a damaging pest of beeswax combs, comb honey and bee-collected pollen. The females will lay egg masses in protected crevasses in the hive. The larva feed on the honey and pollen. If the infestation is severe enough the bees will abandon the hive. As the beetles move about the hive they defecate forming a slimy mess that results in the honey fermenting.

Wax moth larvae are very destructive and can quickly destroy stored beeswax combs. They tunnel and chew through combs, particularly combs that have contained brood and pollen. Developing honey bee pupae are exposed when wax moth larvae partly remove the cell caps, a condition known as bald brood. Worker bees chew the remainder of the capping thereby fully exposing the heads of the pupae that continue to develop normally. The lines of bald brood follow the direction of the wax moth's travel. Some honey bee pupae nearing maturity may have deformed legs or wings. One of the causes of this deformity is a result of wax moth excreta affecting the final molt of the pupa before its emergence from the cell.

*Nosema* is a parasitic protozoa, caused by the microsporidian *Nosema apis* or *Nosema ceranae* that resides in the gut of the bee. The parasites damage the hosts by destroying internal organs. Inside the cell of the bee's gut, *Nosema* reproduces by forming spores, which are passed within the bee's waste. Bees will begin to expel waste in the hive and on the outside; and can cause rapid colony decline.

In another embodiment, the pathogen is a bacterium, fungus, or virus. In one embodiment the pathogen is *Ascosphaera apis*; particularly wherein *Ascosphaera apis* causes chalkbrood. In one embodiment, the pathogen is *Aspergillus fumigatus, Aspergillus flavus,* or *Aspergillus niger*; more particularly wherein *Aspergillus fumigatus, Aspergillus flavus*, or *Aspergillus niger* causes stonebrood. In one embodiment, the bacterium is *Paenibacillus larvae* (formerly classified as *Bacillus larvae* and *Paenibacillus larvae* ssp larvae/*pulvifaciens*); more particularly wherein *Paenibacillus larvae* causes American foulbrood. In one embodiment, the bacterium is *Melissococcus plutonius*; more particularly wherein *Melissococcus plutonius* causes European foulbrood. In one embodiment, the virus is of the family of cripaviridae viruses; more particularly, wherein the virus is chronic paralysis virus. In one embodiment, the virus is of the family of dicistroviridae viruses; more particularly, wherein the virus is acute bee paralysis virus, Israeli acute paralysis virus, Kashmir bee virus, or Black queen cell virus. In one embodiment, the virus is Cloudy wing virus, Sacbrood virus, or *Perina nuda*. In another embodiment, the virus is *Morator aetatulas*; more particularly, wherein *Morator aetatulas* causes sacbrood disease. In one embodiment, the virus is of the family Iflaviridae; more particularly, wherein the virus is Deformed wing virus. In one embodiment, the virus is of the family Iridoviridae; more particularly, wherein the virus is invertebrate iridescent virus type 6 (IIV-6). In one embodiment, the virus is of the family Secoviridae; more particularly, wherein the virus is tobacco ringspot virus. In one embodiment, the virus is slow paralysis virus.

Deformed wing virus (DWV), Kashmir bee virus (KBV), sacbrood virus (SBV), acute bee paralysis virus (ABPV), slow paralysis virus (SPV), and Israeli acute paralysis virus (IAPV) have been associated with *Varroa*. [42, 57, 58] Many of these viruses have presumably alternative modes of transmission [59] but the effective horizontal transmission by the *Varroa* vector has profound implications for the viruses that are found in the honey bee hosts. [60]

Chalkbrood is a disease caused by the fungus *Ascosphaera apis* that turns the body of an infected bee larva into fungal cells which eventually produce millions of spores. Infected larvae become overgrown with a white cotton-like mycelium and eventually dry to a hard, white or gray shrunken mass (thus the name Chalkbrood) referred to as a mummy. The fruit-bodies of the fungus develop on the gray-colored mummies, and the spores released from the spore capsules can enter the air of the beehive. The disease is spread through local populations by adult bees emerging from contaminated media. It has been shown that a single adult bee may carry from 50 to 300 million spores on its body surface after having chewed through a single diseased cadaver as it extracts itself from the cell or nesting material. Once the disease becomes established in an area it increases rapidly because of the reuse of contaminated nesting media in successive years. As a result of infection, the colonies fail to grow to a sufficiently large size, their resistance becomes impaired and their honey-producing capacity decreases to a degree depending on the severity of the mycotic infection. Over the past several years various control measures have been developed but none have been completely effective or economically practical. Sterilization of nesting media has been attempted by use of dry chlorine or bleach, convection heat, and microwave exposure. Also, surface sterilization of adult bees consisting of a bee bath in sodium hypochlorite or iodine has been employed. Dusting with general antibiotics and fungicides in such a manner that they are ingested by the adult bee also has met with little success. A related infection, Stonebrood disease (forming stone-hard larvae) is caused by the fungus *Aspergillus flavus* and related species.

American foulbrood is caused by the bacterium *Paenibacullus* larvae, which can remain viable indefinitely on beekeeping equipment. It infects the gut of worker, drone and queen larvae and, while it may not destroy a colony in the first year, if left unchecked may ultimately lead to the death of the colony. The main method of treatment is with the antibiotic oxytetracycline, administered in various forms with a sugar carrier. However, there are many problems associated with administration of oxytetracycline, including problems related to stability, antibiotic contamination of the honey, the possibility of killing open brood on the face of brood combs, and unevenness of dosing.

European Foulbrood disease is caused by the bacterium *Melissococcus pluton*, which is fed to the worker, drone and queen larvae by nurse bees. Diseased colonies fail to increase normally so that no surplus honey, in excess of that needed by the colony to survive, is available for the beekeeper. Oxytetracycline is also used for treating such diseased colonies.

"Damaged" refers to physically damaged, physiologically damaged, health-compromised, and/or immune system-compromised, or dead. The foregoing types of damage can be the result of, without limiting the foregoing, a parasite, pest, pathogen, environmental change-related stresses, malnutrition, or exposure to contaminated food (e.g. for example to pesticide laden pollen), pesticides (e.g. neonicotinoids such as imidacloprid, clothianidin, and thiamethoxam; neonicotinamides; carbamates), insecticides (e.g. organophosphates), fungicides, miticides (e.g. acaricides, such as coumaphos, tau-fluvalinate, flumethrin, and amitraz), or other toxic chemicals.

For example, without limiting the foregoing, honey bees with Varroatosis or dysentery are damaged. For example, without limiting the foregoing, chilled brood or bald brood are damaged. Removal rates that correspond to the level of brood health support the existence of the evolution of a damage-dependent hygienic response. [93, 156] Damage-dependent hygiene is also supported by evidence that immune response affects honey bee cuticular chemicals. [112] Existence of a damage-dependent response to *Varroa* has recently been supported by evidence of mite-virulence dependent hygienic removal. [179]

Miticides used to control *Varroa* infestations, such as fluvalinate and coumaphos, have been found to have lethal and sublethal effects on honey bee queens, workers, and drones. [2, 66, 132, 154, 162, 177, 181] For example, moderate doses of fluvalinate in the hive have been associated with reduced queen weight [68] and reduced drone weight and number of spermatozoa. [203] Even low doses of coumaphos have been associated with increased queen mortality, physical deformities, reduced body and ovary weight, and atypical behavior [68, 133, 177] and moderate coumaphos exposure has been linked to reduction of drone sperm vitality.

Synergistic effects of fluvalinate and coumaphos have been measured, where the toxicity of each chemical is significantly increased in bees previously exposed to the other. [172] The lipophilic nature of both the synthetic pyrethroid fluvalinate and the organophosphate coumaphos leads to high absorption and accumulation of the chemicals in hives, especially in wax, meaning that exposure of bees to these and similar compounds increases with time and number of chemical treatments. A 2007 study of residues in honey bee hives found 46 pesticides in 108 pollen samples, and 20 pesticides in 88 wax samples, with over 55% of pollen and 100% of wax samples containing the most concentrated pesticides: the miticides fluvalinate and coumaphos. [62] Furthermore, immunosuppression caused by chemical exposure makes honey bees more susceptible to parasites like *Varroa*, as well as to the pathogens they vector. [64, 70, 181, 184]

In another embodiment, the hygienic behavior comprises uncapping hive cells of healthy brood or diseased brood; more particularly, wherein the hygienic behavior further comprises recapping the hive cells of healthy brood; particularly, wherein the hygienic behavior further comprises removing diseased brood or pests or parasites; particularly, wherein the hygienic behavior further comprises removing diseased brood or pests or parasites, and recapping the hive cells. The methods of the presently disclosed subject matter herein may have broad ranges of uses as a prophylactic treatment of a hive; particularly, wherein the hygienic behavior results in inspection of the hive. For example, without limiting the foregoing, nurse bees will remove *Varroa*-infested brood but simply recap healthy brood. [96] In one embodiment, the prophylactic treatment is to reduce the likelihood of colony collapse disorder or severe *Varroa* mite infestation.

In another embodiment, contacting hive cells with a composition comprises spraying, dusting, dipping, spotting, or fumigating. In another embodiment, the contacting of the hive cells is on one or more days after the hive cells are capped. In another embodiment, the contacting of the hive cells is on one or more days before the hive cells are capped. The hive cells may be artificial or natural compartments. The hive cells may be part of combs that are natural or artificial (including combs made of wax, resin, plastic, metal, wax-coated plastic). The hive cells are not necessarily part of a hive.

III. EXAMPLES

Example 1: Induced Hygienic Behavior Assays

Compounds:

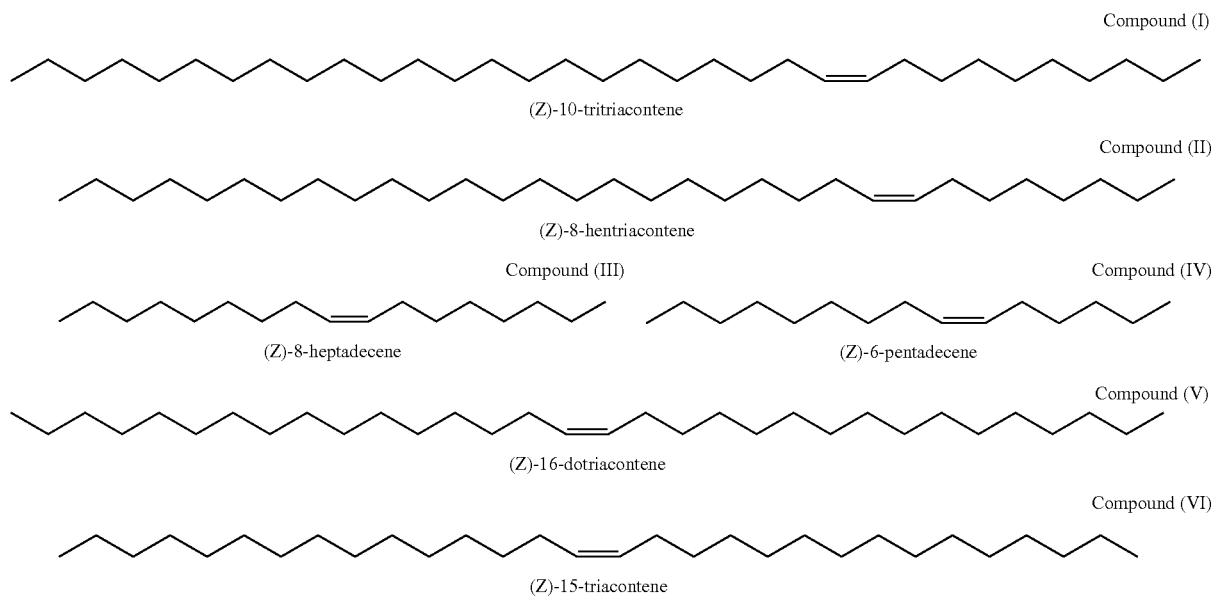

-continued

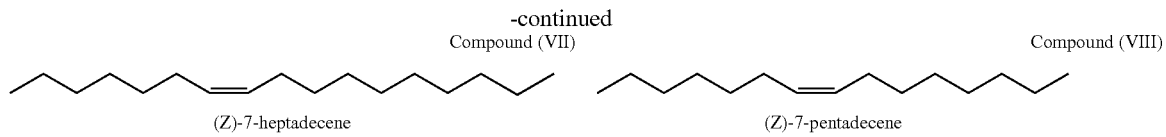

Compound (VII)

(Z)-7-heptadecene

Compound (VIII)

(Z)-7-pentadecene

Treatments Tested:

Treatment (A): A solution comprising 0.50% concentration of each of the following compounds in hexane: Compound (I), Compound (II), Compound (III), and Compound (IV).

Treatment (B): A solution comprising 0.30% concentration of Compound (I) in hexane.

Treatment (C): A solution comprising 0.50% concentration of Compound (I) and Compound (IV) in hexane.

Treatment (D): A solution comprising 0.30% concentration of Compound (IV) in hexane.

Control: A control solution was prepared comprising 0.50% concentration of each of the following compounds in hexane: Compound (V), Compound (VI), Compound (VII), Compound (VIII). Chemicals used for the control assay were similar in structure to those compounds in Treatment (I).

Sample Honey Bee Colonies

Colonies used in the experiments were from five different breeding backgrounds: Minnesota hygienic (HYG), Varroa-sensitive hygienic (VSH), USDA Pollinator Line (POL), unselected Italian (UNS), and Hybrids (HYB). HYB colonies were created by allowing UNS virgin queens to mate in an apiary containing primarily HYG and VSH colonies.

Assay I: Uncapped Cells or Brood Removal a. Application of Treatments 0.5 ml solutions of Treatment (A), Treatment (B), and Treatment (C) were each applied to a 3.8 cm diameter circular region of honey bee pupae wax caps. Assay area was isolated using a piece of steel pipe with a 3.8 cm inner diameter and length of approximately 5 cm. Each solution was applied using a 5 ml glass spray bottle. For each assay, the solution was added to the bottle immediately before application to the wax caps. This was done to minimize leeching of plastic from the spray bottle tubing into the assay solution.

Assay time was 4 hours for Treatment (B) and Treatment (D), and 2 hours for Treatment (A) and (C).

b. Measurement of Uncapped Cells or Removed Brood

Capped cells were quantified at the time of treatment, and frames were returned to the colonies. After two hours, frames were recollected, and capped cells in the assay region were recounted. Assay scores were determined by calculating percent hygiene (including any uncapping or removal) as follows:

% hygienic behavior=(capped cells at $T=2$ hrs/capped cells at $T=0$ hrs)×100

Figure 3:
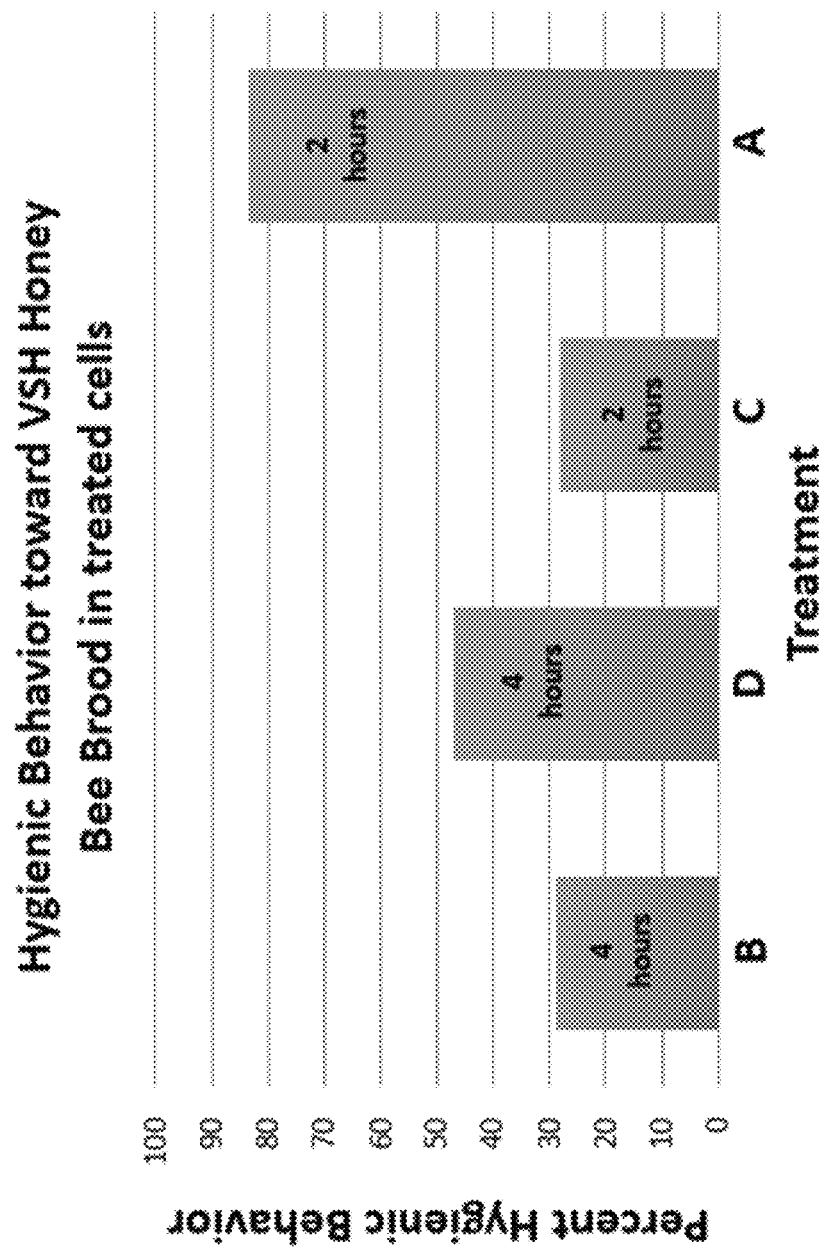
FIG. 3 is a graph representing results from an induced hygienic behavior assay, and in particular, the percent hygienic behavior, as shown by uncapping, removal, or uncapping and removal, resulting from application of Treatment (A) (after 2 hours), Treatment (B) (after 4 hours), Treatment (C) (after 2 hours), and Treatment (D) (after 4 hours) to cell caps. Treatment (A): A solution comprising 0.50% concentration of each of the following compounds in hexane: Compound (I), Compound (II), Compound (III), and Compound (IV). Treatment (B): A solution comprising 0.30% concentration of Compound (I) in hexane. Treatment (C): A solution comprising 0.50% concentration of Compound (I) and Compound (IV) in hexane. Treatment (D): A solution comprising 0.30% concentration of Compound (IV) in hexane.

The calculation "capped cells at T=2 hrs/capped cells at T=0 hrs" provides the number of cells where there was uncapping, removal, or uncapping and removal. The assays for hygienic response for each colony was replicated for each treatment: Treatment A (n=3 replications per colony), Control (n=3 replications per colony). Replicates for each assay were averaged for each colony. For FIG. 1, data for responses for all colonies were averaged. FIG. 3 shows hygienic behavior (uncapping and/or removal) for VSH colonies.

Assay II: Mite Removal Efficiency

Mite removal efficiency was determined for 11 of the 13 colonies by introducing mites collected by sugar shake from a non-experimental colony to recently capped brood cells (>16 hrs since cell capping), and quantifying removal at 8 days post-capping.

Sugar shake methods described in Dietemann et al., Journal of Apicultural Research 52(1): (2013). 300-500 bees are collected and treated with powdered sugar (2018) effectively separates mites from adult bees. Mites and bees were then quantified and the number of mites per 100 bees was calculated.

The colonies not tested either lacked sufficient brood, or had undergone queen supercedure. Mite introductions were performed within 16 hours of cell capping. The location of $5^{th}$ larval instars was recorded on a plastic transparency. Frames were returned to their colonies, and the location of capped cells was recorded approximately 12 hours later. Caps of recently capped cells were opened by cutting one side of the cap with the edge of a sharp razor blade. Mites collected by sugar shake were then introduced to experimental cells using a fined-tipped paintbrush. Control cells were opened just as infested cells, but no mite was introduced. Cells were resealed by pressing the cell cap against the cell wall with the edge of the razor. On day 8 post-capping, frames were recollected and the number of mite-infested and control cells remaining were recorded for each colony.

Figure 2:
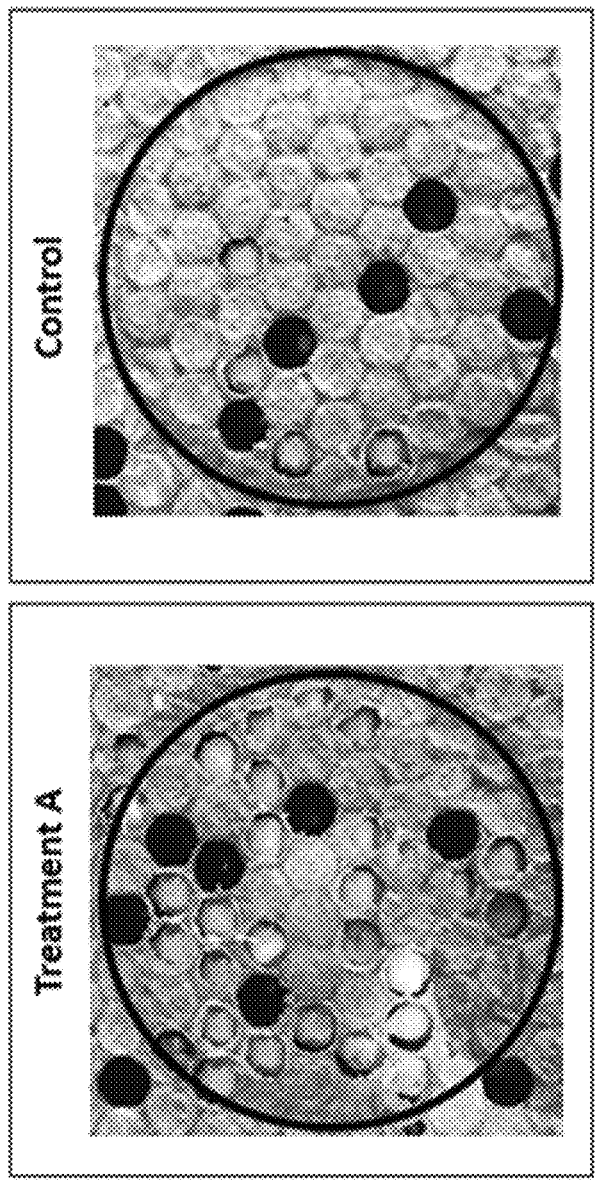
FIG. 2 are exemplary images of the assay honey bee pupae cells after the Treatment A (left) and the Control (right) were applied to wax caps and hygienic behavior quantified.

Results:

FIG. 1 is a graph representing results from an induced hygienic behavior assay, and in particular, the percent hygienic behavior, as shown by 2-hour uncapping, removal, or uncapping and removal, resulting from application of Treatment A or the Control to cell caps. Brood in cells treated with Treatment (A) were significantly more likely than brood treated with the Control to be targeted for and subject to hygienic behavior. Treatment (A) induced significantly more hygienic behavior than the Control. The results show that the hygienic behavior is based on a response to the specific compounds of Treatment (A) as opposed to a response to signals merely perceived as abnormal (Control). It was also surprising that Treatment (A) induced a faster response, i.e. two-hour uncapping/removal. It often takes about 24 hours to achieve a hygienic response in liquid nitrogen free kill brood assays and pin-kill assays. FIG. 2 contains exemplary images of the assay honey bee pupae wax caps after Treatment A (left) and the Control (right) were applied and hygienic behavior assayed. As shown on the left, significantly more caps were removed after application of Treatment (A). FIG. 2 is an example of one replicate of alkene and control assays in the same colony.

FIG. 3 is a graph representing results from an induced hygienic behavior assay, and in particular, the percent hygienic behavior, as shown by uncapping, removal, or uncapping and removal, resulting from application of Treatment (A) (after 2 hours), Treatment (B) (after 4 hours), Treatment (C) (after 2 hours), and Treatment (D) (after 4 hours) to cell caps.

Treatment (A) induced significantly more hygienic behavior than Treatment (B) (after 4 hours), Treatment (C) (after 2 hours), or Treatment (D) (after 4 hours). Based on Chi-square analysis with Bonferroni correction, cells treated with the Treatment A were significantly more likely to be targeted for and subject to hygiene than cells treated with Treatment B ($X^2$=126.44, d.f.=1, p=2.46×10$^{-29}$), Treatment C ($X^2$=138.64, d.f.=1, p=5.29×10$^{-32}$), or Treatment D ($X^2$=60.00, d.f.=1, p=9.48×10$^{-15}$. There was no significant difference in hygienic behavior between cells treated with Treatment C and cells treated with Treatment B ($X^2$=0.08, d.f.=1, p=0.78), however it should be noted that Treatment C achieved the same level of hygienic behavior as Treatment B in half the time. Data from 2 hours post treatment was not collected for cells treated with Treatment B or Treatment D.

|  | Treatment (B) | Treatment (C) | Treatment (A) | Treatment (D) |
|---|---|---|---|---|
| Uncapped and/or Removed | 122 | 143 | 116 | 260 |
| Capped | 298 | 364 | 23 | 295 |

| Comparison | |
|---|---|
| Treatment (B) v. Treatment (C) | $X^2$ = 0.08; d.f. = 1; p = 0.78 |
| Treatment (B) v. Treatment (A) | $X^2$ = 126.44; d.f. = 1; p = 2.46 × 10$^{-29}$ |
| Treatment (C) v. Treatment (A) | $X^2$ = 138.64; d.f. = 1; p = 5.29 × 10$^{-32}$ |
| Treatment (D) v. Treatment (A) | $X^2$ = 60.00; d.f. = 1; p = 9.48 × 10$^{-15}$ |
| Treatment (D) v. Treatment (B) | $X^2$ = 31.79; d.f. = 1; p = 1.72 × 10$^{-8}$ |
| Treatment (D) v. Treatment (C) | $X^2$ = 39.10; d.f. = 1; p = 4.02 × 10$^{-10}$ |

Figure 4:
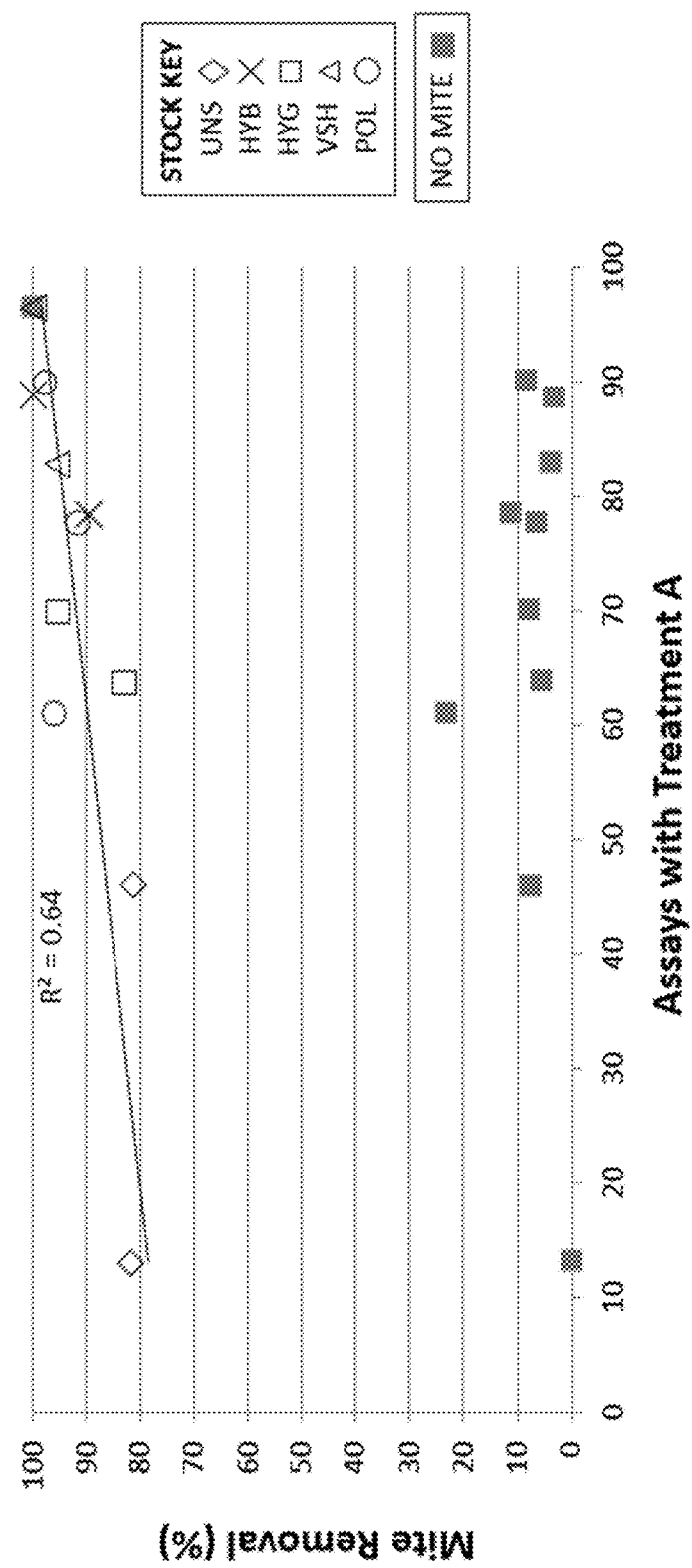
FIG. 4 is a graph representing results from an induced hygienic behavior assay, and in particular, the percent of mite removal resulting from application of Treatment A plotted against the score associated with the level of hygiene in HYG, VSH, POL, UNS, and HYB broods. No mite data relates to control open cells that were opened, but receive no mite.

FIG. 4 is a graph representing results from an induced hygienic behavior assay, and in particular, the percent of mite removal resulting from application of Treatment A plotted against the score associated with the level of hygiene in HYG, VSH, POL, UNS, and HYB broods. The no mite data were control open cells that were opened, but received no mite. There was a significant positive correlation between Treatment (A) and mite removal. In other words, Treatment (A) significantly induced hygienic removal of mites by nurse bees.

Example 2: Unhealthy Brood Odor (UBO) Assay—Comparative Study of Induced Hygienic Behavior Compounds:

Treatments:

Treatment (A): Solutions comprising 0.1%, 0.5%, or 1% of each of the following compounds in hexane: Compound (I), Compound (II), Compound (III), and Compound (IV).

Treatment (B): Solutions comprising 0.1%, 0.5%, or 1% of Compound (I) in hexane.

Treatment (C): Solutions comprising 0.1%, 0.5%, or 1% of Compound (II) in hexane.

Treatment (D): Solutions comprising 0.1%, 0.5%, or 1% of Compound (III) in hexane.

Treatment (E): Solutions comprising 0.1%, 0.5%, or 1% of Compound (IV) in hexane.

Control: A control solution comprising hexane alone.

Solutions comprising compounds (I), (II), (III), or (IV) were tested against mixtures comprising compounds (I)-(IV) in side-by-side assays assessing the extent to which each treatment triggers hygienic uncapping and removal behavior using a dilution series. By dissolving the appropriate amount of each chemical in hexane, 0.1%, 0.5%, or 1% solution of compounds (I), (II), (III), or (IV), and mixture solutions comprising compounds (I)-(IV) (2% total mixture (0.5% each chemical)) were prepared. For each compound and mixture of compounds, the effect of triggering hygienic behavior was tested in side-by-side assays for each of the three dilutions, as well as for a 0% solution, containing hexane alone. For each of these assays, 0.5 ml of one solution was applied to a 3.8 cm diameter circular region of honey bee pupae wax caps. The assay area was isolated using a piece of PVC pipe with a 3.8 cm inner diameter and length of approximately 5 cm. The perimeter of the assay area was marked by gently pressing and twisting the PVC pipe segment into the wax frame. At the time of treatment (T$_0$) the number of capped cells for which >50% of the cell falls inside the assay area was counted and recorded. Each solution was applied to the assay area using a 5 ml glass spray bottle. For each assay, the solution was added to the bottle immediately before application to the wax caps in order to minimize leeching of plastic from the spray bottle tubing into the assay solution. After treatment, experimental frames were be returned to the appropriate colony. At 2 (T$_2$) hours post-treatment, frames were collected and the number of capped cells remaining in each assay area were counted and recorded. An assay score was calculated for each assay at each time point using the equation:

$$\text{Assay Score} = 1 - (\text{capped cells at } T_2/\text{capped cells at } T_0) * 100$$

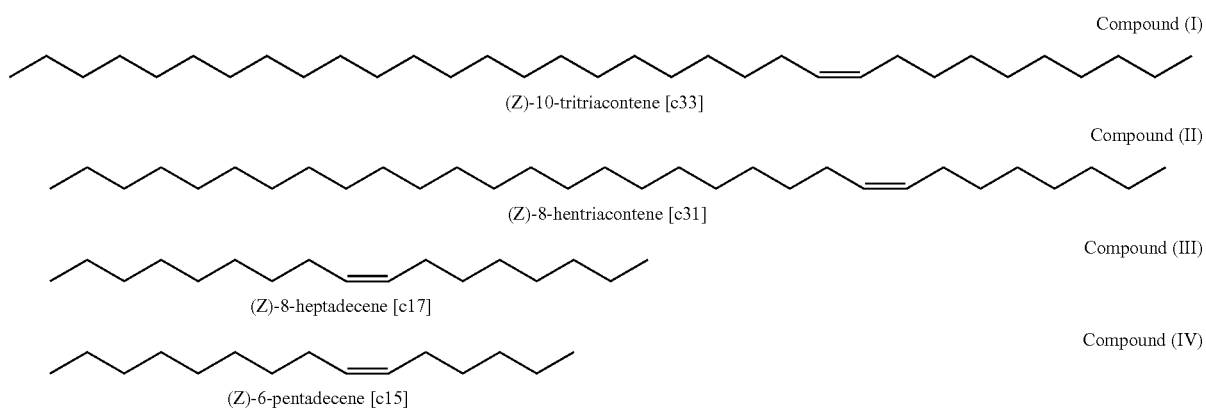

Compound (I)

(Z)-10-tritriacontene [c33]

Compound (II)

(Z)-8-hentriacontene [c31]

Compound (III)

(Z)-8-heptadecene [c17]

Compound (IV)

(Z)-6-pentadecene [c15]

Mite removal efficiency was determined for colonies as described above (Assay III, paragraph 00111-00112). Pearson's correlation coefficients were calculated for all comparisons in FIGS. 4-9. Chi-square analyses were used for analysis of data presented in FIGS. 10a, 10b, and 10c. All statistical analyses were completed using SPSS Statistics, version 26.0.0.0.

Mites for infestation level measurements were collected by sugar shake methods described in Dietemann et al., Journal of Apicultural Research 52(1): (2013). 300-500 bees are collected and treated with either powdered sugar (2018) or ethanol (2019), both of which can effectively separate mites from adult bees. For the FKB assay, sealed brood were frozen using approximately 300 mL liquid nitrogen, and percent removal of freeze-killed brood (FKB) was assessed after 24 hours (see Spivak et al., J. Econ. Entomol. 91(1): 64-70 (1998)).

Results

Figure 5:
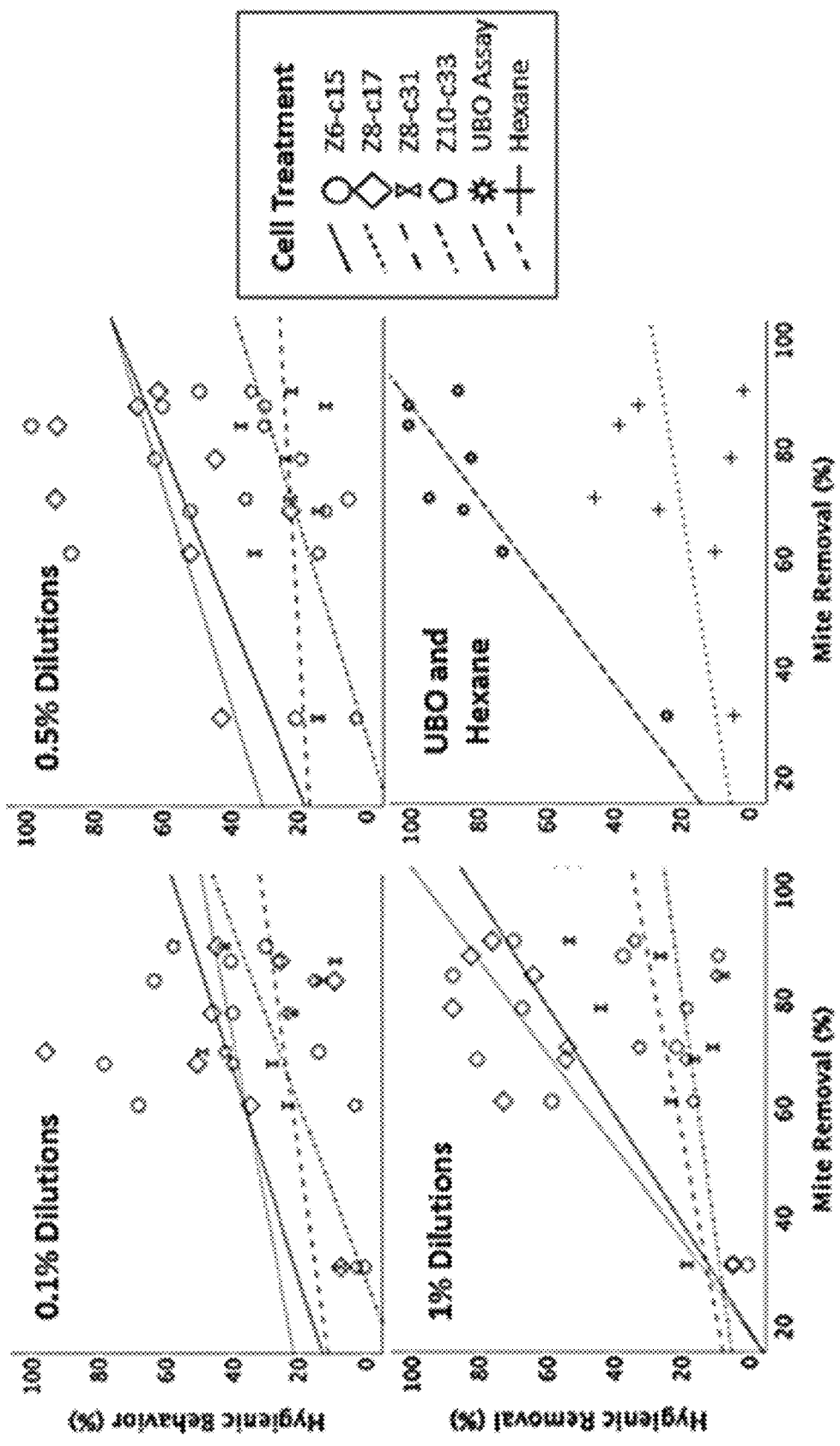
FIG. 5 are graphs representing results from a comparative study of induced hygienic behavior. Each graph represents the percent of mite removal resulting from treatment applications plotted against the percent of hygienic removal, and graphs include data with respect to Treatment B (solution comprising Compound (I):(Z)-10-tritriacontene in hexane, labeled as Z10-c33); Treatment C (solution comprising Compound (II): (Z)-8-hentriacontene in hexane, labeled as Z8-c17); Treatment D (solution comprising Compound (III): (Z)-8-heptadecene in hexane, labeled as Z8-c17); Treatment E (solution comprising Compound (IV): (Z)-6-pentadecene in hexane, labeled as Z6-c15); Treatment A (solution comprising the same concentration of each of Compounds (I), (II), (III, and (IV) in hexane; labeled as UBO Assay); and hexane. The top left graph includes data with respect to 0.1% solutions of Treatments B-E; the top right graph includes data with respect to 0.5% solutions of Treatments B-E; the bottom left graph includes data with respect to 1% solutions of Treatments B-E; and the bottom right graph includes data with respect to Treatment A and hexane only.

Hygienic response to unhealthy brood odors (UBOs) are correlated with colony mite removal. UBO Assay outperforms individual UBOs. FIG. 5 are graphs representing results from a comparative study of induced hygienic behavior. Each graph represents the percent of mite removal resulting from treatment applications plotted against the percent of hygienic removal, and graphs include data with respect to Treatment B (solution comprising Compound (I):(Z)-10-tritriacontene in hexane, labeled as Z10-c33); Treatment C (solution comprising Compound (II): (Z)-8-hentriacontene in hexane, labeled as Z8-c17); Treatment D (solution comprising Compound (III): (Z)-8-heptadecene in hexane, labeled as Z8-c17); Treatment E (solution comprising Compound (IV): (Z)-6-pentadecene in hexane, labeled as Z6-c15); Treatment A (solution comprising the same concentration of each of Compounds (I), (II), (III, and (IV) in hexane; labeled as UBO Assay); and hexane. The top left graph includes data with respect to 0.1% solutions of Treatments B-E; the top right graph includes data with respect to 0.5% solutions of Treatments B-E; the bottom left graph includes data with respect to 1% solutions of Treatments B-E; and the bottom right graph includes data with respect to Treatment A and hexane only.

The UBO Assay was a better predictor of mite removal than individual UBOs (FIG. 5). In the eight colonies in which hygienic response to individual and combined UBOs were tested, there were significant positive correlations between mite removal and hygienic response to the UBO Assay ($r=0.913$, d.f.=6, $p=0.001$). Hygienic response to both Z6-C15 and Z8-C17 was positively correlated with mite removal at the 1.0% concentration ($r=0.636$, d.f.=6, $p=0.045$ and $r=0.859$, d.f.=6, $p=0.003$, respectively). There were significant and suggestive positive correlations between hygienic response to Z10-C33 and mite removal at the 0.5% and 0.1% concentrations ($r=0.821$, d.f.=6, $p=0.006$ and $r=0.606$, d.f.=6, $p=0.056$, respectively). Though all other comparisons showed positive trends, no other correlations were significant.

Figure 6A:
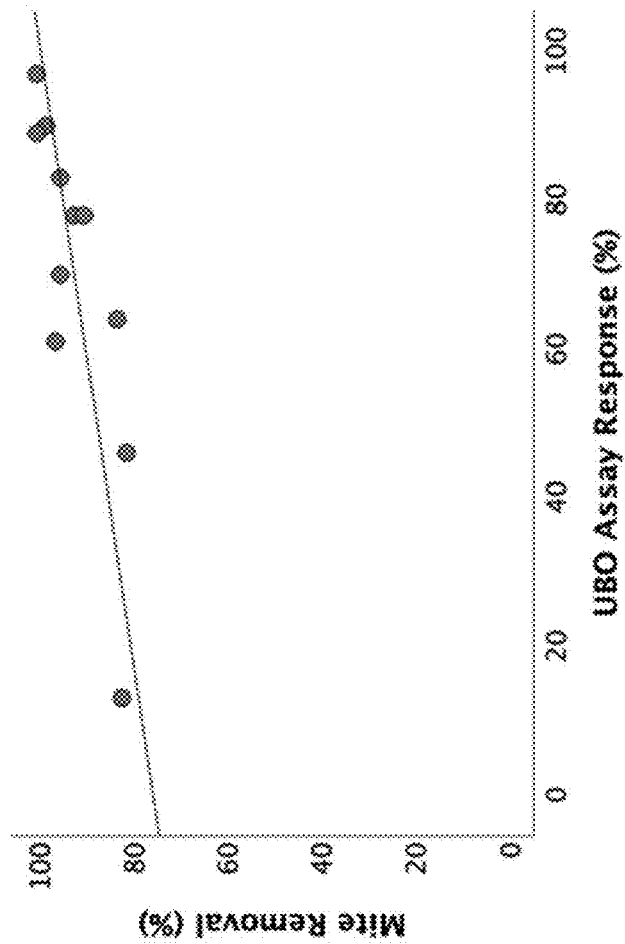
FIG. 6a is a graph representing 2018 study results with percent UBO assay response (or response resulting from 2% solution of Treatment A) plotted against percent mite removal.
Figure 6B:
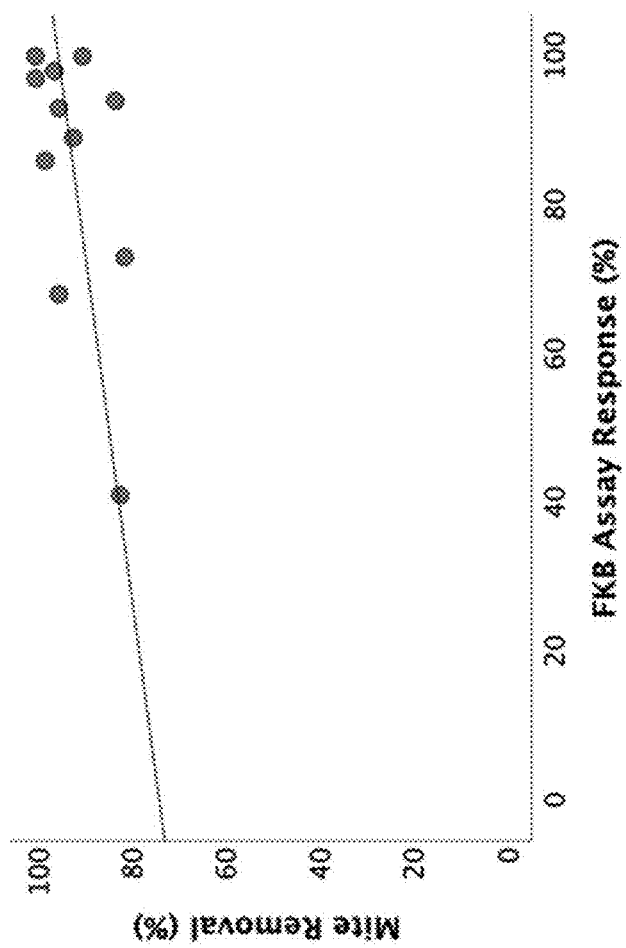
FIG. 6b is a graph representing 2018 study results with percent FKB assay response plotted against percent mite removal.
Figure 6C:
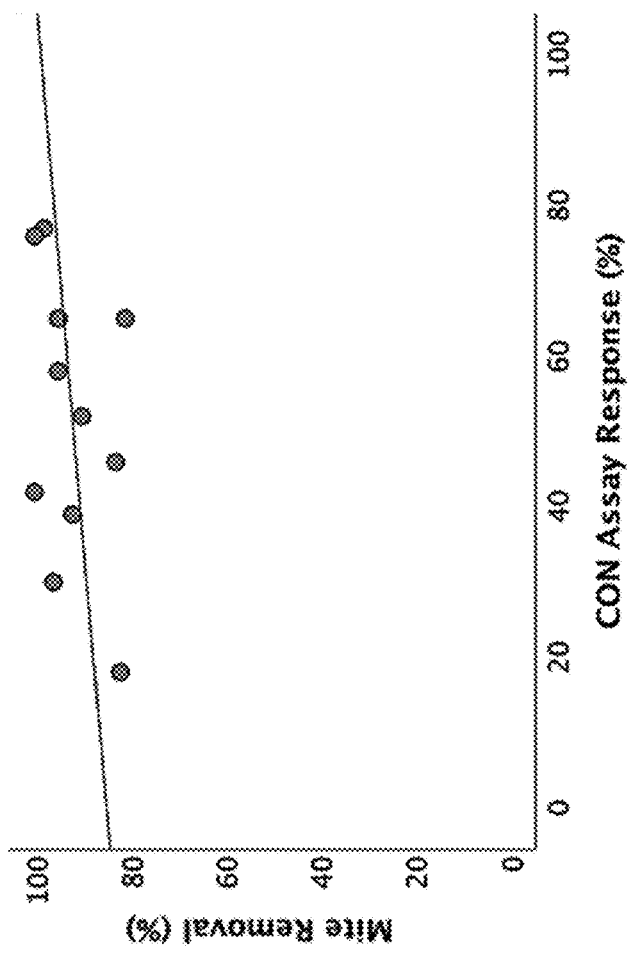
FIG. 6c is a graph representing 2018 study results with percent control assay response (or response resulting from a 2% control solution of structurally-similar chemicals: Compounds (V), (VI), (VII), and (VIII)) plotted against percent mite removal.
Figure 7A:
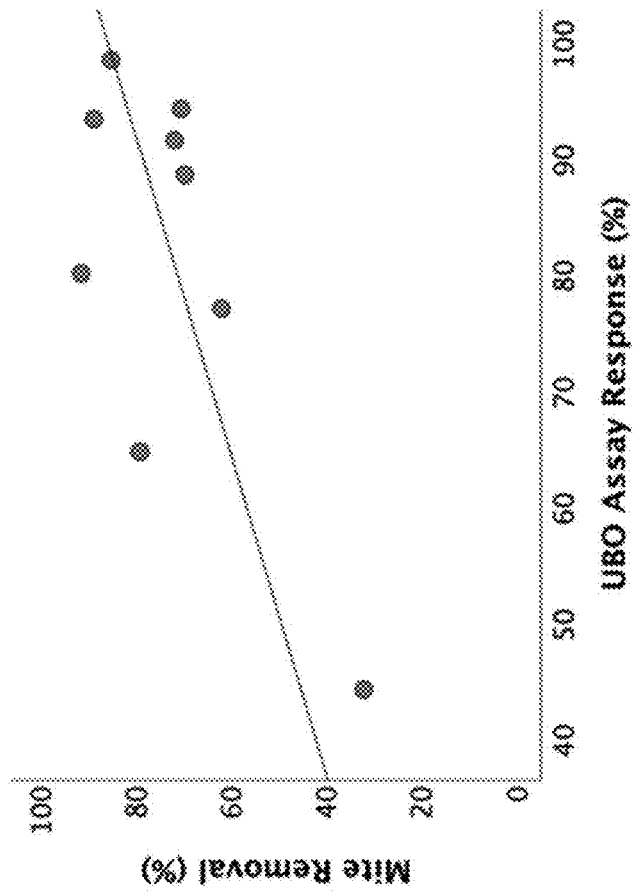
FIG. 7a is a graph representing 2019 study results with percent UBO assay response (or response resulting from 2% solution of Treatment A) plotted against percent mite removal.
Figure 7B:
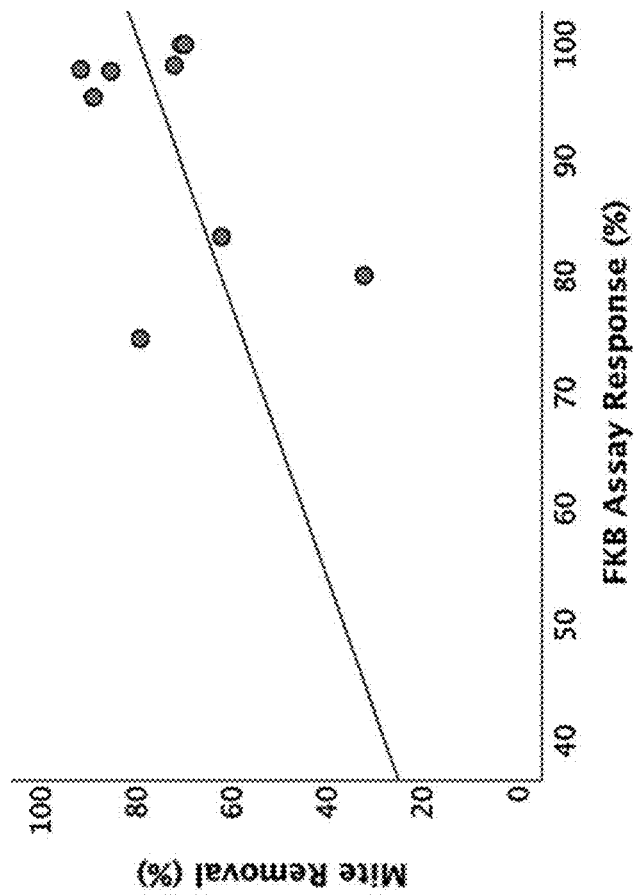
FIG. 7b is a graph representing 2019 study results with percent FKB assay response plotted against percent mite removal.
Figure 7C:
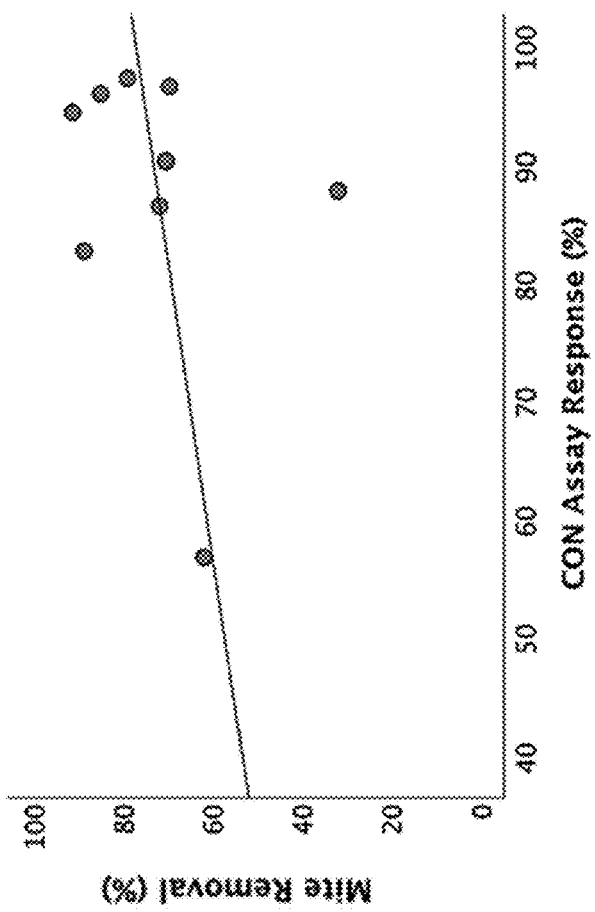
FIG. 7c is a graph representing 2019 study results with percent control assay response (or response resulting from a 2% control solution of structurally-similar chemicals: Compounds (V), (VI), (VII), and (VIII)) plotted against percent mite removal.

The UBO Assay was a better predictor of mite removal than the FKB or CON Assays in 2018 (FIGS. 6a, 6b, 6c) and 2019 (FIGS. 7a, 7b, 7c). FIG. 6a is a graph representing 2018 study results with percent UBO assay response (or response resulting from 2% solution of Treatment A) plotted against percent mite removal. FIG. 6b is a graph representing 2018 study results with percent FKB assay response plotted against percent mite removal. FIG. 6c is a graph representing 2018 study results with percent control assay response (or response resulting from a 2% control solution of structurally-similar chemicals: Compounds (V), (VI), (VII), and (VIII)) plotted against percent mite removal. FIG. 7a is a graph representing 2019 study results with percent UBO assay response (or response resulting from 2% solution of Treatment A) plotted against percent mite removal. FIG. 7b is a graph representing 2019 study results with percent FKB assay response plotted against percent mite removal. FIG. 7c is a graph representing 2019 study results with percent control assay response (or response resulting from a 2% control solution of structurally-similar chemicals: Compounds (V), (VI), (VII), and (VIII)) plotted against percent mite removal.

There were significant positive correlations between hygienic response to the UBO assay and colony mite removal in 2018 ($r=0.80$, d.f.=9, $p=0.001$) and 2019 ($r=0.71$, d.f.=7, $p=0.017$). There was a significant positive correlation between hygienic response to the FKB assay and mite removal in 2018 ($r=0.55$, d.f.=9, $p=0.04$), but not 2019 ($r=0.47$, d.f.=7, $p=0.103$). Hygienic response to the CON chemical assay was not correlated with mite removal in 2018 ($r=0.362$, d.f.=9, $p=0.137$) or 2019 ($r=0.278$, d.f.=7, $p=0.234$).

Figure 8:
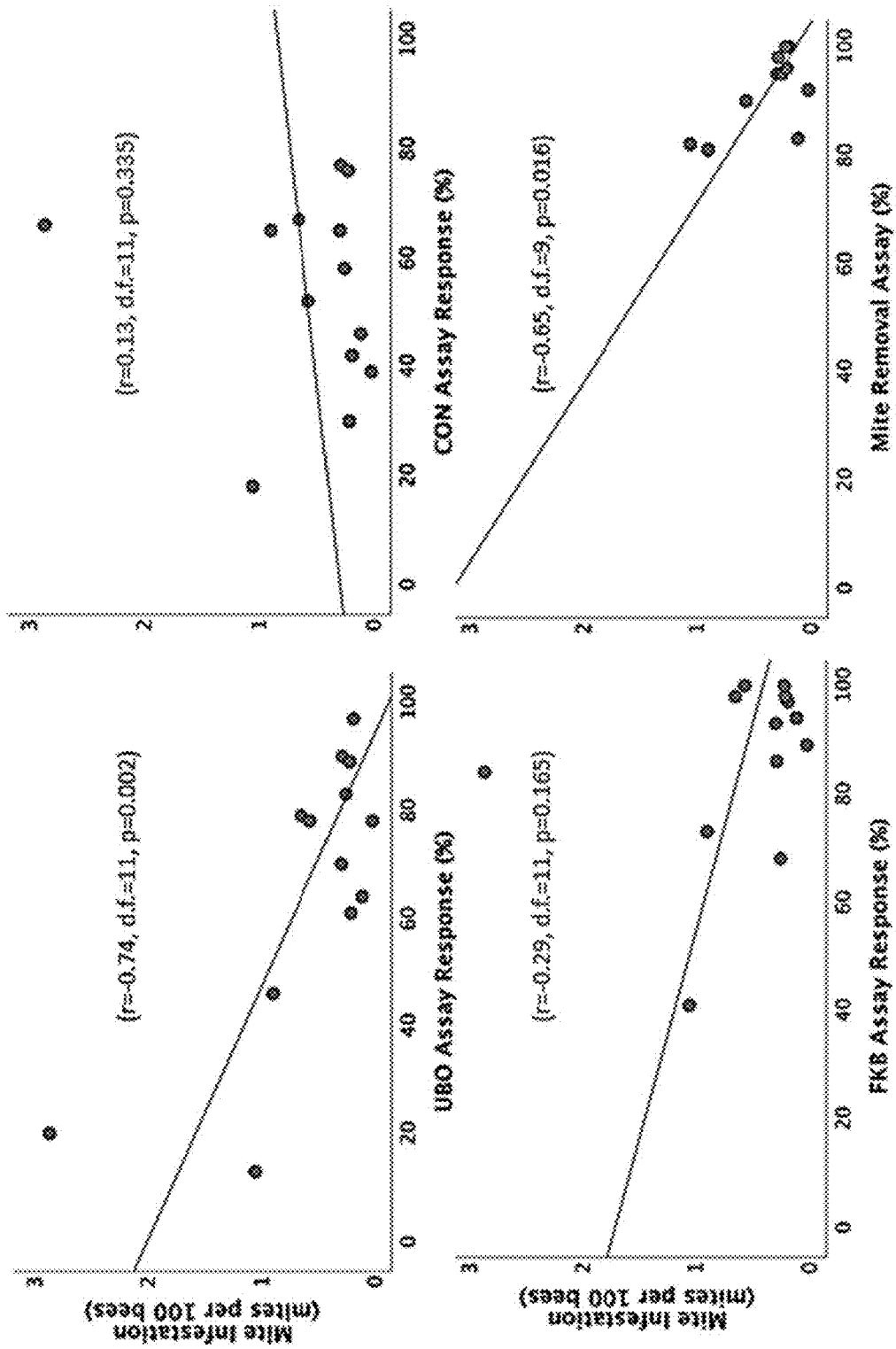
FIG. 8 are graphs representing a 2018 comparative mite infestation study. The top left graph represents percent UBO assay response (or response resulting from 2% solution of Treatment A) plotted against mite infestation (or the number of mites per 100 bees). The top right graph represents percent control assay response (or response resulting from a 2% control solution of structurally-similar chemicals: Compounds (V), (VI), (VII), and (VIII)) plotted against mite infestation (or the number of mites per 100 bees). The bottom left graph represents percent FKB assay response plotted against mite infestation (or the number of mites per 100 bees). The bottom right graph represents percent mite removal assay plotted against mite infestation (or the number of mites per 100 bees).
Figure 9:
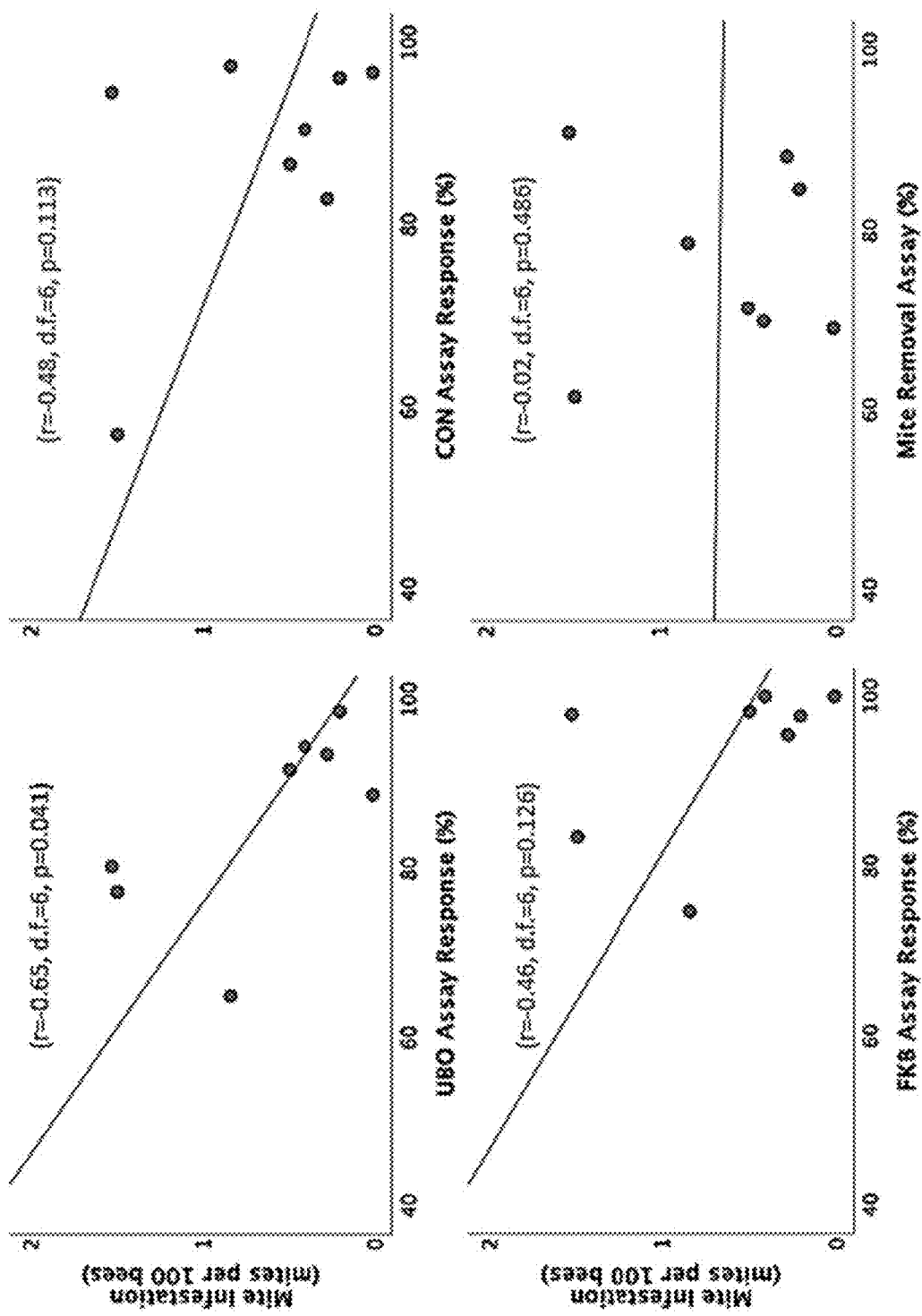
FIG. 9 are graphs representing a 2019 comparative mite infestation study. The top left graph represents percent UBO assay response (or response resulting from 2% solution of Treatment A) plotted against mite infestation (or the number of mites per 100 bees). The top right graph represents percent control assay response (or response resulting from a 2% control solution of structurally-similar chemicals: Compounds (V), (VI), (VII), and (VIII)) plotted against mite infestation (or the number of mites per 100 bees). The bottom left graph represents percent FKB assay response plotted against mite infestation (or the number of mites per 100 bees). The bottom right graph represents percent mite removal assay plotted against mite infestation (or the number of mites per 100 bees).

The UBO Assay was a better predictor of mite infestation than the FKB, CON, or mite removal Assays in 2018 (FIG. 8) and 2019 (FIG. 9). FIG. 8 are graphs representing a 2018 comparative mite infestation study. The top left graph represents percent UBO assay response (or response resulting from 2% solution of Treatment A) plotted against mite infestation (or the number of mites per 100 bees). The top right graph represents percent control assay response (or response resulting from a 2% control solution of structurally-similar chemicals: Compounds (V), (VI), (VII), and (VIII)) plotted against mite infestation (or the number of mites per 100 bees). The bottom left graph represents percent FKB assay response plotted against mite infestation (or the number of mites per 100 bees). The bottom right graph represents percent mite removal assay plotted against mite infestation (or the number of mites per 100 bees).

FIG. 9 are graphs representing a 2019 comparative mite infestation study. The top left graph represents percent UBO assay response (or response resulting from 2% solution of Treatment A) plotted against mite infestation (or the number of mites per 100 bees). The top right graph represents percent control assay response (or response resulting from a 2% control solution of structurally-similar chemicals: Compounds (V), (VI), (VII), and (VIII)) plotted against mite infestation (or the number of mites per 100 bees). The bottom left graph represents percent FKB assay response plotted against mite infestation (or the number of mites per 100 bees). The bottom right graph represents percent mite removal assay plotted against mite infestation (or the number of mites per 100 bees).

There were significant negative correlations between hygienic response to the UBO assay and colony mite infestation in 2018 ($r=-0.74$, d.f.=11, $p=0.002$) and 2019 ($r=0.65$, d.f.=6, $p=0.041$). Hygienic response to the CON chemical assay was not correlated with mite infestation in 2018 ($r=0.126$, d.f.=11, $p=0.335$) or 2019 ($r=-0.482$, d.f.=6, $p=0.113$). Hygienic response to the FKB assay was not correlated with mite infestation in 2018 ($r=0.29$, d.f.=11, $p=0.165$) or 2019 ($r=0.46$, d.f.=6, $p=0.126$). There was a significant negative correlation between mite removal and colony mite infestation in 2018 ($r=-0.654$, d.f.=9, $p=0.014$) but not 2019 ($r=0.015$, d.f.=6, $p=0.486$).

Figure 10A:
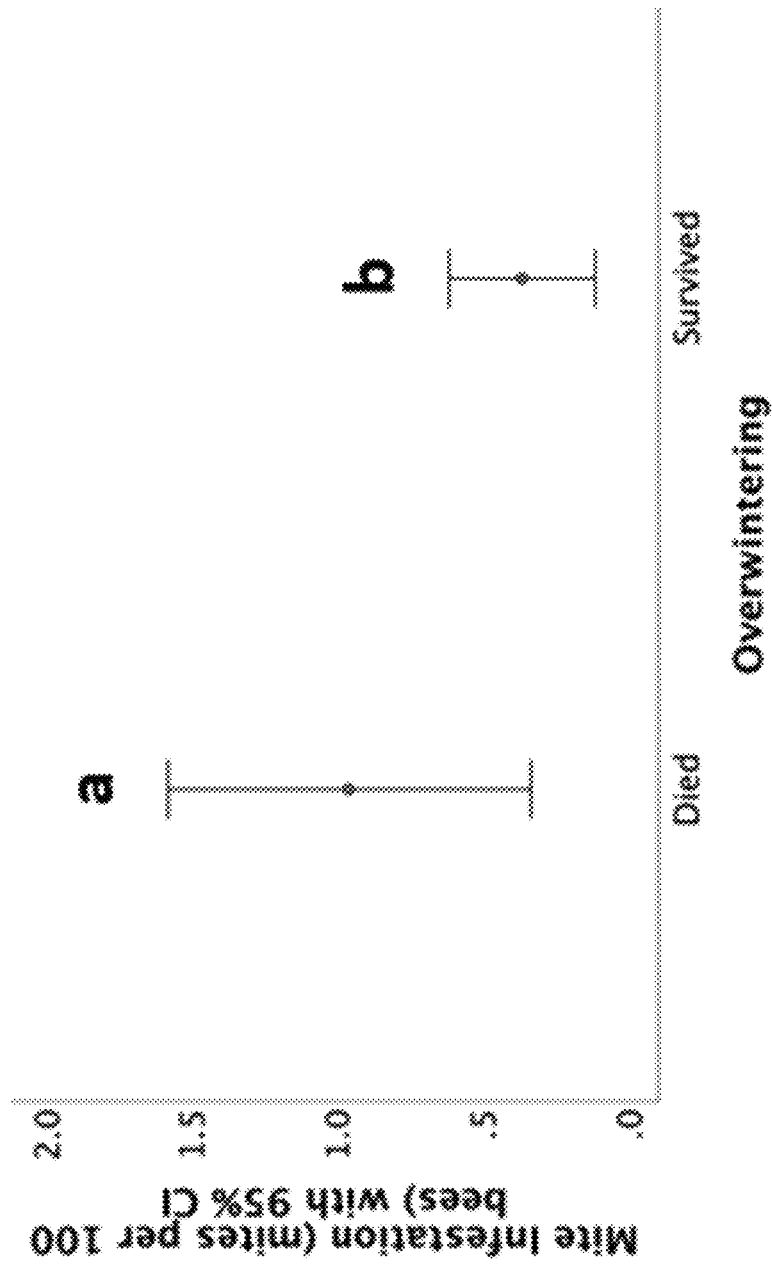
FIG. 10a is a graph representing differences in mite infestation (or the number of mites per 100 bees) with 95% CI, for colonies that experienced either overwintering death or overwintering survival.
Figure 10B:
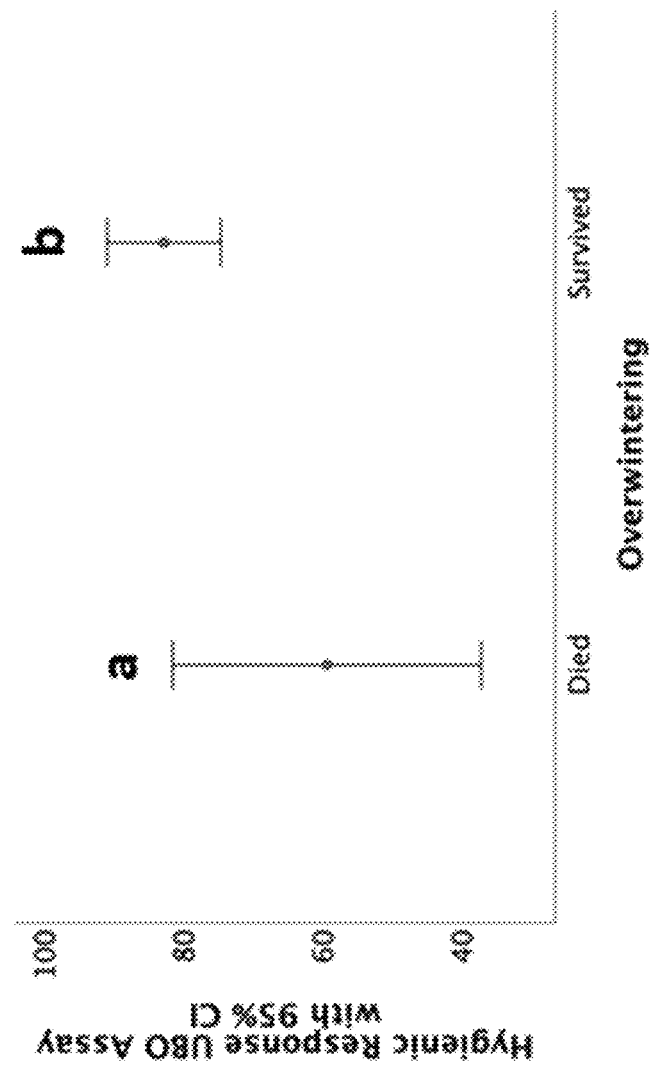
FIG. 10b is a graph representing differences in hygienic response UBO assay with 95% CI, for colonies that experienced either overwintering death or overwintering survival.
Figure 10C:
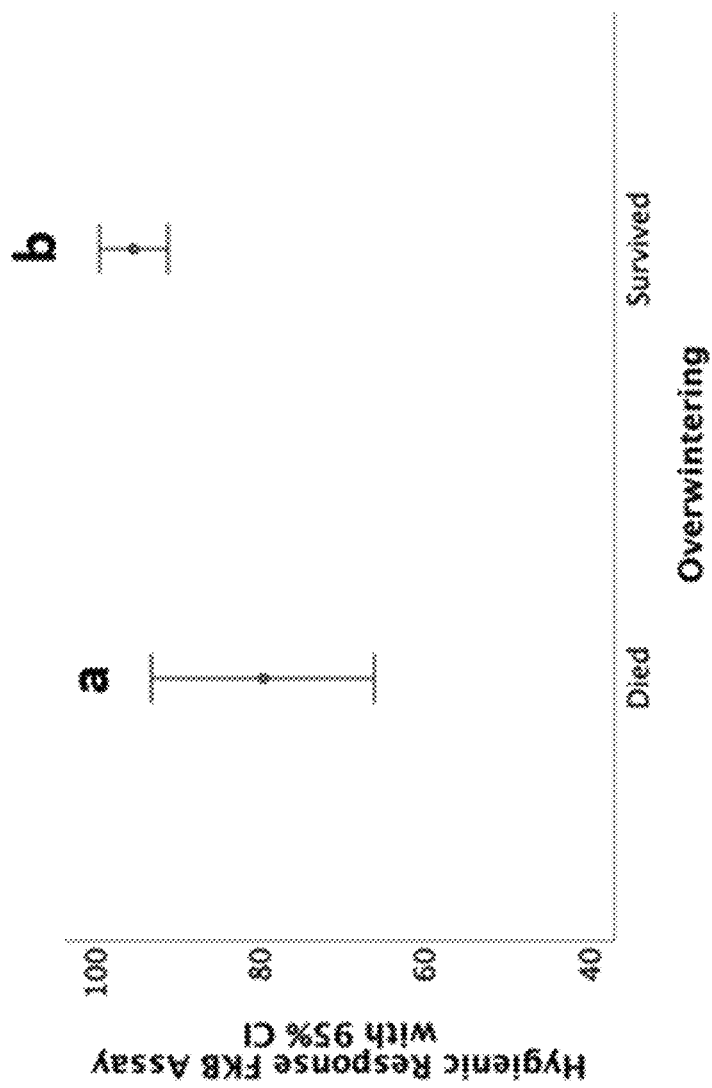
FIG. 10c is a graph representing differences in hygienic response FKB assay with 95% CI, for colonies that experienced either overwintering death or overwintering survival.

The UBO and FKB Assays and Mite Infestation Predict Overwintering Success. FIG. 10a is a graph representing differences in mite infestation (or the number of mites per 100 bees) with 95% CI, for colonies that experienced either overwintering death or overwintering survival. FIG. 10b is a graph representing differences in hygienic response UBO assay with 95% CI, for colonies that experienced either overwintering death or overwintering survival. FIG. 10c is a graph representing differences in hygienic response FKB assay with 95% CI, for colonies that experienced either overwintering death or overwintering survival.

Average mite infestation, UBO Assay response, and FKB Assay response were significantly different for colonies that overwintered successfully compared with those that died (FIG. 10a, 10b, 10c). Colonies that survived had lower mite infestations ($F=5.12$, d.f.$=20$, $p=0.035$), higher UBO Assay response ($F=6.61$, d.f.$=20$, $p=0.018$), and higher FKB Assay response ($F=8.56$, d.f.$=20$, $p=0.008$) than colonies that did not survive. There was no difference in average mite removal ($F=1.42$, d.f.$=18$, $p=0.249$) or average CON Assay response ($F=1.37$, d.f.$=20$, $p=0.255$) between colonies that survived and those that did not survive.

REFERENCES

1. Biesmeijer J C, Roberts S P, Reemer M, Ohlemuller R, Edwards M, Peeters T, Schaffers A P, Potts S G, Kleukers R, Thomas C D et al: Parallel declines in pollinators and insect-pollinated plants in Britain and the Netherlands. *Science* 2006, 313(5785):351-354.
2. Potts S G, Biesmeijer J C, Kremen C, Neumann P, Schweiger O, Kunin W E: Global pollinator declines: trends, impacts and drivers. *Trends Ecol Evol* 2010, 25(6):345-353.
3. Morse R A, Calderone N W: The value of honey bees as pollinators of U.S. crops in 2000. *Bee Culture* 2000, 128:1-15.
4. Committee on the Status of Pollinators in North America NRC: Status of Pollinators in North America. Washington, D.C.: The National Academies Press; 2007.
5. Calderone N W: Insect pollinated crops, insect pollinators and US agriculture: trend analysis of aggregate data for the period 1992-2009. *PLoS One* 2012, 7(5):e37235.
6. Singh R, Levitt A L, Rajotte E G, Holmes E C, Ostiguy N, vanEngelsdorp D, Lipkin W I, dePamphilis C W, Toth A L, Cox-Foster D L: RNA viruses in Hymenopteran pollinators: Evidence of inter-taxa virus transmission via pollen and potential impact on non-Apis Hymenopteran species. *PLoS One* 2010, 5(12):e14357.
7. Winston M L: The Biology of the Honey Bee. Cambridge, Mass.: Harvard University Press; 1987.
8. Boecking O, Spivak M: Behavioral defenses of honey bees against *Varroa jacobsoni* Oud. Apidologie 1999, 30(2-3):141-158.
9. Spivak M, Reuter G S: *Varroa destructor* infestation in untreated honey bee (Hymenoptera: Apidae) colonies selected for hygienic behavior. *J Econ Entomol* 2001, 94(2):326-331.
10. Spivak M, Masterman R, Ross R, Mesce K A: Hygienic behavior in the honey bee (*Apis mellifera* L.) and the modulatory role of octopamine. *J Neurobiol* 2003, 55(3):341-354.
11. Wilson-Rich N, Spivak M, Fefferman N H, Starks P T: Genetic, individual, and group facilitation of disease resistance in insect societies. Annu Rev Entomol 2009, 54:405-423.
12. Oldroyd B P, Fewell J H: Genetic diversity promotes homeostasis in insect colonies. *Trends Ecol Evol* 2007, 22(8):408-413.
13. Whitfield C W, Behura S K, Berlocher S H, Clark A G, Johnston J S, Sheppard W S, Smith D R, Suarez A V, Weaver D, Tsutsui N D: Thrice out of Africa: Ancient and recent expansions of the honey bee, *Apis mellifera*. *Science* 2006, 314(5799):642-645.
14. Ruttner F: Biogeography and Taxonomy of Honeybees. Berlin: Springer; 1988.
15. Goulson D, Nicholls E, Botias C, Rotheray E L: Bee declines driven by combined stress from parasites, pesticides, and lack of flowers. *Science* 2015, 347(6229): DOI: 10.1126/science.1255957.
16. Hawthorne D J, Dively G P: Killing them with kindness? In-hive medications may inhibit xenobiotic efflux transporters and endanger honey bees. *PLoS One* 2011, 6(11):e26796.
17. vanEngelsdorp D, Evans J D, Saegerman C, Mullin C, Haubruge E, Nguyen B K, Frazier M, Frazier J, Cox-Foster D, Chen Y et al: Colony Collapse Disorder: A descriptive study. *PLoS ONE* 2009, 4(8):e6481.
18. vanEngelsdorp D, Meixner M D: A historical review of managed honey bee populations in Europe and the United States and the factors that may affect them. *Journal of Invertebrate Pathology* 2010, 103:S80-S95.
19. McMenamin A J, Genersch E: Honey bee colony losses and associated viruses. Current Opinion in Insect *Science* 2015, 8: doi.org/10.1016/j.cois.2015.1001.1015.
20. van Dooremalen C, Gerritsen L, Cornelissen B, van der Steen J J M, van Langevelde F, Blacquiere T: Winter survival of individual honey bees and honey bee colonies depends on level of *Varroa destructor* infestation. *PLoS One* 2012, 7(4):e36285.
21. Dainat B, Evans J D, Chen Y P, Gauthier L, Neumann P: Predictive markers of honey bee colony collapse. *PLoS One* 2012, 7(2):e32151.
22. Cox-Foster D L, Conlan S, Holmes E C, Palacios G, Evans J D, Moran N A, Quan P L, Briese T, Hornig M, Geiser D M et al: A metagenomic survey of microbes in honey bee colony collapse disorder. *Science* 2007, 318 (5848):283-287.
23. Higes M, Martin-Hernandez R, Botias C, Bailon E G, Gonzalez-Porto A V, Barrios L, del Nozal M J, Bernal J L, Jimenez J J, Palencia P G et al: How natural infection by *Nosema ceranae* causes honeybee colony collapse. *Environ Microbiol* 2008, 10(10):2659-2669.
24. Johnson R M, Evans J D, Robinson G E, Berenbaum M R: Changes in transcript abundance relating to colony collapse disorder in honey bees (*Apis mellifera*). *Proc Natl Acad Sci USA* 2009, 106(35):14790-14795.
25. Cornman R S, Tarpy D R, Chen Y, Jeffreys L, Lopez D, Pettis J S, vanEngelsdorp D, Evans J D: Pathogen webs in collapsing honey bee colonies. *PLoS One* 2012, 7(8):e43562.
26. Genersch E: Honey bee pathology: current threats to honey bees and beekeeping. *Appl Microbiol Biot* 2010, 87(1):87-97.
27. Schmid-Hempel P: Parasites in Social Insects. Princeton, N. J.: Princeton University Press; 1998.
28. Runckel C, Flenniken M L, Engel J C, Ruby J G, Ganem D, Andino R, DeRisi J L: Temporal analysis of the honey bee microbiome reveals four novel viruses and seasonal prevalence of known viruses, *Nosema*, and *Crithidia*. *PLoS One* 2011, 6(6):e20656.
29. Pettis J S, vanEngelsdorp D, Johnson J, Dively G: Pesticide exposure in honey bees results in increased levels of the gut pathogen *Nosema*. Naturwissenschaften 2012, 99(2):153-158.
30. Sammataro D, Gerson U, Needham G: Parasitic mites of honey bees: Life history, implications, and impact. *Annu Rev Entomol* 2000, 45:519-548.

31. Rosenkranz P, Aumeier P, Ziegelmann B: Biology and control of *Varroa destructor*. *J Invertebr Pathol* 2010, 103 Suppl 1:S96-119.
32. Anderson D L, Trueman J W H: *Varroa jacobsoni* (Acari: Varroidae) is more than one species. *Experimental and Applied Acarology* 2000, 24(3):165-189.
33. Kraus B, Page R E: Effect of *Varroa jacobsoni* (Mesostigmata: Varroidae) on feral *Apis mellifera* (Hymenoptera: Apidae) in California. *Environ Entomol* 1995, 24(6): 1473-1480.
34. Seeley T D: Honey bees of the Arnot Forest: a population of feral colonies persisting with *Varroa destructor* in the northeastern United States. Apidologie 2007, 38(1):19-29.
35. Herrmann M, Kanbar G, Engels W: Survival of honey bee (*Apis mellifera*) pupae after trypan blue staining of wounds caused by *Varroa destructor* mites or artificial perforation. Apidologie 2005, 36(1):107-111.
36. Ifantidis M D: Ontogenesis of the mite *Varroa jacobsoni* in worker and drone honeybee brood cells. Journal of Apicultural Research 1983, 22(3):200-206.
37. Martin S J: Ontogeny of the mite *Varroa jacobsoni* (Oud) in worker brood of the honeybee *Apis mellifera* (L) under natural conditions. Experimental & Applied Acarology 1994, 18(2):87-100.
38. Spivak M: Honey bee hygienic behavior and defense against *Varroa jacobsoni*. Apidologie 1996, 27(4):245-260.
39. Peng Y S, Fang Y Z, Xu S Y, Ge L S: The resistance mechanism of the Asian Honey Bee, *Apis cerana* Fabr, to an ectoparasitic mite, *Varroa jacobsoni* Oudemans. Journal of Invertebrate Pathology 1987, 49(1):54-60.
40. Martin S: A population model for the ectoparasitic mite *Varroa jacobsoni* in honey bee (*Apis mellifera*) colonies. Ecol Model 1998, 109(3):267-281.
41. Le Conte Y, Ellis M, Ritter W: *Varroa* mites and honey bee health: can *Varroa* explain part of the colony losses? Apidologie 2010, 41(3):353-363.
42. Boecking O, Genersch E: Varroosis—the ongoing crisis in bee keeping. *J Verbrauch Lebensm* 2008, 3(2):221-228.
43. Benoit J B, Yoder J A, Sammataro D, Zettler L W: Mycoflora and fungal vector capacity of the parasitic mite *Varroa destructor* (Mesostigmata: Varroidae) in honey bee (Hymenoptera: Apidae) colonies. *International Journal of Acarology* 2004, 30(2):103-106.
44. De Jong D, De Jong P, Goncalves L: Weight loss and other damage to developing worker honeybees from infestation with *Varroa jacobsoni*. Journal of Apicultural Research 1982, 21:165-167.
45. Martin S J: The role of *Varroa* and viral pathogens in the collapse of honeybee colonies: a modelling approach. Journal of Applied Ecology 2001, 38(5):1082-1093.
46. Genersch E, Aubert M: Emerging and re-emerging viruses of the honey bee (*Apis mellifera* L.). *Vet Res* 2010, 41(6).
47. Nazzi F, Brown S P, Annoscia D, Del Piccolo F, Di Prisco G, Varricchio P, Della Vedova G, Cattonaro F, Caprio E, Pennacchio F: Synergistic parasite-pathogen interactions mediated by host immunity can drive the collapse of honeybee colonies. *PLoS Pathog* 2012, 8(6): e1002735.
48. Neumann P, Yanez O, Fries I, de Miranda J R: *Varroa* invasion and virus adaptation. *Trends Parasitol* 2012, 28(9):353-354.
49. Ryabov E V, Wood G R, Fannon J M, Moore J D, Bull J C, Chandler D, Mead A, Burroughs N, Evans D J: A virulent strain of deformed wing virus (DWV) of honeybees (*Apis mellifera*) prevails after *Varroa destructor*-mediated, or in vitro, transmission. *PLOS Pathogens* 2014, 10(6):e1004230.
50. Kuster R D, Boncristiani H F, Rueppell O: Immunogene and viral transcript dynamics during parasitic *Varroa destructor* mite infection of developing honey bee (*Apis mellifera*) pupae. JExp Biol 2014, 217(Pt 10):1710-1718.
51. Yang X L, Cox-Foster D L: Impact of an ectoparasite on the immunity and pathology of an invertebrate: Evidence for host immunosuppression and viral amplification. *Proc Natl Acad Sci USA* 2005, 102(21):7470-7475.
52. Gregorc A, Evans J D, Scharf M, Ellis J D: Gene expression in honey bee (*Apis mellifera*) larvae exposed to pesticides and *Varroa* mites (*Varroa destructor*). *J Insect Physiol* 2012, 58(8):1042-1049.
53. Gregory P G, Evans J D, Rinderer T, de Guzman L: Conditional immune-gene suppression of honeybees parasitized by *Varroa* mites. J Insect Sci 2005, 5:7.
54. Boncristiani H F, Evans J D, Chen Y, Pettis J, Murphy C, Lopez D L, Simone-Finstrom M D, Strand M, Tarpy D R, Rueppell O: In-vitro infection of pupae with Israeli Acute Paralysis Virus suggests variation for susceptibility and disturbance of transcriptional homeostasis in honey bees (*Apis mellifera*). *PLoS One* 2013, 8(9):e73429.
55. Azzami K, Ritter W, Tautz J, Beier H: Infection of honey bees with acute bee paralysis virus does not trigger humoral or cellular immune responses. *Arch Virol* 2012, 157(4):689-702.
56. Galbraith D A, Yang X, Nino E L, Yi S, Grozinger C, Schneider D S: Parallel epigenomic and transcriptomic responses to viral infection in honey bees (*Apis mellifera*). *PLOS Pathogens* 2015, 11(3):e1004713.
57. Carreck N L, Ball B V, Martin S J: Honey bee colony collapse and changes in viral prevalence associated with *Varroa destructor*. Journal of Apicultural Research 2010, 49(1):93-94.
58. Di Prisco G, Pennacchio F, Caprio E, Boncristiani H F, Evans J D, Chen Y P: *Varroa destructor* is an effective vector of Israeli acute paralysis virus in the honeybee, *Apis mellifera*. Journal of General Virology 2011, 92:151-155.
59. de Miranda J R, Bailey L, Ball B V, Blanchard P, Budge G E, Chejanovsky N, Chen Y-P, Gauthier L, Genersch E, de Graaf D C: Standard methods for virus research in *Apis mellifera*. Journal of Apicultural Research 2013, 52.
60. Martin S J, Highfield A C, Brettell L, Villalobos E M, Budge G E, Powell M, Nikaido S, Schroeder D C: Global honey bee viral landscape altered by a parasitic mite. *Science* 2012, 336(6086):1304-1306.
61. Locke B, Forsgren E, de Miranda J: Increased tolerance and resistance to virus infections: a possible factor in the survival of *Varroa destructor*. *PLoS One* 2014, 9:e99998.
62. Frazier M, Mullin C, Frazier J, Ashcraft S: What have pesticides got to do with it? American Bee Journal 2008, 148(6):521-524.
63. Tsigouri A D, Menkissoglu S U: Study of tau-fluvalinate persistence in honey. *Pest Manag Sci* 2001, 57:467-471.
64. Mullin C A, Frazier M, Frazier J L, Ashcraft S, Simonds R, vanEngelsdorp D, Pettis J S: High levels of miticides and agrochemicals in North American apiaries: Implications for honey bee health. *PLoS One* 2010, 5(3):e9754.
65. Johnson R M: Honey bee toxicology. Annu Rev Entomol 2015, 60:415-434.
66. Desneux N, Decourtye A, Delpuech J M: The sublethal effects of pesticides on beneficial arthropods. *Annu Rev Entomol* 2007, 52:81-106.

67. Wu J Y, Anelli C M, Sheppard W S: Sub-lethal effects of pesticide residues in brood comb on worker honey bee (*Apis mellifera*) development and longevity. *PLoS One* 2011, 6(2):e14720.
68. Haarmann T, Spivak M, Weaver D, Weaver B, Glenn T: Effects of fluvalinate and coumaphos on queen honey bees (Hymenoptera: Apidae) in two commercial queen rearing operations. *J Econ Entomol* 2002, 95(1):28-35.
69. Forkpah C, Dixon L R, Fahrbach S E, Rueppell O: Xenobiotic effects on intestinal stem cell proliferation in adult honey bee (*Apis mellifera* L) workers. *PLoS One* 2014, 9(3): e91180.
70. Boncristiani H, Underwood R, Schwarz R, Evans J D, Pettis J, vanEngelsdorp D: Direct effect of acaricides on pathogen loads and gene expression levels in honey bees *Apis mellifera*. *J Insect Physiol* 2012, 58(5):613-620.
71. Williamson S M, Wright G A: Exposure to multiple cholinergic pesticides impairs olfactory learning and memory in honeybees. *The Journal of Experimental Biology* 2013, 216(10):1799-1807.
72. Sammataro D, Olafson P, Guerrero F, Finley J: The resistance of *Varroa* mites (Acari: Varroidae) to Acaridies and the presence of esterase. *International Journal of Acarology* 2005, 31(1):67-74.
73. Rademacher E, Harz M: Oxalic acid for the control of varroosis in honey bee colonies—a review. *Apidologie* 2006, 37(1):98-120.
74. Calderone N W: Evaluation of formic acid and a thymol-based blend of natural products for the fall control of *Varroa jacobsoni* (Acari: Varroidae) in colonies of *Apis mellifera* (Hymenoptera: Apidae). *J Econ Entomol* 1999, 92(2):253-260.
75. Dietemann V, Pflugfelder J, Anderson D, Charriere J D, Chejanovsky N, Dainat B, De Miranda J, Delaplane K, Dillier F X, Fuch S et al: *Varroa destructor*: Research avenues towards sustainable control. *Journal of Apicultural Research* 2012, 51(1):125-132.
76. Evans J D: Diverse origins of tetracycline resistance in the honey bee bacterial pathogen *Paenibacillus larvae*. Journal of Invertebrate Pathology 2003, 83(1):46-50.
77. Kochansky J, Knox D A, Feldlaufer M, Pettis J S: Screening alternative antibiotics against oxytetracycline-susceptible and -resistant *Paenibacillus larvae*. Apidologie 2001, 32(3):215-222.
78. Desai S D, Eu Y-J, Whyard S, Currie R W: Reduction in deformed wing virus infection in larval and adult honey bees (*Apis mellifera* L.) by double-stranded RNA ingestion. *Insect Molecular Biology* 2012, 21(4):446-455.
79. Flenniken M L, Andino R: Non-specific dsRNA-mediated antiviral response in the honey bee. *PLoS One* 2013, 8(10):e77263.
80. Hunter W, Ellis J, Hayes J, Westervelt D, Glick E, Williams M, Sela I, Maori E, Pettis J, Cox-Foster D: Large-scale field application of RNAi technology reducing Israeli acute paralysis virus disease in honey bees (*Apis mellifera*, Hymenoptera: Apidae). *PLOS Pathogens* 2010, 6(12):e1001160.
81. Maori E, Paldi N, Shafir S, Kalev H, Tsur E, Glick E, Sela I: IAPV, a bee-affecting virus associated with Colony Collapse Disorder can be silenced by dsRNA ingestion. *Insect Molecular Biology* 2009, 18(1):55-60.
82. Bourgeois A L, Rinderer T E: Genetic characterization of Russian Honey Bee stock selected for improved resistance to *Varroa destructor*. *J Econ Entomol* 2009, 102(3):1233-1238.
83. Spivak M, Reuter G S: Performance of hygienic honey bee colonies in a commercial apiary. Apidologie 1998, 29(3):291-302.
84. Harris J W: Bees with *Varroa* Sensitive Hygiene preferentially remove mite infested pupae aged <=five days post capping. *Journal of Apicultural Research* 2007, 46(3):134-139.
85. Ibrahim A, Spivak M: The relationship between hygienic behavior and suppression of mite reproduction as honey bee (*Apis mellifera*) mechanisms of resistance to *Varroa destructor*. Apidologie 2006, 37(1):31-40.
86. Oxley P R, Spivak M, Oldroyd B P: Six quantitative trait loci influence task thresholds for hygienic behaviour in honeybees (*Apis mellifera*). *Mol Ecol* 2010, 19(7):1452-1461.
87. Tsuruda J M, Harris J W, Bourgeois L, Danka R G, Hunt G J: High-resolution linkage analyses to identify genes that influence *Varroa* Sensitive Hygiene behavior in honey bees. *PLoS One* 2012, 7(11):e48276.
88. De Guzman L I, Rinderer T E, Stelzer J A, Beaman L, Delatte G, Harper C: Hygienic behavior by honey bees from far-eastern Russia. *American Bee Journal* 2002, 142(1):58-60.
89. Locke B, Fries I: Characteristics of honey bee colonies (*Apis mellifera*) in Sweden surviving *Varroa destructor* infestation. Apidologie 2011, 42(4):533-542.
90. Locke B, Conte Y L, Crauser D, Fries I: Host adaptations reduce the reproductive success of *Varroa destructor* in two distinct European honey bee populations. *Ecol Evol* 2012, 2(6):1144-1150.
91. Behrens D, Huang Q, Gessner C, Rosenkranz P, Frey E, Locke B, Moritz R F, Kraus F B: Three QTL in the honey bee *Apis mellifera* L. suppress reproduction of the parasitic mite *Varroa destructor*. *Ecol Evol* 2011, 1(4):451-458.
92. Rinderer T E, Harris J W, Hunt G J, de Guzman L I: Breeding for resistance to *Varroa destructor* in North America. Apidologie 2010, 41(3):409-424.
93. Espinosa-Montano L G, Guzman-Novoa E, Sanchez-Albarran A, Montaldo H H, Correa-Benitez A: Comparative study of three assays to evaluate hygienic behavior in honey bee (*Apis mellifera* L.) colonies. *Veterinaria Mexico* 2008:39-54.
94. Spötter A, Gupta P, Nurnberg G, Reinsch N, Bienefeld K: Development of a 44K SNP assay focussing on the analysis of a *Varroa*-specific defence behaviour in honey bees (*Apis mellifera* carnica). *Molecular Ecology Resources* 2012, 12(2):323-332.
95. Pernal S F, Sewalem A, Melathopoulos A P: Breeding for hygienic behaviour in honeybees (*Apis mellifera*) using free-mated nucleus colonies. Apidologie 2012, 43(4):403-416.
96. Harris J W, Danka R G, Villa J D: Changes in infestation, cell cap condition, and reproductive status of *Varroa destructor* (Mesostigmata: Varroidae) in brood exposed to honey bees with *Varroa* sensitive hygiene. *Ann Entomol Soc Am* 2012, 105(3):512-518.
97. Prisco G D, Zhang X, Pennacchio F, Caprio E, Li J, Evans J D, DeGrandi-Hoffman G, Hamilton M, Chen Y P: Dynamics of persistent and acute deformed wing virus infections in honey bees, *Apis mellifera*. Viruses 2011, 3(12):2425-2441.
98. Le Conte Y, De Vaublanc G, Crauser D, Jeanne F, Rousselle J C, Becard J M: Honey bee colonies that have survived *Varroa destructor*. Apidologie 2007, 38(6):566-572.

99. Basterfield D: *Varroa*—Still a problem in the 21st century? *Bee World* 2011, 88(1):2-4.
100. Spivak M, Downey D L: Field assays for hygienic behavior in honey bees (Hymenoptera: Apidae). *J Econ Entomol* 1998, 91(1):64-70.
101. Spivak M, Gilliam M: Hygienic behaviour of honey bees and its application for control of brood diseases and *Varroa* Part I. Hygienic behaviour and resistance to American foulbrood. *Bee World* 1998, 79(3):124-134, 169-186.
102. Swanson J A, Torto B, Kells S A, Mesce K A, Tumlinson J H, Spivak M: Odorants that induce hygienic behavior in honeybees: identification of volatile compounds in chalkbrood-infected honeybee larvae. *Journal of Chemical Ecology* 2009, 35(9):1108-1116.
103. Schöning C, Gisder S, Geiselhardt S, Kretschmann I, Bienefeld K, Hilker M, Genersch E: Evidence for damage-dependent hygienic behaviour towards *Varroa destructor*-parasitised brood in the western honey bee, *Apis mellifera*. *J Exp Biol* 2012, 215(2):264-271.
104. Baracchi D, Fadda A, Turillazzi S: Evidence for antiseptic behaviour towards sick adult bees in honey bee colonies. *J Insect Physiol* 2012, 58(12):1589-1596.
105. Dietemann V, Nazzi F, Martin S J, Anderson D, Locke B, Delaplane K S, Wauquiez Q, Tannahill C, Frey E, Ziegelmann B et al: Standard methods for *Varroa* research. *Journal of Apicultural Research* 2013, 52(1): 1.09.
106. Dunkelblum E, Tan S H, Silk P J: Double-bond location in monounsaturated fatty acids by dimethyl disulfide derivatization and mass spectrometry: Application to analysis of fatty acids in pheromone glands of four lepidoptera. *Journal of chemical ecology* 1985, 11(3): 265-277.
107. Bello J E, McElfresh J S, Millar J G: Isolation and determination of absolute configurations of insect-produced methyl-branched hydrocarbons. *Proceedings of the National Academy of Sciences* 2015, 112(4):1077-1082.
108. Vincent M, Guglielmetti G, Cassani G, Tonini C: Determination of double-bond position in diunsaturated compounds by mass spectrometry of dimethyl disulfide derivatives. *Analytical Chemistry* 1987, 59(5):694-699.
109. Aboshi T, Shimizu N, Nakajima Y, Honda Y, Kuwahara Y, Amano H, Mori N: Biosynthesis of linoleic acid in Tyrophagus mites (Acarina: Acaridae). *Insect Biochem Molec* 2013, 43(11):991-996.
110. Katzav-Gozansky T, Soroker V, Hefetz A, Cojocaru M, Erdmann D, Francke W: Plasticity of caste-specific Dufour's gland secretion in the honey bee (*Apis mellifera* L.). *Naturwissenschaften* 1997, 84(6):238-241.
111. Nojima S, Apperson C S, Schal C: A simple, convenient, and efficient preparative GC system that uses a short megabore capillary column as a trap. *Journal of chemical ecology* 2008, 34(3):418-428.
112. Richard F J, Aubert A, Grozinger C M: Modulation of social interactions by immune stimulation in honey bee, *Apis mellifera*, workers. *BMC Biol* 2008, 6:50.
113. Rueppell O, Hayworth M K, Ross N P: Altruistic self-removal of health-compromised honey bee workers from their hive. *Journal of Evolutionary Biology* 2010, 23:1538-1546.
114. Torto B, Carroll M J, Duehl A, Fombong A T, Gozansky T K, Nazzi F, Soroker V, Teal P E: Standard methods for chemical ecology research in *Apis mellifera*. *Journal of Apicultural Research* 2013, 52(4).
115. Böröczky K, Wada-Katsumata A, Batchelor D, Zhukovskaya M, Schal C: Insects groom their antennae to enhance olfactory acuity. *Proceedings of the National Academy of Sciences* 2013, 110(9):3615-3620.
116. Eliyahu D, Nojima S, Santangelo R G, Carpenter S, Webster F X, Kiemle D J, Gemeno C, Leal W S, Schal C: Unusual macrocyclic lactone sex pheromone of *Parcoblatta lata*, a primary food source of the endangered red-cockaded woodpecker. *Proceedings of the National Academy of Sciences* 2012, 109(8):E490-E496.
117. Youngsteadt E, Nojima S, Haberlein C, Schulz S, Schal C: Seed odor mediates an obligate ant-plant mutualism in Amazonian rainforests. *Proceedings of the National Academy of Sciences* 2008, 105(12):4571-4575.
118. Nojima S, Schal C, Webster F X, Santangelo R G, Roelofs W L: Identification of the sex pheromone of the German cockroach, *Blattella germanica*. *Science* 2005, 307(5712):1104-1106.
119. Mant J, Brandli C, Vereecken N J, Schulz C M, Francke W, Schiestl F P: Cuticular hydrocarbons as sex pheromone of the bee Colletes cunicularius and the key to its mimicry by the sexually deceptive orchid, *Ophrys exaltata*. *Journal of chemical ecology* 2005, 31(8):1765-1787.
120. Rosenkranz P, Tewarson N, Singh A, Engels W: Differential hygienic behavior towards *Varroa jacobsoni* in capped worker brood of *Apis cerana* depends on alien scent adhering to the mites. *Journal of Apicultural Research* 1993, 32(2):89-93.
121. Furman D, Jojic V, Sharma S, Shen-Orr S S, L. Angel C J, Onengut-Gumuscu S, Kidd B A, Maecker H T, Concannon P, Dekker C L et al: Cytomegalovirus infection enhances the immune response to influenza. *Science Translational Medicine* 2015, 7(281):281ra243.
122. Mondet F, de Miranda J R, Kretzschmar A, Le Conte Y, Mercer A R: On the front line: quantitative virus dynamics in honeybee (*Apis mellifera* L.) colonies along a new expansion front of the parasite *Varroa destructor*. *PLOS Pathogens* 2014, 10(8):e1004323.
123. Podgwaite J D, Mazzone H M: Latency of insect viruses. *Advances in Virus Research* 1986, 31:293-320.
124. Evans J D: Beepath: an ordered quantitative-PCR array for exploring honey bee immunity and disease. *J Invertebr Pathol* 2006, 93(2):135-139.
125. Williams G R, Alaux C, Costa C, Csaki T, Doublet V, Eisenhardt D, Fries I, Kuhn R, McMahon D P, Medrzycki P et al: Standard methods for maintaining adult *Apis mellifera* in cages under in vitro laboratory conditions. *Journal of Apicultural Research* 2013, 52(1).
126. Andersen C L, Jensen J L, Ørntoft T F: Normalization of real-time quantitative reverse transcription-PCR data: a model-based variance estimation approach to identify genes suited for normalization, applied to bladder and colon cancer data sets. *Cancer research* 2004, 64(15): 5245-5250.
127. Severson D, Erickson Jr E, Williamson J, Aiken J: Heat stress induced enhancement of heat shock protein gene activity in the honey bee (*Apis mellifera*). *Experientia* 1990, 46(7):737-739.
128. Otvos L, O I, Rogers M E, Consolvo P J, Condie B A, Lovas S, Bulet P, Blaszczyk-Thurin M: Interaction between heat shock proteins and antimicrobial peptides. *Biochemistry* 2000, 39(46):14150-14159.
129. Coelho J R: Heat transfer and body temperature in honey bee (Hymenoptera: Apidae) drones and workers. *Environ Entomol* 1991, 20(6):1627-1635.
130. Alaux C, Dantec C, Parrinello H, Le Conte Y: Nutrigenomics in honey bees: digital gene expression analysis of pollen's nutritive effects on healthy and *Varroa*-parasitized bees. *BMC Genomics* 2011, 12:496.

131. Wang Y, Kaftanoglu O, Fondrk M K, Page R E: Nurse bee behaviour manipulates worker honeybee (*Apis mellifera* L.) reproductive development. *Anim Behav* 2014, 92:253-261.
132. Johnson R M, Ellis M D, Mullin C A, Frazier M: Pesticides and honey bee toxicity—USA. *Apidologie* 2010, 41(3):312-331.
133. Collins A M, Pettis J S, Wilbanks R, Feldlaufer M F: Performance of honey bee (*Apis mellifera*) queens reared in beeswax cells impregnated with coumaphos. *Journal of Apicultural Research* 2004, 43(3):128-134.
134. Dahlgren L, Johnson R M, Siegfried B D, Ellis M D: Comparative toxicity of acaricides to honey bee (Hymenoptera: Apidae) workers and queens. *J Econ Entomol* 2012, 105(6):1895-1902.
135. Kanbar G, Engels W: Ultrastructure and bacterial infection of wounds in honey bee (*Apis mellifera*) pupae punctured by *Varroa* mites. *Parasitol Res* 2003, 90(5): 349-354.
136. Arrese E L, Soulages J L: Insect fat body: energy, metabolism, and regulation. *Annu Rev Entomol* 2010, 55:207-225.
137. Gillespie and J P, Kanost M R, Trenczek T: Biological mediators of insect immunity. *Annu Rev Entomol* 1997, 42(1):611-643.
138. Trapnell C, Pachter L, Salzberg S L: TopHat: discovering splice junctions with RNA-Seq. *Bioinformatics* 2009, 25(9):1105-1111.
139. Trapnell C, Williams B A, Pertea G, Mortazavi A, Kwan G, van Baren M J, Salzberg S L, Wold B J, Pachter L: Transcript assembly and quantification by RNA-Seq reveals unannotated transcripts and isoform switching during cell differentiation. *Nat Biotechnol* 2010, 28(5): 511-515.
140. Trapnell C, Roberts A, Goff L, Pertea G, Kim D, Kelley D R, Pimentel H, Salzberg S L, Rinn J L, Pachter L: Differential gene and transcript expression analysis of RNA-seq experiments with TopHat and Cufflinks. *Nat Protoc* 2012, 7(3):562-578.
141. Mortazavi A, Williams B A, McCue K, Schaeffer L, Wold B: Mapping and quantifying mammalian transcriptomes by RNA-Seq. *Nat Methods* 2008, 5(7):621-628.
142. Pepke S, Wold B, Mortazavi A: Computation for ChIP-seq and RNA-seq studies. *Nat Methods* 2009, 6(11 Suppl):S22-32.
143. Elsik C G, Worley K C, Bennett A K, Beye M, Camara F, Childers C P, de Graaf D C, Debyser G, Deng J, Devreese B et al: Finding the missing honey bee genes: lessons learned from a genome upgrade. *BMC Genomics* 2014, 15:86.
144. Langmead B, Salzberg S L: Fast gapped-read alignment with Bowtie 2. *Nat Methods* 2012, 9(4):357-359.
145. Anders S, Pyl P T, Huber W: HTSeq-A Python framework to work with high-throughput sequencing data. *Bioinformatics* 2014:btu638.
146. Huang A S, Baltimore D: Defective viral particles and viral disease processes. *Nature* 1970, 226:325-327.
147. Li D, Lott W B, Lowry K, Jones A, Thu H M, Aaskov J: Defective interfering viral particles in acute dengue infections. *PLoS One* 2011, 6(4):e19447.
148. Hurd H: Manipulation of medically important insect vectors by their parasites. *Annu Rev Entomol* 2003, 48(1):141-161.
149. Chen Y P, Siede R: Honey bee viruses. *Adv Virus Res* 2007, 70:33-80.
150. Granberg F, Vicente-Rubiano M, Rubio-Guerri C, Karlsson O E, Kukielka D, Belik S, Sinchez-Vizcaino J M: Metagenomic detection of viral pathogens in spanish honeybees: co-infection by aphid lethal paralysis, Israel acute paralysis and lake sinai viruses. *PLoS One* 2013, 8(2):e57459.
151. Cornman R S, Boncristiani H, Dainat B, Chen Y, Weaver D, Evans J D: Population-genomic variation within RNA viruses of the Western honey bee, *Apis mellifera*, inferred from deep sequencing. *BMC Genomics* 2013, 14(1):154.
152. Garbian Y, Maori E, Kalev H, Shafir S, Sela I: Bidirectional transfer of RNAi between honey bee and *Varroa destructor*: *Varroa* gene silencing reduces *Varroa* population. *PLOS Pathogens* 2012, 8(12):e1003035.
153. Aumeier P., P. Rosenkranz. (2001) Scent or movement of *Varroa destructor* mites does not elicit hygienic behaviour by Africanized and Carniolan honey bees. *Apidologie* 32(3): 253-264.
154. Berry J. (January 2009) Pesticides, Bees and Wax: An Unhealthy, Untidy Mix. Bee Culture: 33-35.
155. Boecking O., K. Bienefeld, W. Drescher. (2000) Heritability of the *Varroa*, a specific hygienic behaviour in honey bees (Hymenoptera: Apidae). Journal of Animal Breeding and Genetics 117(6): 417-424.
156. Boecking O., W. Drescher. (1992) The removal response of *Apis mellifera* L. colonies to brood in wax and plastic cells after artificial and natural infestation with *Varroa jacobsoni* Oud. and to freeze-killed brood. Experimental and Applied Acarology 16(4): 321-329.
157. Bogdanov S. (2006) Contaminants of bee products. Apidologie 37: 1-18.
158. Bostanian N. J., V. Preedy, R. Watson. (2004) Pesticide toxicology: mode of action, residues in fruit crops, and risk assessment. Reviews in Food and Nutrition Toxicity 2: 215-268.
159. Bowen-Walker P., S. Martin, A. Gunn. (1999) The Transmission of Deformed Wing Virus between Honeybees (*Apis mellifera* L.) by the Ectoparasitic Mite *Varroa jacobsoni* Oud. Journal of Invertebrate Pathology 73(1): 101-106.
160. Calderon R. A., N. Fallas, L. G. Zamora, J. W. van Veen, L. A. Sanchez. (2009) Behavior of *Varroa* mites in worker brood cells of Africanized honey bees. Experimental and Applied Acarology 49(4): 329-338.
161. Chen Y., J. S. Pettis, J. D. Evans, M. Kramer, M. F. Feldlaufer. (2004) Transmission of Kashmir bee virus by the ectoparasitic mite *Varroa destructor*. Apidologie 35: 441-448.
162. Claudianos C., H. Ranson, R. Johnson, S. Biswas, M. Schuler, et al. (2006) A deficit of detoxification enzymes: pesticide sensitivity and environmental response in the honeybee. Insect Molecular Biology 15(5): 615-636.
163. Dekeyser M. A., R. G. H. Downer. (1994) Biochemical and physiological targets for miticides. Pesticide Science 40(2): 85-101.
164. Edwards D. (2005) Reregistration Eligibility Decision for Tau-fluvalinate, in: Environmental Protection Agency, S. R. and R. D. (Ed.), pp. 1-76.
165. Frey E., R. Odemer, T. Blum, P. Rosenkranz. (2013) Activation and interruption of the reproduction of *Varroa destructor* is triggered by host signals (*Apis mellifera*). Journal of Invertebrate Pathology.
166. Goode K., Z. Huber, K. A. Mesce, M. Spivak. (2006) Hygienic behavior of the honey bee (*Apis mellifera*) is independent of sucrose responsiveness and foraging ontogeny. Hormones and Behavior 49(3): 391-397.
167. Harbo J. R., J. W. Harris. (2001) Resistance to *Varroa destructor* (Mesostigmata: Varroidae) when mite-resistant 168. Harbo J. R., J. W. Harris. (2009) Responses to *Varroa* by honey bees with different levels of *Varroa* Sensitive Hygiene. Journal of Apicultural Research 48(3): 156-161.
169. Harris, J. W. (2008) Effect of brood type on *Varroa*-sensitive hygiene by worker honey bees (Hymenoptera: Apidae). Annals of the Entomological Society of America 101:1137-1144.
170. Ibrahim A., G. S. Reuter, M. Spivak. (2007) Field trial of honey bee colonies bred for mechanisms of resistance against *Varroa destructor*. Apidologie 38(1): 67-76.
171. Imdorf A. C., J D; Kilchemann, V; Bogdanov, S; Fluri, P. (2003) Alternative strategy in central Europe for the control of *Varroa destructor* in honey bee colonies. Apiacta 38: 258-278.
172. Johnson R. M., H. S. Pollock, M. R. Berenbaum. (2009) Synergistic interactions between in-hive miticides in *Apis mellifera*. Journal of Economic Entomology 102(2): 474-479.
173. Kanga L. H. B., A. B. Somorin. (2012) Susceptibility of the small hive beetle, *Aethina tumida* (Coleoptera: Nitidulidae), to insecticides and insect growth regulators. Apidologie 43: 95-102.
174. Martel A. C., S. Zeggane, C. Aurieres, P. Drajnudel, J. P. Faucon, et al. (2007) Acaricide residues in honey and wax after treatment of honey bee colonies with Apivar or Asuntol 50. Apidologie 38(6): 534-544.
175. Masterman R., R. Ross, K. Mesce, M. Spivak. (2001) Olfactory and behavioral response thresholds to odors of diseased brood differ between hygienic and non-hygienic honey bees (*Apis mellifera* L.). Journal of Comparative Physiology A: Neuroethology, Sensory, Neural, and Behavioral Physiology 187(6): 441-452.
176. Parker R., M. M. Guarna, A. Melathopoulos, K. M. Moon, R. White, et al. (2012) Correlation of proteome-wide changes with social immunity behaviors provides insight into resistance to the parasitic mite, *Varroa destructor*, in the honey bee (*Apis mellifera*). Genome Biology 13(9): R81.
177. Pettis J. S., A. M. Collins, R. Wilbanks, M. F. Feldlaufer. (2004) Effects of coumaphos on queen rearing in the honey bee, *Apis mellifera*. Apidologie 35(6): 605-610.
178. Sammataro D., P. Untalan, F. Guerrero, J. Finley. (2005) The resistance of *Varroa* mites (Acari: Varroidae) to acaricides and the presence of esterase. International Journal of Acarology 31(1): 67-74.
179. Schoning C., S. Gisder, S. Geiselhardt, I. Kretschmann, K. Bienefeld, et al. (2012) Evidence for damage-dependent hygienic behaviour towards *Varroa destructor*-parasitised brood in the western honey bee, *Apis mellifera*. The Journal of Experimental Biology 215(2): 264-271.
180. Shelton D. R., C. J. Somich. (1988) Isolation and characterization of coumaphos-metabolizing bacteria from cattle dip. Applied and Environmental Microbiology 54(10): 2566-2571.
181. Spivak M., E. Mader, M. Vaughan, N. H. Euliss Jr. (2011) The Plight of the Bees. Environ. Sci. Technol 45(1): 34-38.
182. Spivak M., G. S. Reuter. (2001) Resistance to American foulbrood disease by honey bee colonies *Apis mellifera* bred for hygienic behavior. Apidologie 32(6): 555-565.
183. Spotter A., P. Gupta, G. Nurnberg, N. Reinsch, K. Bienefeld. (2012) Development of a 44K SNP assay focusing on the analysis of a *Varroa*-specific defence behaviour in honey bees (*Apis mellifera* carnica). Molecular Ecology Resources 12: 323-332.
184. vanEngelsdorp D., J. Hayes, R. M. Underwood, J. Pettis. (2008) A survey of honey bee colony losses in the US, fall 2007 to spring 2008. PLoS One 3(12): e4071.
185. Wallner K. (1999) Varroacides and their residues in bee products. Apidologie 30: 235-248.
186. Dade H A (1994, 2009) Anatomy and dissection of the honey bee (revised edition). International Bee Research Association, Cardiff, UK.
187. Fakhimzadeh K (2001) Effectiveness of confectioner sugar dusting to knock down *Varroa destructor* from adult honey bees in laboratory trials. Apidologie 32: 139-148.
188. Sokal R R & Rohlf F J (1995) The principles and practice of statistics in biological research. WH Freeman and Co., New York.
189. Genersch E., W. von der Ohe, H. Kaatz, A. Schroeder, C. Otten, et al. (2010) The German bee monitoring project: a long term study to understand periodically high winter losses of honey bee colonies. Apidologie 41(3): 332-352.
190. Berenbaum M., P. Bernhardt, S. Buchmann, N. Calderone, P. Goldstein, et al. (2007) Status of pollinators in North America, The National Academies Press, Washington, D.C.
191. Aizen M. A., L. D. Harder. (2009) The global stock of domesticated honey bees is growing slower than agricultural demand for pollination. Current biology 19(11): 915-918.
192. vanEngelsdorp D., D. Caron, J. Hayes, R. Underwood, M. Henson, et al. (2012) A national survey of managed honey bee 2010-11 winter colony losses in the USA: results from the Bee Informed Partnership. Journal of Apicultural Research 51(1): 115-124.
193. Spleen A. M., E. J. Lengerich, K. Rennich, D. Caron, R. Rose, et al. (2013) A national survey of managed honey bee 2011-12 winter colony losses in the United States: results from the Bee Informed Partnership. Journal of Apicultural Research 52(2): 44-53.
194. Steinhauer N. A., K. Rennich, M. E. Wilson, D. M. Caron, E. J. Lengerich, et al. (2014) A national survey of managed honey bee 2012-2013 annual colony losses in the USA: results from the Bee Informed Partnership. Journal of Apicultural Research 53(1): 1-18.
195. Lee K. V., N. Steinhauer, K. Rennich, M. E. Wilson, D. R. Tarpy, et al. (2015) A national survey of managed honey bee 2013-2014 annual colony losses in the USA. Apidologie 46(3): 292-305.
196. Kirrane M. J., L. I. De Guzman, T. E. Rinderer, A. M. Frake, J. Wagnitz, et al. (2011) Asynchronous development of Honey Bee host and *Varroa destructor* (Mesostigmata: Varroidae) influences reproductive potential of mites. Journal of economic entomology 104(4): 1146-1152.
197. Carreck N. L. (2011) *Varroa*. Still a problem in the 21st century? International Bee Research Association.
198. Ifantidis M. D. (1988) Some aspects of the process of *Varroa jacobsoni* mite entrance into honey bee (*Apis mellifera*) brood cells. Apidologie 19(4): 387-396.
199. Schatton-Gadelmayer K., W. Engels. (1988) Blood proteins and body weight of newly-emerged worker honeybees with different levels of parasitization of brood mites. Entomolgia Generalis 14: 93-101.
200. D'Aubeterre J. P., D. D. Myrold, L. A. Royce, P. A. Rossignol. (1999) A scientific note of an application of isotope ratio mass spectrometry to feeding by the mite,

*Varroa jacobsoni* Oudemans, on the honeybee, *Apis mellifera* L. Apidologie 30(4): 351-352.
201. Amdam G. V., K. Hartfelder, K. Norberg, A. Hagen, S. W. Omholt. (2004) Altered physiology in worker honey bees (Hymenoptera: Apidae) infested with the mite *Varroa destructor* (Acari: Varroidae): a factor in colony loss during overwintering? Journal of Economic Entomology 97(3): 741-747.
202. Garedew A., E. Schmolz, I. Lamprecht. (2004) The energy and nutritional demand of the parasitic life of the mite *Varroa destructor*. Apidologie 35: 419-430.
203. Sylvester H. A., R. P. Watts, L. I. Guzman, J. A. Stelzer, T. E. Rinderer. (1999) *Varroa* in the mating yard. I I. The effects of *Varroa* and fluvalinate on drone mating competitiveness. American Bee Journal 139.
204. Burley L. M., R. D. Fell, R. G. Saacke. (2008) Survival of honey bee (Hymenoptera: Apidae) spermatozoa incubated at room temperature from drones exposed to miticides. Journal of economic entomology 101(4): 1081-1087.
205. Millar J G: Chemical synthesis of insect cuticular hydrocarbons. Insect hydrocarbons: biology, biochemistry, and chemical ecology. Cambridge University Press, Cambridge 2010:163-186.
206. Carlson D, Mackley J: Polyunsaturated hydrocarbons in the stable fly. Journal of chemical ecology 1985, 11:1485-1496.
207. Ginzel M D, Moreira J A, Ray A M, Millar J G, Hanks L M: (Z)-9-Nonacosene major component of the contact sex pheromone of the beetle Megacyllene caryae. Journal of chemical ecology 2006, 32:435-451.
208. Kuster R D, Boncristiani H F, Rueppell O: Immunogene and viral transcript dynamics during parasitic *Varroa destructor* mite infection of developing honey bee (*Apis mellifera*) pupae. Journal of Experimental Biology 2014, 217:1710-1718.
209. Delaplane K S, van der Steen J, Guzman-Novoa E: Standard methods for estimating strength parameters of *Apis mellifera* colonies. *Journal of Apicultural Research* 2013, 52:1-12.
210. De Smet L, Ravoet J, de Miranda J R, Wenseleers T, Mueller M Y, Moritz R F, De Graaf D C: BeeDoctor, a versatile MLPA-based diagnostic tool for screening bee viruses. *PLoS One* 2012, 7:e47953.
211. Mondet, F. et al. Specific Cues Associated With Honey Bee Social Defence against *Varroa destructor* Infested Brood. *Sci. Rep.* 6, 25444 (2016).
212. Le Conte, Y., Arnold, G., Trouiller, J., Masson, C. & Chappe, B. Identification of a brood pheromone in honeybees. Naturwissenschaften 77, 334-336 (1990).
213. Slessor, K., Winston, M. & Conte, Y. Pheromone communication in the honeybee (*Apis mellifera* L.). *J. Chem. Ecol.* 31, 2731-2745 (2005).
214. Francesco Nazzi, Giorgio Della Vedova, Mauro D'Agaro. A semiochemical from brood cells infested by *Varroa destructor* triggers hygienic behaviour in *Apis mellifera. Apidologie*, Springer Verlag, 2004, 35 (1), pp. 65-70.
215. Sonnet, P. E., Uebel, E. C., Lusby, W. R., Schwarz, M., and Miller, R. W. Sex pheromone of the stable fly. Identification, synthesis and evaluation of alkenes from female stable flies. *J. Chem. Ecol.*, 5, 353-351. 1979.
216. Kimura, T., Carlson, D. A., and Mori, K. 2001. Pheromone synthesis. Part 211. Synthesis of all of the stereoisomers of 13,17-dimethyl-1-tritriacontene and 13,17-dimethyl-1-pentatriacontene: the contact sex pheromone components of the female tsetse fly, *Glossina austeni*. European J. Org. Chem. 3385-3390.

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Although the foregoing subject matter has been described in some detail by way of illustration and example for purposes of clarity of understanding, it will be understood by those skilled in the art that certain changes and modifications can be practiced within the scope of the appended claims.

What is claimed:

1. A synergistic mixture for inducing hygienic behavior in honey bees comprising: from about 0.1% to about 1% by weight of Compound (I) having the structure:

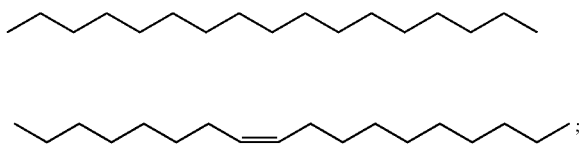

from about 0.1% to about 1% by weight of Compound (II) having the structure:

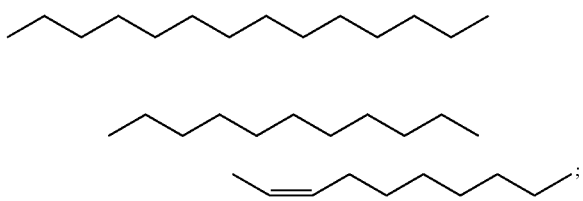

from about 0.1% to about 1% by weight of Compound (III) having the structure:

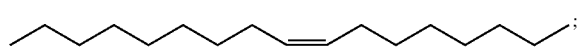

and from about 0.1% to about 1% by weight of Compound (IV) having the structure:

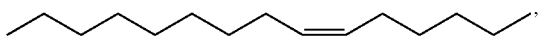

or agriculturally acceptable derivatives thereof.

2. A synergistic mixture for inducing hygienic behavior in honey bees consisting essentially of:

Compound (I) having the structure:

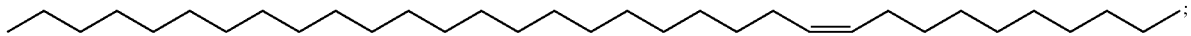 [SMILES: CCCCCCCCC/C=C\CCCCCCCCCCCCCCCCCCCCCC]

Compound (II) having the structure:

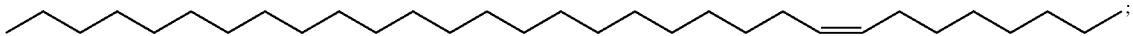 [SMILES: CCCCCCC/C=C\CCCCCCCCCCCCCCCCCCCCCC]

Compound (III) having the structure:

and Compound (IV) having the structure:

or agriculturally acceptable, derivatives thereof.

3. A synergistic mixture for inducing hygienic behavior in honey bees consisting of: Compound (I) having the structure:

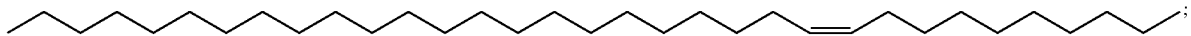 [SMILES: CCCCCCCCC/C=C\CCCCCCCCCCCCCCCCCCCCCC]

Compound (II) having the structure:

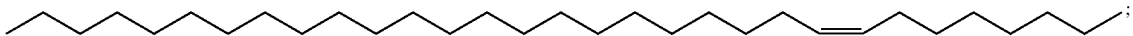

Compound (III) having the structure:

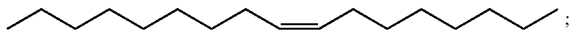 [SMILES: CCCCCCC/C=C\CCCCCCCC]

and Compound (IV) having the structure:

or agriculturally acceptable derivatives thereof.

4. A composition for inducing hygienic behavior in honey bees comprising the synergistic mixture of claim 1 and an agriculturally acceptable diluent or carrier.

5. A method of inducing hygienic behavior in honey bees, the method comprising contacting hive cells with the composition of claim 4.

6. The method of claim 5, wherein the hygienic behavior comprises eating diseased brood, eating diseased honey bees, removing diseased brood from hive cells, removing diseased honey bees from hive cells, removing pests or parasites, uncapping hive cells, or uncapping and recapping hive cells.

7. The method of claim 5, wherein the hygienic behavior comprises uncapping the contacted hive cells and removing pests or parasites.

8. The method of claim 5, wherein the hygienic behavior results in suppression of mite production, decreased mite survival, or suppression of a mite infestation.

9. The method of claim 5, wherein the hive cells are capped hive cells or uncapped hive cells.

10. The method of claim 6, wherein the diseased brood or diseased honey bees are infested with pests or parasites; infected with a pathogen; or damaged.

11. A composition for inducing hygienic behavior in honey bees comprising the synergistic mixture of claim 2 and an agriculturally acceptable diluent or carrier.

12. A method of inducing hygienic behavior in honey bees, the method comprising contacting hive cells with the composition of claim 11.

13. The method of claim 12, wherein the hygienic behavior comprises eating diseased brood, eating diseased honey bees, removing diseased brood from hive cells, removing diseased honey bees from hive cells, removing pests or parasites, uncapping hive cells, or uncapping and recapping hive cells.

14. The method of claim 12, wherein the hygienic behavior comprises uncapping the contacted hive cells and removing pests or parasites.

15. The method of claim 12, wherein the hygienic behavior results in suppression of mite production, decreased mite survival, or suppression of a mite infestation.

16. The method of claim 12, wherein the hive cells are capped hive cells or uncapped hive cells.

17. The method of claim 13, wherein the diseased brood or diseased honey bees are infested with pests or parasites; infected with a pathogen; or damaged.

18. A composition for inducing hygienic behavior in honey bees comprising the synergistic mixture of claim 3 and an agriculturally acceptable diluent or carrier.

19. A method of inducing hygienic behavior in honey bees, the method comprising contacting hive cells with the composition of claim 18.

20. The method of claim 19, wherein the hygienic behavior comprises eating diseased brood, eating diseased honey bees, removing diseased brood from hive cells, removing diseased honey bees from hive cells, removing pests or parasites, uncapping hive cells, or uncapping and recapping hive cells.

21. The method of claim 19, wherein the hygienic behavior comprises uncapping the contacted hive cells and removing pests or parasites.

22. The method of claim 19, wherein the hygienic behavior results in suppression of mite production, decreased mite survival, or suppression of a mite infestation.

23. The method of claim 19, wherein the hive cells are capped hive cells or uncapped hive cells.

24. The method of claim 20, wherein the diseased brood or diseased honey bees are infested with pests or parasites; infected with a pathogen; or damaged.

* * * * *